(12) United States Patent
El-Haddad et al.

(10) Patent No.: US 12,064,481 B2
(45) Date of Patent: Aug. 20, 2024

(54) COMPOSITIONS AND METHODS EMPLOYING ADENOSINE DEAMINASE-1 (ADA-1) AS AN ADJUVANT

(71) Applicant: Drexel University, Philadelphia, PA (US)

(72) Inventors: Elias El-Haddad, Downingtown, PA (US); Virginie Julie Tardif, Saint-Jean-du-Cardonnay (FR); Michele Aileen Kutzler, Souderton, PA (US)

( * ) Notice: Subject to any disclaimer, the term of this patent is extended or adjusted under 35 U.S.C. 154(b) by 203 days.

(21) Appl. No.: 17/517,535

(22) Filed: Nov. 2, 2021

(65) Prior Publication Data

US 2022/0133885 A1 May 5, 2022

Related U.S. Application Data

(60) Provisional application No. 63/108,642, filed on Nov. 2, 2020.

(51) Int. Cl.
| | |
|---|---|
| *A61K 39/39* | (2006.01) |
| *A61K 39/21* | (2006.01) |
| *A61K 39/215* | (2006.01) |
| *C12N 9/78* | (2006.01) |
| *A61K 39/00* | (2006.01) |

(52) U.S. Cl.
CPC .............. *A61K 39/39* (2013.01); *A61K 39/21* (2013.01); *A61K 39/215* (2013.01); *C12N 9/78* (2013.01); *A61K 2039/55516* (2013.01); *C07K 2319/30* (2013.01); *C12Y 305/04004* (2013.01)

(58) Field of Classification Search
CPC ...... A61K 39/39; A61K 39/21; A61K 39/215; A61K 2039/55516; A61K 2039/575; A61K 39/12; C12N 9/78; C12N 2740/16134; C12N 2770/20034; C07K 2319/30; C12Y 305/04004; A61P 31/14
See application file for complete search history.

(56) References Cited

FOREIGN PATENT DOCUMENTS

WO WO-2005000235 A2 * 1/2005 ............. A61P 31/00

OTHER PUBLICATIONS

Snkhchyan and Danielyan, "Functional genomics of adenosine deaminase in immune response", 2010, Հայաստանի pdcկրթականության, 50(1), 12-21. (Year: 2010).*
Zhou F, Yu T, Du R, Fan G, Liu Y, Liu Z, Xiang J, Wang Y, Song B, Gu X, et al.: Clinical course and risk factors for mortality of adult inpatients with COVID-19 in Wuhan, China: a retrospective cohort study. *Lancet* 2020, 395:1054-1062.
Guan WJ, Ni ZY, Hu Y, Liang WH, Ou CQ, He JX, Liu L, Shan H, Lei CL, Hui DSC, et al.: Clinical Characteristics of Coronavirus Disease 2019 in China. *N Engl J Med* 2020, 382:1708-1720.
Herati RS, Reuter MA, Dolfi DV, Mansfield KD, Aung H, Badwan OZ, Kurupati RK, Kannan S, Ertl H, Schmader KE, et al.: Circulating CXCR5+PD-1+ response predicts influenza vaccine antibody responses in young adults but not elderly adults. *J Immunol* 2014, 193:3528-3537.
Richner JM, Gmyrek GB, Govero J, Tu Y, van der Windt GJ, Metcalf TU, Haddad EK, Textor J, Miller MJ, Diamond MS: Age-Dependent Cell Trafficking Defects in Draining Lymph Nodes Impair Adaptive Immunity and Control of West Nile Virus Infection. *PLoS Pathog* 2015, 11:e1005027.
Sauer AV, Brigida I, Carriglio N, Hernandez RJ, Scaramuzza S, Clavenna D, Sanvito F, Poliani PL, Gagliani N, Carlucci F, et al.: Alterations in the adenosine metabolism and CD39/CD73 adenosinergic machinery cause loss of Treg cell function and autoimmunity in ADA-deficient SCID. *Blood* 2012, 119:1428-1439.
Gossage DL, Norby-Slycord CJ, Hershfield MS, Markert ML: A homozygous 5 base-pair deletion in exon 10 of the adenosine deaminase (ADA) gene in a child with severe combined immunodeficiency and very low levels of ADA mRNA and protein. *Hum Mol Genet* 1993, 2:1493-1494.
Hershfield M: Adenosine Deaminase Deficiency. In *GeneReviews((R))*. Edited by Adam MP, Ardinger HH, Pagon RA, Wallace SE, Bean LJH, Stephens K, Amemiya A; 1993.
Sauer AV, Brigida I, Carriglio N, Aiuti A: Autoimmune dysregulation and purine metabolism in adenosine deaminase deficiency. *Front Immunol* 2012, 3:265.
Apasov SG, Blackburn MR, Kellems RE, Smith PT, Sitkovsky MV: Adenosine deaminase deficiency increases thymic apoptosis and causes defective T cell receptor signaling. *J Clin Invest* 2001, 108:131-141.
Aiuti A, Cattaneo F, Galimberti S, Benninghoff U, Cassani B, Callegaro L, Scaramuzza S, Andolfi G, Mirolo M, Brigida I, et al.: Gene therapy for immunodeficiency due to adenosine deaminase deficiency. *N Engl J Med* 2009, 360:447-458.
Gary E, O'Connor M, Chakhtoura M, Tardif V, Kumova OK, Malherbe DC, Sutton WF, Haigwood NL, Kutzler MA, Haddad EK: Adenosine deaminase-1 enhances germinal center formation and functional antibody responses to HIV-1 Envelope DNA and protein vaccines. *Vaccine* 2020, 38:3821-3831.
Bhalla M, Simmons SR, Abamonte A, Herring SE, Roggensack SE, Bou Ghanem EN: Extracellular adenosine signaling reverses the age-driven decline in the ability of neutrophils to kill *Streptococcus pneumoniae*. *Aging Cell* 2020:e13218.
Bowers SM, Gibson KM, Cabral DA, Brown KL: Adenosine deaminase 2 activity negatively correlates with age during childhood. *Pediatr Rheumatol Online J* 2020, 18:54.

(Continued)

*Primary Examiner* — Nelson B Moseley, II
*Assistant Examiner* — Alyssa Rae Stonebraker
(74) *Attorney, Agent, or Firm* — Howson & Howson, LLP; Colleen M. Schaller

(57) ABSTRACT

Compositions and methods incorporating Adenosine deaminase-1 (ADA-1) as an adjuvant. Polynucleotides encoding novel coding sequences, polypeptides, vectors containing same, and methods of use are provided. ADA-1 is identified herein as a molecule that is able to enhance differentiation of $T_{FH}$ cells and thus is useful as a adjuvant in vaccine development.

19 Claims, 21 Drawing Sheets

Specification includes a Sequence Listing.

(56) References Cited

OTHER PUBLICATIONS

Candotti F, Shaw KL, Muul L, Carbonaro D, Sokolic R, Choi C, Schurman SH, Garabedian E, Kesserwan C, Jagadeesh GJ, et al.: Gene therapy for adenosine deaminase-deficient severe combined immune deficiency: clinical comparison of retroviral vectors and treatment plans. Blood 2012, 120:3635-3646.

Carbonaro DA, Jin X, Petersen D, Wang X, Dorey F, Kil KS, Aldrich M, Blackburn MR, Kellems RE, Kohn DB: In vivo transduction by intravenous injection of a lentiviral vector expressing human ADA into neonatal ADA gene knockout mice: a novel form of enzyme replacement therapy for ADA deficiency. Mol Ther 2006, 13:1110-1120.

Shaw KL, Garabedian E, Mishra S, Barman P, Davila A, Carbonaro D, Shupien S, Silvin C, Geiger S, Nowicki B, et al.: Clinical efficacy of gene-modified stem cells in adenosine deaminase-deficient immunodeficiency. *J Clin Invest* 2017, 127:1689-1699.

Hill DL, Pierson W, Bolland DJ, Mkindi C, Carr EJ, Wang J, Houard S, Wingett SW, Audran R, Wallin EF, et al.: The adjuvant GLA-SE promotes human Tfh cell expansion and emergence of public TCRbeta clonotypes. *J Exp Med* 2019, 216:1857-1873.

Riteau N, Sher A: Chitosan: An Adjuvant with an Unanticipated STING. *Immunity* 2016, 44:522-524.

Mastelic Gavillet B, Eberhardt CS, Auderset F, Castellino F, Seubert A, Tregoning JS, Lambert PH, de Gregorio E, Del Giudice G, Siegrist CA: MF59 Mediates Its B Cell Adjuvanticity by Promoting T Follicular Helper Cells and Thus Germinal Center Responses in Adult and Early Life. *J Immunol* 2015, 194:4836-4845.

Pompano RR, Chen J, Verbus EA, Han H, Fridman A, McNeely T, Collier JH, Chong AS: Titrating T-cell epitopes within self-assembled vaccines optimizes CD4+ helper T cell and antibody outputs. Adv Healthc Mater 2014, 3:1898-1908.

Guarner J: Three Emerging Coronaviruses in Two Decades. *Am J Clin Pathol* 2020, 153:420-421.

Du L, He Y, Zhou Y, Liu S, Zheng BJ, Jiang S: The spike protein of SARS-CoV—a target for vaccine and therapeutic development. Nat Rev Microbiol 2009, 7:226-236.

Coutard B, Valle C, de Lamballerie X, Canard B, Seidah NG, Decroly E: The spike glycoprotein of the new coronavirus 2019-nCoV contains a furin-like cleavage site absent in CoV of the same clade. *Antiviral Res* 2020, 176:104742.

He Y, Zhou Y, Liu S, Kou Z, Li W, Farzan M, Jiang S: Receptor-binding domain of SARS-CoV spike protein induces highly potent neutralizing antibodies: implication for developing subunit vaccine. Biochem Biophys Res Commun 2004, 324:773-781.

Graham RL, Donaldson EF, Baric RS: A decade after SARS: strategies for controlling emerging coronaviruses. Nat Rev Microbiol 2013, 11:836-848.

Thevarajan I, Buising KL, Cowie BC: Clinical presentation and management of COVID-19. Med J Aust 2020, 213:134-139.

Climent N, Martinez-Navio JM, Gil C, Garcia F, Rovira C, Hurtado C, Miralles L, Gatell JM, Gallart T, Mallol J, et al.: Adenosine deaminase enhances T-cell response elicited by dendritic cells loaded with inactivated HIV. Immunol Cell Biol 2009, 87:634-639.

Martinez-Navio JM, Climent N, Pacheco R, Garcia F, Plana M, Nomdedeu M, Oliva H, Rovira C, Miralles L, Gatell JM, et al.: Immunological dysfunction in HIV-1-infected individuals caused by impairment of adenosine deaminase-induced costimulation of T-cell activation. Immunology 2009, 128:393-404.

Baliban SM, Michael A, Shammassian B, Mudakha S, Khan AS, Cocklin S, Zentner I, Latimer BP, Bouillaut L, Hunter M, et al.: An optimized, synthetic DNA vaccine encoding the toxin A and toxin B receptor binding domains of Clostridium difficile induces protective antibody responses in vivo. Infect Immun 2014, 82:4080-4091.

Laddy DJ, Yan J, Kutzler M, Kobasa D, Kobinger GP, Khan AS, Greenhouse J, Sardesai NY, Draghia-Akli R, Weiner DB: Heterosubtypic protection against pathogenic human and avian influenza viruses via in vivo electroporation of synthetic consensus DNA antigens. PLoS One 2008, 3:e2517.

Kutzler MA, Robinson TM, Chattergoon MA, Choo DK, Choo AY, Choe PY, Ramanathan MP, Parkinson R, Kudchodkar S, Tamura Y, et al.: Coimmunization with an optimized IL-15 plasmid results in enhanced function and longevity of CD8 T cells that are partially independent of CD4 T cell help. J Immunol 2005, 175:112-123.

Latimer B, Toporovski R, Yan J, Pankhong P, Morrow MP, Khan AS, Sardesai NY, Welles SL, Jacobson JM, Weiner DB, et al.: Strong HCV NS3/4a, NS4b, NS5a, NS5b-specific cellular immune responses induced in Rhesus macaques by a novel HCV genotype 1a/1b consensus DNA vaccine. Hum Vaccin Immunother 2014, 10:2357-2365.

Kutzler MA, Wise MC, Hutnick NA, Moldoveanu Z, Hunter M, Reuter M, Yuan S, Yan J, Ginsberg A, Sylvester A, et al.: Chemokine-adjuvanted electroporated DNA vaccine induces substantial protection from simian immunodeficiency virus vaginal challenge. Mucosal Immunol 2016, 9:13-23.

Kathuria N, Kraynyak KA, Carnathan D, Betts M, Weiner DB, Kutzler MA: Generation of antigen-specific immunity following systemic immunization with DNA vaccine encoding CCL25 chemokine immunoadjuvant. Hum Vaccin Immunother 2012, 8:1607-1619.

Gary EN, Kathuria N, Makurumidze G, Curatola A, Ramamurthi A, Bernui ME, Myles D, Yan J, Pankhong P, Muthumani K, et al.: CCR10 expression is required for the adjuvant activity of the mucosal chemokine CCL28 when delivered in the context of an HIV-1 Env DNA vaccine. Vaccine 2020, 38:2626-2635.

Ibarrondo FJ, Fulcher JA, Goodman-Meza D, Elliott J, Hofmann C, Hausner MA, Ferbas KG, Tobin NH, Aldrovandi GM, Yang OO: Rapid decay of anti-SARS-CoV-2 antibodies in persons with mild Covid-19. New England Journal of Medicine 2020.

Ghneim H, Al-Saleh S, Al-Shammary F, Kordee ZJCB: Changes in adenosine deaminase activity in ageing cultured human cells and the role of zinc. 2003, 21:275-282.

Dullaers M, Li D, Xue Y, Ni L, Gayet I, Morita R, Ueno H, Palucka KA, Banchereau J, Oh S: A T cell-dependent mechanism for the induction of human mucosal homing immunoglobulin A-secreting plasmablasts. Immunity 2009, 30:120-129.

King IL, Mohrs M: IL-4-producing CD4+ T cells in reactive lymph nodes during helminth infection are T follicular helper cells. J Exp Med 2009, 206:1001-1007.

Reinhardt RL, Liang HE, Locksley RM: Cytokine-secreting follicular T cells shape the antibody repertoire. Nat Immunol 2009, 10:385-393.

Yusuf I, Kageyama R, Monticelli L, Johnston RJ, Ditoro D, Hansen K, Barnett B, Crotty S: Germinal center T follicular helper cell IL-4 production is dependent on signaling lymphocytic activation molecule receptor (CD150). J Immunol 2010, 185:190-202.

Tardif V, Muir R, Cubas R, Chakhtoura M, Wilkinson P, Metcalf T, Herro R, Haddad EK: Adenosine deaminase-1 delineates human follicular helper T cell function and is altered with HIV. Nat Commun 2019, 10:823.

Valerio D, Duyvesteyn MG, van Ormondt H, Meera Khan P, van der Eb AJ: Adenosine deaminase (ADA) deficiency in cells derived from humans with severe combined immunodeficiency is due to an aberration of the ADA protein. Nucleic Acids Res 1984, 12:1015-1024.

Metcalf TU, Cubas RA, Ghneim K, Cartwright MJ, Grevenynghe JV, Richner JM, Olagnier DP, Wilkinson PA, Cameron MJ, Park BS, et al.: Global analyses revealed age-related alterations in innate immune responses after stimulation of pathogen recognition receptors. Aging Cell 2015, 14:421-432.

Metcalf TU, Wilkinson PA, Cameron MJ, Ghneim K, Chiang C, Wertheimer AM, Hiscott JB, Nikolich-Zugich J, Haddad EK: Human Monocyte Subsets Are Transcriptionally and Functionally Altered in Aging in Response to Pattern Recognition Receptor Agonists. J Immunol 2017, 199:1405-1417.

Boyd SD, Joshi SA: High-Throughput DNA Sequencing Analysis of Antibody Repertoires. Microbiol Spectr 2014, 2.

Gur Yaari SHK: Practical guidelines for B-cell receptor repertoire sequencing analysis. Genome Medicine 2015, 7:121.

(56) References Cited

OTHER PUBLICATIONS

Kashiwagi S, Yuan J, Forbes B, Hibert ML, Lee EL, Whicher L, Goudie C, Yang Y, Chen T, Edelblute B, et al.: Near-infrared laser adjuvant for influenza vaccine. PLoS One 2013, 8:e82899.

Laura P. van Lieshout JMD, Tara N. Rindler, Stephanie A. Booth, James P. Bridges, Sarah K. Wootton: Novel Triple-Mutant AAV6 Capsid Induces Rapid and Potent Transgene Expression in the Muscle and Respiratory Tract of Mice. Methods and Clinical Development 2018, 9:323-329.

Buckley RH: Molecular defects in human severe combined immunodeficiency and approaches to immune reconstitution. Annu Rev Immunol 2004, 22:625-655.

Franco R, Pacheco R, Gatell JM, Gallart T, Lluis C: Enzymatic and extraenzymatic role of adenosine deaminase 1 in T-cell-dendritic cell contacts and in alterations of the immune function. Critical Reviews™ in Immunology 2007, 27(6).

Pacheco R, Martinez-Navio J, Lejeune M, Climent N, Oliva H, Gatell J, Gallart T, Mallol J, Lluis C, Franco R: CD26, adenosine deaminase, and adenosine receptors mediate costimulatory signals in the immunological synapse. Proceedings of the National Academy of Sciences 2005, 102(27):9583-9588.

Casanova V, Naval-Macabuhay I, Massanella M, Rodríguez-García M, Blanco J, Gatell JM, García F, Gallart T, Lluis C, Mallol J: Adenosine deaminase enhances the immunogenicity of human dendritic cells from healthy and HIV-infected individuals. PloS one 2012, 7(12):e51287.

Schmitt N, Morita R, Bourdery L, Bentebibel SE, Zurawski SM, Banchereau J, Ueno H: Human dendritic cells induce the differentiation of interleukin-21-producing T follicular helper-like cells through interleukin-12. Immunity 2009, 31(1):158-169.

Chakarov S, Fazilleau N: Monocyte-derived dendritic cells promote T follicular helper cell differentiation. EMBO molecular medicine 2014, 6(5):590-603.

Ballesteros-Tato A, Randall TD: Priming of T follicular helper cells by dendritic cells. Immunology and cell biology 2014, 92(1):22-27.

León B, Ballesteros-Tato A, Browning JL, Dunn R, Randall TD, Lund FE: Regulation of T H 2 development by CXCR5+ dendritic cells and lymphotoxin-expressing B cells. Nature immunology 2012, 13(7):681.

Havenar-Daughton C, Carnathan DG, de la Peña AT, Pauthner M, Briney B, Reiss SM, Wood JS, Kaushik K, van Gils MJ, Rosales SL: Direct probing of germinal center responses reveals immunological features and bottlenecks for neutralizing antibody responses to HIV Env trimer. Cell reports 2016, 17(9):2195-2209.

Hu JK, Crampton JC, Cupo A, Ketas T, van Gils MJ, Sliepen K, de Taeye SW, Sok D, Ozorowski G, Deresa I: Murine antibody responses to cleaved soluble HIV-1 envelope trimers are highly restricted in specificity. Journal of virology 2015, 89(20):10383-10398.

Yan J, Yoon H, Kumar S, Ramanathan MP, Corbitt N, Kutzler M, Dai A, Boyer JD, Weiner DB: Enhanced cellular immune responses elicited by an engineered HIV-1 subtype B consensus-based envelope DNA vaccine. Molecular Therapy 2007, 15(2):411-421.

Desrosiers MD, Cembrola KM, Fakir MJ, Stephens LA, Jama FM, Shameli A, Mehal WZ, Santamaria P, Shi Y: Adenosine deamination sustains dendritic cell activation in inflammation. The Journal of Immunology 2007, 179(3):1884-1892.

Choi YS, Kageyama R, Eto D, Escobar TC, Johnston RJ, Monticelli L, Lao C, Crotty S: ICOS receptor instructs T follicular helper cell versus effector cell differentiation via induction of the transcriptional repressor Bcl6. Immunity 2011, 34(6):932-946.

Choi YS, Kageyama R, Eto D, Escobar TC, Johnston RJ, Monticelli L, Lao C, Crotty S: Bcl6 dependent T follicular helper cell differentiation diverges from effector cell differentiation during priming and depends on the gene Icos. Immunity 2011, 34(6):932.

Choi YS, Yang JA, Crotty S: Dynamic regulation of Bcl6 in follicular helper CD4 T (Tfh) cells. Current opinion in immunology 2013, 25(3):366-372.

Crotty S: T follicular helper cell differentiation, function, and roles in disease. Immunity 2014, 41(4):529-542.

Pedros C, Zhang Y, Hu JK, Choi YS, Canonigo-Balancio AJ, Yates III JR, Altman A, Crotty S, Kong K-F: A TRAF-like motif of the inducible costimulator ICOS controls development of germinal center T FH cells via the kinase TBK1. Nature immunology 2016, 17(7):825.

Weinstein JS, Bertino SA, Hernandez SG, Poholek AC, Teplitzky TB, Nowyhed HN, Craft J: B cells in T follicular helper cell development and function: separable roles in delivery of ICOS ligand and antigen. The Journal of Immunology 2014, 192(7):3166-3179.

Blanco P, Palucka AK, Pascual V, Banchereau J: Dendritic cells and cytokines in human inflammatory and autoimmune diseases. Cytokine & growth factor reviews 2008, 19(1):41-52.

Chavele K-M, Merry E, Ehrenstein MR: Cutting edge: circulating plasmablasts induce the differentiation of human T follicular helper cells via IL-6 production. The Journal of Immunology 2015, 194(6):2482-2485.

Eto D, Lao C, DiToro D, Barnett B, Escobar TC, Kageyama R, Yusuf I, Crotty S: IL-21 and IL-6 are critical for different aspects of B cell immunity and redundantly induce optimal follicular helper CD4 T cell (Tfh) differentiation. PloS one 2011, 6(3):e17739.

Papillion AM, Bachus H, Fuller M, León B, Ballesteros-Tato A: IL-6 counteracts IL-2-dependent suppression of T follicular helper cell responses. In.: Am Assoc Immnol; 2018.

Choi YS, Eto D, Yang JA, Lao C, Crotty S: Cutting edge: STAT1 is required for IL-6-mediated Bcl6 induction for early follicular helper cell differentiation. The Journal of Immunology 2013, 190(7):3049-3053.

Wu X-B, Cao D-L, Zhang X, Jiang B-C, Zhao L-X, Qian B, Gao Y-J: CXCL13/CXCR5 enhances sodium channel Nav1. 8 current density via p38 MAP kinase in primary sensory neurons following inflammatory pain. Scientific reports 2016, 6:34836.

Cucak H, Yrlid U, Reizis B, Kalinke U, Johansson-Lindbom B: Type I interferon signaling in dendritic cells stimulates the development of lymph-node-resident T follicular helper cells. Immunity 2009, 31(3):491-501.

Ritvo P-G, Klatzmann D: Interleukin-1 in the response of follicular helper and follicular regulatory T cells. Frontiers in immunology 2019, 10.

Schmitt N, Bustamante J, Bourdery L, Bentebibel SE, Boisson-Dupuis S, Hamlin F, Tran MV, Blankenship D, Pascual V, Savino DA: IL-12 receptor β1 deficiency alters in vivo T follicular helper cell response in humans. Blood 2013, 121(17):3375-3385.

Martinez V, Costagliola D, Bonduelle O, N'go N, Schnuriger A, Théodorou I, Clauvel J-P, Sicard D, Agut H, Debré P: Combination of HIV-1-specific CD4 Th1 cell responses and IgG2 antibodies is the best predictor for persistence of long-term nonprogression. Journal of Infectious Diseases 2005, 191(12):2053-2063.

Zhu C, Ma J, Liu Y, Tong J, Tian J, Chen J, Tang X, Xu H, Lu L, Wang S: Increased frequency of follicular helper T cells in patients with autoimmune thyroid disease. The Journal of Clinical Endocrinology & Metabolism 2012, 97(3):943-950.

Linterman MA, Rigby RJ, Wong RK, Yu D, Brink R, Cannons JL, Schwartzberg PL, Cook MC, Walters GD, Vinuesa CG: Follicular helper T cells are required for systemic autoimmunity. Journal of Experimental Medicine 2009, 206(3):561-576.

Morita R, Schmitt N, Bentebibel S-E, Ranganathan R, Bourdery L, Zurawski G, Foucat E, Dullaers M, Oh S, Sabzghabaei N: Human blood CXCR5+ CD4+ T cells are counterparts of T follicular cells and contain specific subsets that differentially support antibody secretion. Immunity 2011, 34(1):108-121.

Wang S, Kennedy JS, West K, Montefiori DC, Coley S, Lawrence J, Shen S, Green S, Rothman AL, Ennis FA: Cross-subtype antibody and cellular immune responses induced by a polyvalent DNA prime-protein boost HIV-1 vaccine in healthy human volunteers. Vaccine 2008, 26(31):3947-3957.

Letvin NL, Montefiori DC, Yasutomi Y, Perry HC, Davies M-E, Lekutis C, Alroy M, Freed DC, Lord CI, Handt LK: Potent, protective anti-HIV immune responses generated by bimodal HIV envelope DNA plus protein vaccination. Proceedings of the National Academy of Sciences 1997, 94(17):9378-9383.

Van Diepen MT, Chapman R, Douglass N, Galant S, Moore PL, Margolin E, Ximba P, Morris L, Rybicki EP, Williamson A-L:

(56) References Cited

OTHER PUBLICATIONS

Prime-boost immunizations with DNA, modified vaccinia virus Ankara, and protein-based vaccines elicit robust HIV-1 tier 2 neutralizing antibodies against the CAP256 superinfecting virus. Journal of Virology 2019, 93(8):e02155-02118.

Pissani F, Malherbe DC, Schuman JT, Robins H, Park BS, Krebs SJ, Barnett SW, Haigwood NL: Improvement of antibody responses by HIV envelope DNA and protein co-immunization. Vaccine 2014, 32(4):507-513.

Wibmer CK, Bhiman JN, Gray ES, Tumba N, Karim SSA, Williamson C, Morris L, Moore PL: Viral escape from HIV-1 neutralizing antibodies drives increased plasma neutralization breadth through sequential recognition of multiple epitopes and immunotypes. PLoS pathogens 2013, 9(10):e1003738.

Crotty S: Follicular helper CD4 T cells (Tfh). Annual review of immunology 2011, 29:621-663.

Binley JM, Wrin T, Korber B, Zwick MB, Wang M, Chappey C, Stiegler G, Kunert R, Zolla-Pazner S, Katinger H: Comprehensive cross-clade neutralization analysis of a panel of anti-human immunodeficiency virus type 1 monoclonal antibodies. Journal of virology 2004, 78(23):13232-13252.

Kepler TB, Liao H-X, Alam SM, Bhaskarabhatla R, Zhang R, Yandava C, Stewart S, Anasti K, Kelsoe G, Parks R: Immunoglobulin gene insertions and deletions in the affinity maturation of HIV-1 broadly reactive neutralizing antibodies. Cell host & microbe 2014, 16(3):304-313.

Klein F, Diskin R, Scheid JF, Gaebler C, Mouquet H, Georgiev IS, Pancera M, Zhou T, Incesu R-B, Fu BZ: Somatic mutations of the immunoglobulin framework are generally required for broad and potent HIV-1 neutralization. Cell 2013, 153(1):126-138.

Locci M, Havenar-Daughton C, Landais E, Wu J, Kroenke MA, Arlehamn CL, Su LF, Cubas R, Davis MM, Sette A: Human circulating PD-1+ CXCR3-CXCR5+ memory Tfh cells are highly functional and correlate with broadly neutralizing HIV antibody responses. Immunity 2013, 39(4):758-769.

Ogata M, Ito T, Shimamoto K, Nakanishi T, Satsutani N, Miyamoto R, Nomura S: Plasmacytoid dendritic cells have a cytokine-producing capacity to enhance ICOS ligand-mediated IL-10 production during T-cell priming. International immunology 2012, 25(3):171-182.

Ma CS, Suryani S, Avery DT, Chan A, Nanan R, Santner-Nanan B, Deenick EK, Tangye SG: Early commitment of naïve human CD4+ T cells to the T follicular helper (TFH) cell lineage is induced by IL-12. Immunology and cell biology 2009, 87(8):590-600.

Oestreich KJ, Mohn SE, Weinmann AS: Molecular mechanisms that control the expression and activity of Bcl-6 in TH1 cells to regulate flexibility with a T FH-like gene profile. Nature immunology 2012, 13(4):405.

McDonald KG, McDonough JS, Dieckgraefe BK, Newberry RD: Dendritic cells produce CXCL13 and participate in the development of murine small intestine lymphoid tissues. The American journal of pathology 2010, 176(5):2367-2377.

Cai G, Nie X, Zhang W, Wu B, Lin J, Wang H, Jiang C, Shen Q: A regulatory role for IL-10 receptor signaling in development and B cell help of T follicular helper cells in mice. The Journal of Immunology 2012, 189(3):1294-1302.

Avery DT, Bryant VL, Ma CS, de Waal Malefyt R, Tangye SG: IL-21-induced isotype switching to IgG and IgA by human naive B cells is differentially regulated by IL-4. The Journal of Immunology 2008, 181(3):1767-1779.

Lim HW, Hillsamer P, Banham AH, Kim CH: Cutting edge: direct suppression of B cells by CD4+ CD25+ regulatory T cells. The Journal of Immunology 2005, 175(7):4180-4183.

Rahim SS, Khan N, Boddupalli CS, Hasnain SE, Mukhopadhyay S: Interleukin-10 (IL-10) mediated suppression of IL-12 production in RAW 264.7 cells also involves c-rel transcription factor. Immunology 2005, 114(3):313-321.

Brigida I, Sauer AV, Ferrua F, Giannelli S, Scaramuzza S, Pistoia V, Castiello MC, Barendregt BH, Cicalese MP, Casiraghi M: B-cell development and functions and therapeutic options in adenosine deaminase-deficient patients. Journal of Allergy and Clinical Immunology 2014, 133(3):799-806. e710.

Kräutler NJ, Suan D, Butt D, Bourne K, Hermes JR, Chan TD, Sundling C, Kaplan W, Schofield P, Jackson J: Differentiation of germinal center B cells into plasma cells is initiated by high-affinity antigen and completed by Tfh cells. Journal of Experimental Medicine 2017, 214(5):1259-1267.

Ise W, Fujii K, Shiroguchi K, Ito A, Kometani K, Takeda K, Kawakami E, Yamashita K, Suzuki K, Okada T: T follicular helper cell-germinal center B cell interaction strength regulates entry into plasma cell or recycling germinal center cell fate. Immunity 2018, 48(4):702-715. e704.

Suan D, Sundling C, Brink R: Plasma cell and memory B cell differentiation from the germinal center. Current opinion in immunology 2017, 45:97-102.

Yan J, Corbitt N, Pankhong P, Shin T, Khan A, Sardesai NY, Weiner DB: Immunogenicity of a novel engineered HIV-1 clade C synthetic consensus-based envelope DNA vaccine. Vaccine 2011, 29(41):7173-7181.

Muthumani K, Zhang D, Dayes NS, Hwang DS, Calarota SA, Choo AY, Boyer JD, Weiner DB: Novel engineered HIV-1 East African Clade-A gp160 plasmid construct induces strong humoral and cell-mediated immune responses in vivo. Virology 2003, 314(1):134-146.

Malherbe DC, Doria-Rose NA, Misher L, Beckett T, Puryear WB, Schuman JT, Kraft Z, O'Malley J, Mori M, Srivastava I: Sequential immunization with a subtype B HIV-1 envelope quasispecies partially mimics the in vivo development of neutralizing antibodies. Journal of virology 2011, 85(11):5262-5274.

Sellhorn G, Caldwell Z, Mineart C, Stamatatos L: Improving the expression of recombinant soluble HIV Envelope glycoproteins using pseudo-stable transient transfection. Vaccine 2009, 28(2):430-436.

* cited by examiner

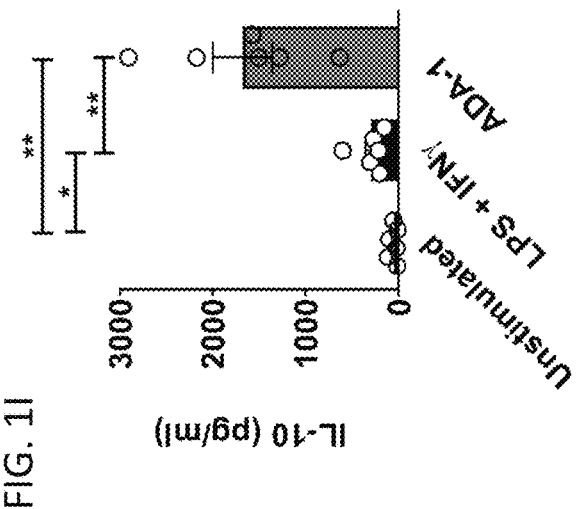
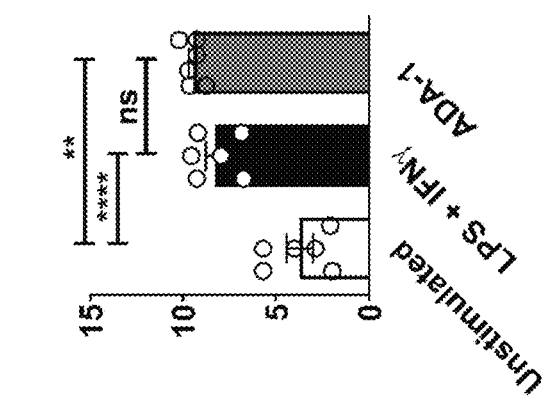
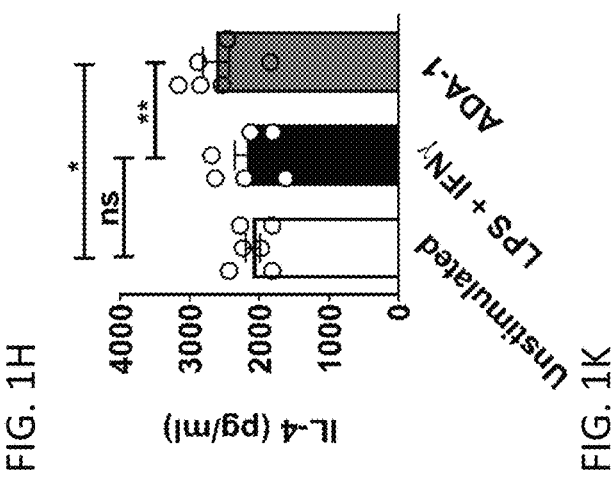
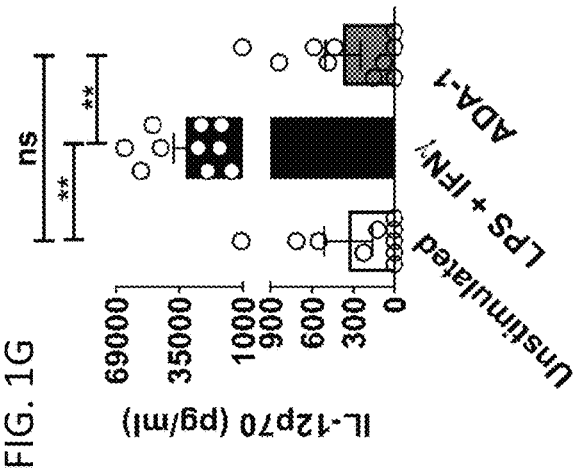
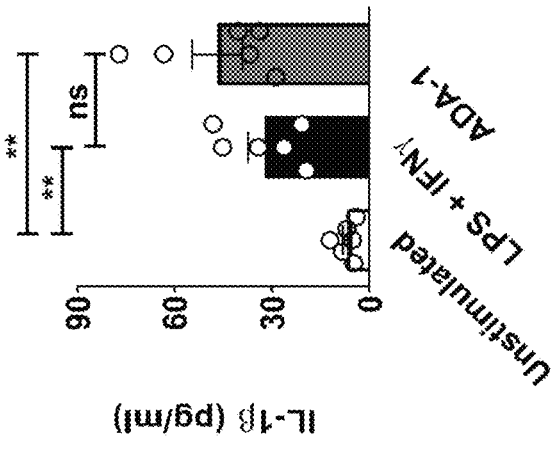

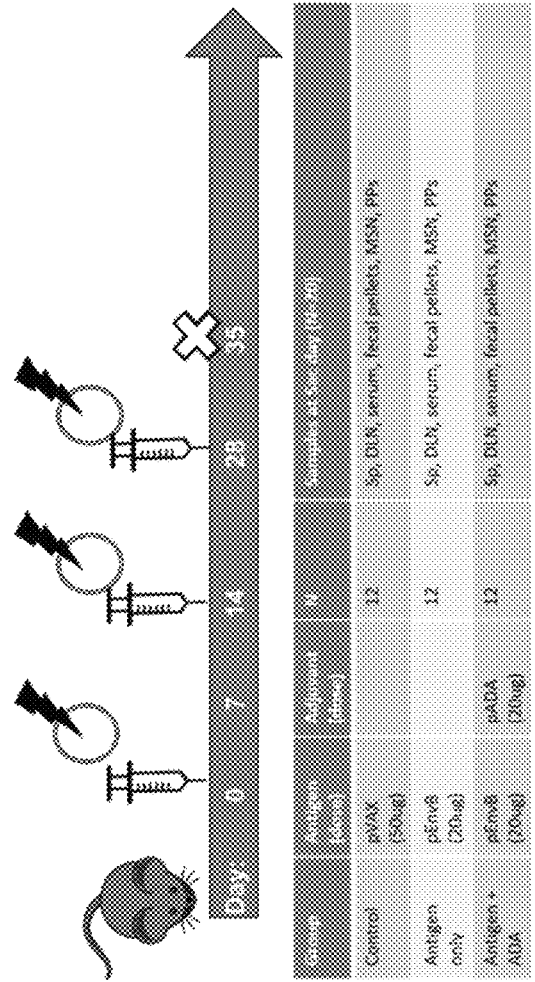
FIG. 2A
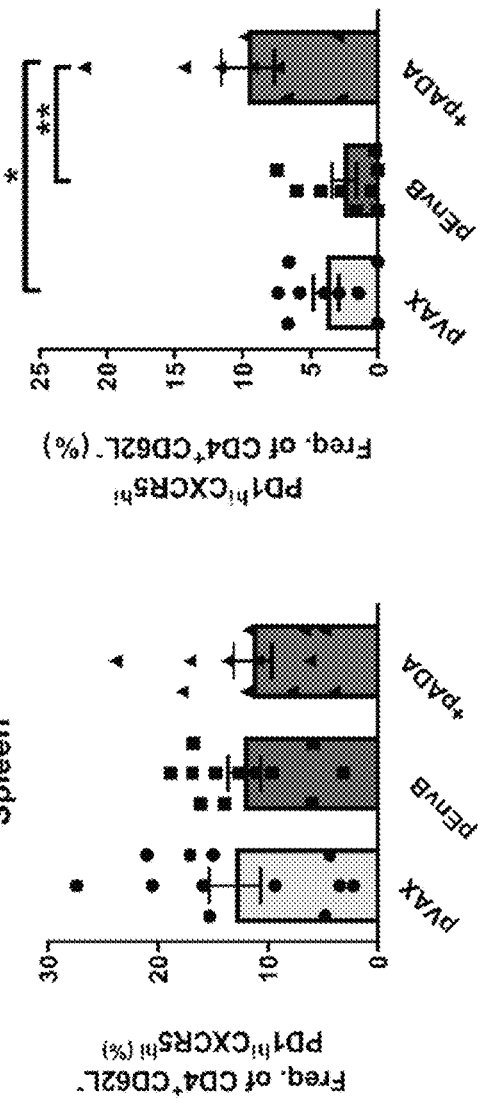
FIG. 2B Germinal center $T_{FH}$ in Spleen
FIG. 2C Germinal center $T_{FH}$ in Popliteal and Inguinal LNs HIV 96Z-Binding Serum IgG
Day 3 post-3rd Immunization HIV 96Z-Binding Serum IgG
Day 6 post-3rd Immunization HIV 96Z-Binding Serum IgG
Day 12 post-3rd Immunization

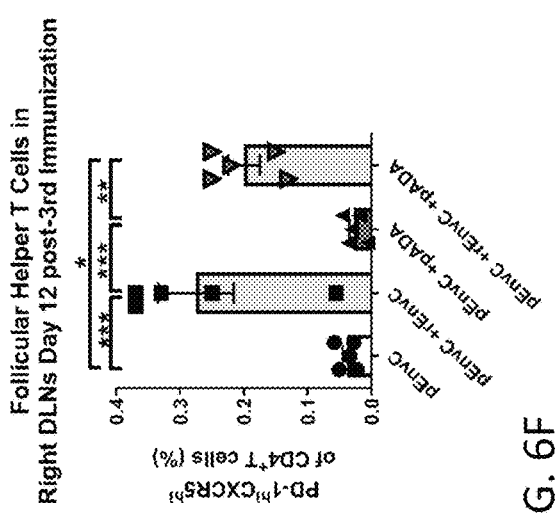
FIG. 6A
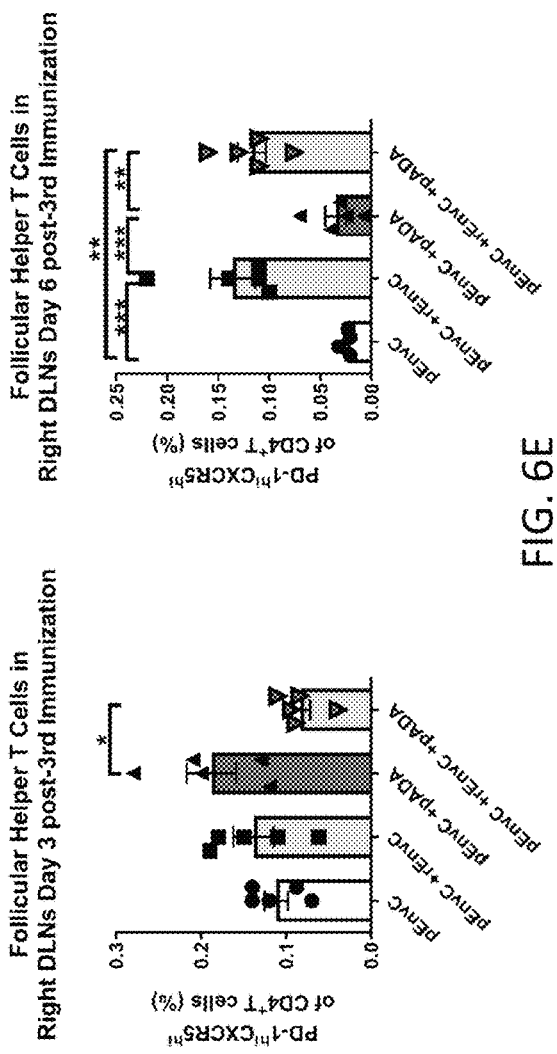
FIG. 6B
FIG. 6C
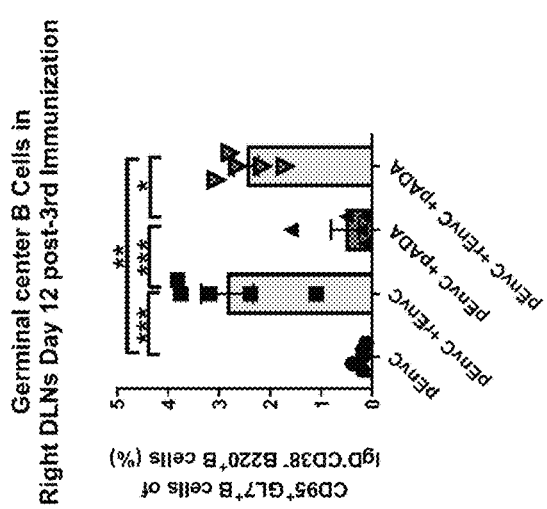
FIG. 6D
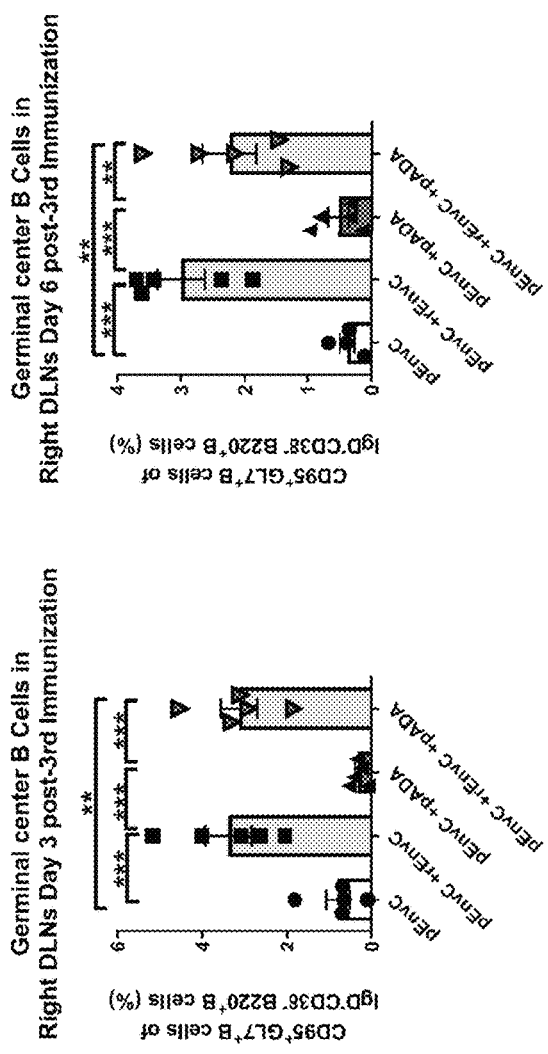
FIG. 6E
FIG. 6F

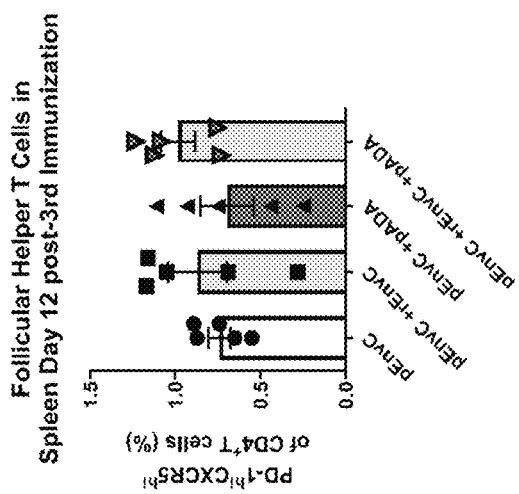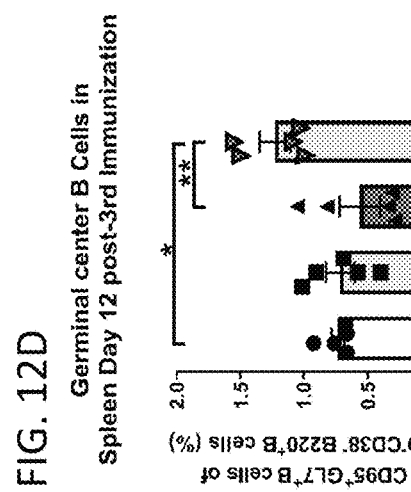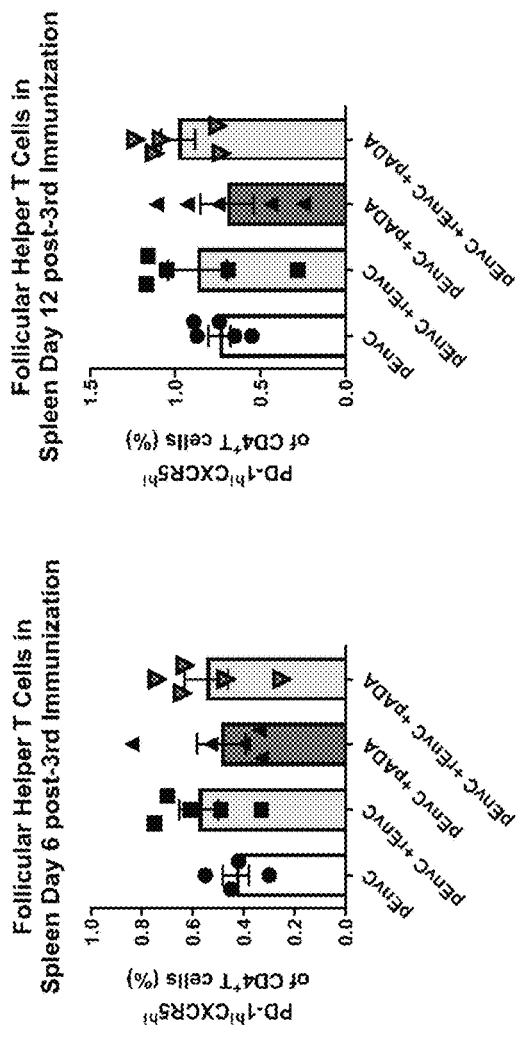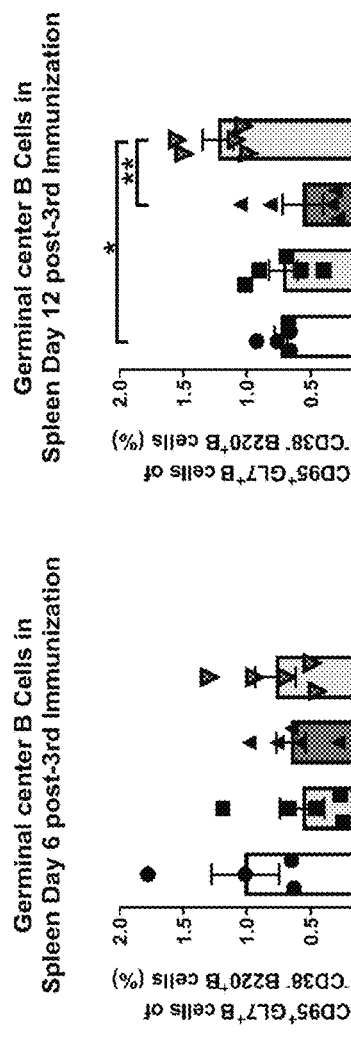

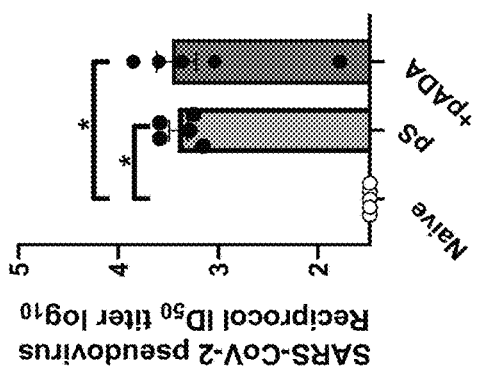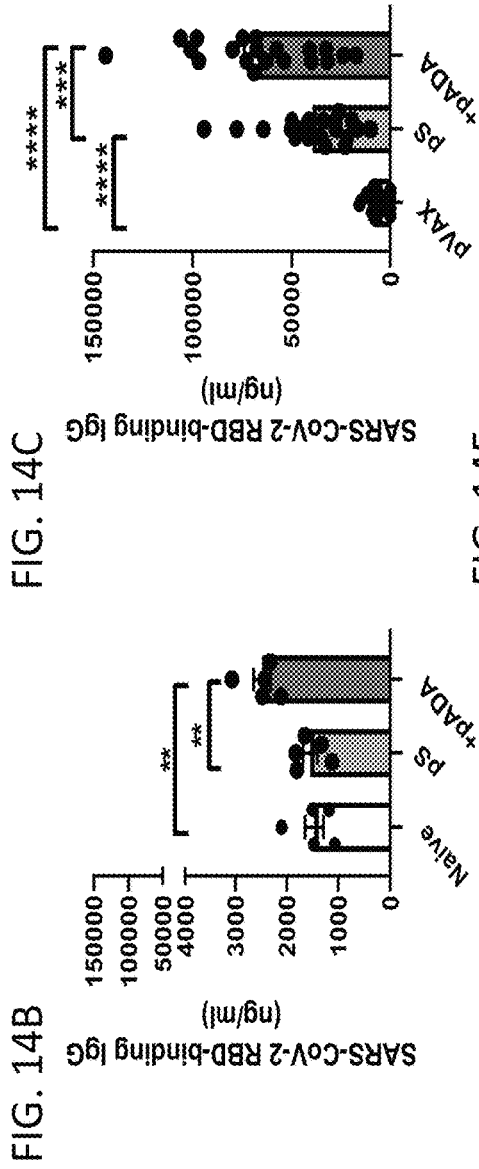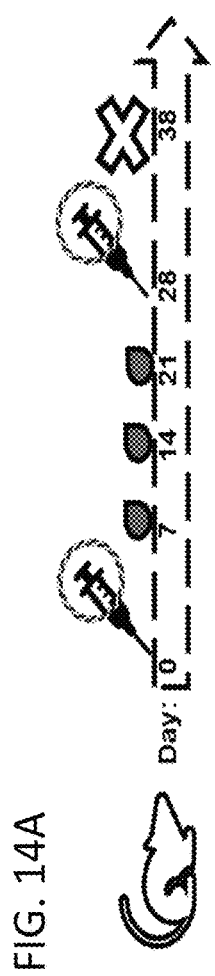

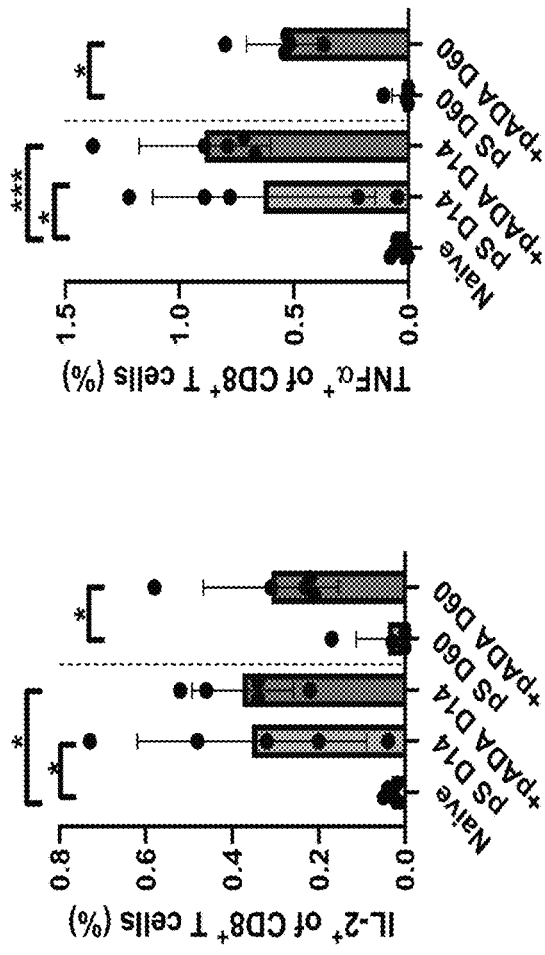
FIG. 16A
FIG. 16B
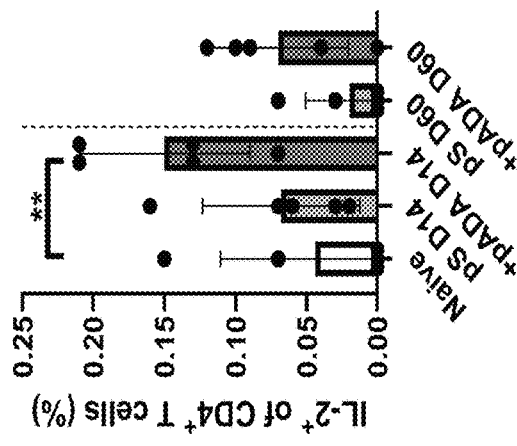
FIG. 16C
FIG. 16D

SEQUENCE LISTING

<160> NUMBER OF SEQ ID NOS: 9

<210> SEQ ID NO 1
<211> LENGTH: 1089
<212> TYPE: DNA
<213> ORGANISM: Homo sapiens

<400> SEQUENCE: 1

| | | | | | |
|---|---|---|---|---|---|
| atggcgcaaa | ccccggcgtt | cgataagccg | aaagtggagc | tgcatgttca | tctggacggt | 60 |
| agcatcaaac | cggaaaccat | tctgtattat | ggtcgtcgtc | gtggtattgc | gctgccggcg | 120 |
| aacaccgcgg | aaggtctgct | gaacgtgatt | ggcatggaca | agccgctgac | cctgccggac | 180 |
| ttcctggcga | aatttgatta | ctatatgccg | gcgattgcgg | gttgccgtga | ggcgatcaag | 240 |
| cgtattgcgt | atgagttcgt | ggagatgaag | gcgaaagaag | gtgtggttta | cgttgaggtg | 300 |
| cgctatagcc | cgcacctgct | ggcgaacagc | aaagttgaac | cgatcccgtg | gaaccaagcg | 360 |
| gaaggcgacc | tgaccccgga | tgaggtggtt | gcgctggttg | gtcaaggcct | gcaggaaggt | 420 |
| gaacgtgatt | ttggcgttaa | ggcgcgtagc | attctgtgct | gcatgcgtca | ccagccgaac | 480 |
| tggagcccga | agtggttga | actgtgcaag | aaataccagc | aacagaccgt | ggttgcgatc | 540 |
| gacctggcgg | tgatgaaac | catcccgggc | agcagcctgc | tgccgggtca | tgtgcaagcg | 600 |
| tatcaggaag | cggttaagag | cggtatccac | cgtaccgtgc | atgcgggtga | ggttggcagc | 660 |
| gcggaagtgg | ttaaagaggc | ggtggacatt | ctgaaaaccg | aacgtctggg | tcacggctac | 720 |
| cacaccctgg | aggatcaagc | gctgtataac | cgtctgcgtc | aggaaaacat | gcacttcgag | 780 |
| atttgcccgt | ggagcagcta | tctgaccggt | gcgtggaagc | cggacaccga | acacgcggtt | 840 |
| atccgtctga | aaaacgatca | agcgaactac | agcctgaaca | ccgacgatcc | gctgattttc | 900 |
| aagagcaccc | tggacaccga | ttatcagatg | accaaacgtg | acatgggttt | caccgaggaa | 960 |
| gagtttaagc | gtctgaacat | taacgcggcg | aaaagcagct | ttctgccgga | agatgagaaa | 1020 |
| cgtgagctgc | tggacctgct | gtataaagcg | tatggtatgc | cgccgagcgc | gagcgcgggc | 1080 |
| caaaatctg | | | | | | 1089 |

<210> SEQ ID NO 2
<211> LENGTH: 363
<212> TYPE: PRT
<213> ORGANISM: Homo sapiens

<400> SEQUENCE: 2

Met Ala Gln Thr Pro Ala Phe Asp Lys Pro Lys Val Glu Leu His Val
1               5                   10                  15

His Leu Asp Gly Ser Ile Lys Pro Glu Thr Ile Leu Tyr Tyr Gly Arg
            20                  25                  30

Arg Arg Gly Ile Ala Leu Pro Ala Asn Thr Ala Glu Gly Leu Leu Asn
        35                  40                  45

Val Ile Gly Met Asp Lys Pro Leu Thr Leu Pro Asp Phe Leu Ala Lys
    50                  55                  60

Phe Asp Tyr Tyr Met Pro Ala Ile Ala Gly Cys Arg Glu Ala Ile Lys
65                  70                  75                  80

Arg Ile Ala Tyr Glu Phe Val Glu Met Lys Ala Lys Glu Gly Val Val
                85                  90                  95

Tyr Val Glu Val Arg Tyr Ser Pro His Leu Leu Ala Asn Ser Lys Val
            100                 105                 110

Glu Pro Ile Pro Trp Asn Gln Ala Glu Gly Asp Leu Thr Pro Asp Glu
        115                 120                 125

```
Val Val Ala Leu Val Gly Gln Gly Leu Gln Glu Gly Glu Arg Asp Phe
        130                 135                 140

Gly Val Lys Ala Arg Ser Ile Leu Cys Cys Met Arg His Gln Pro Asn
145                 150                 155                 160

Trp Ser Pro Lys Val Val Glu Leu Cys Lys Lys Tyr Gln Gln Gln Thr
                165                 170                 175

Val Val Ala Ile Asp Leu Ala Gly Asp Glu Thr Ile Pro Gly Ser Ser
                180                 185                 190

Leu Leu Pro Gly His Val Gln Ala Tyr Gln Glu Ala Val Lys Ser Gly
            195                 200                 205

Ile His Arg Thr Val His Ala Gly Glu Val Gly Ser Ala Glu Val Val
210                 215                 220

Lys Glu Ala Val Asp Ile Leu Lys Thr Glu Arg Leu Gly His Gly Tyr
225                 230                 235                 240

His Thr Leu Glu Asp Gln Ala Leu Tyr Asn Arg Leu Arg Gln Glu Asn
                245                 250                 255

Met His Phe Glu Ile Cys Pro Trp Ser Ser Tyr Leu Thr Gly Ala Trp
                260                 265                 270

Lys Pro Asp Thr Glu His Ala Val Ile Arg Leu Lys Asn Asp Gln Ala
            275                 280                 285

Asn Tyr Ser Leu Asn Thr Asp Asp Pro Leu Ile Phe Lys Ser Thr Leu
290                 295                 300

Asp Thr Asp Tyr Gln Met Thr Lys Arg Asp Met Gly Phe Thr Glu Glu
305                 310                 315                 320

Glu Phe Lys Arg Leu Asn Ile Asn Ala Ala Lys Ser Ser Phe Leu Pro
                325                 330                 335

Glu Asp Glu Lys Arg Glu Leu Leu Asp Leu Leu Tyr Lys Ala Tyr Gly
            340                 345                 350

Met Pro Pro Ser Ala Ser Ala Gly Gln Asn Leu
        355                 360

<210> SEQ ID NO 3
<211> LENGTH: 1056
<212> TYPE: DNA
<213> ORGANISM: Mus musculus

<400> SEQUENCE: 3
atggcgcaaa cccggcgtt caataaaccg aaagtggagc tgcacgttca tctggacggc    60
gcgattaaac cggagaccat tctgtatttc ggtaagaaac gtggtattgc gctgccggcg   120
gacaccgtgg aggaactgcg taacatcatt ggcatggata agccgctgag cctgccgggt   180
ttcctggcga atttgacta ctatatgccg tgattgcgg gctgccgtga agcgatcaag     240
cgtattgcgt acgaatttgt tgagatgaag gcgaaagaag gtgtggttta cgttgaggtg   300
cgctatagcc cgcaccctgct ggcgaacagc aaagttgatc cgatgccgtg aaccaaacc   360 gagggtgatg tgaccccgga tgatgtggtt gatctggtta ccagggtct gcaagaaggc   420 gagcaggcgt tcggtatcaa agtgcgtagc attctgtgct gcatgcgtca ccaaccgagc   480
tggagcctgg aagttctgga gctgtgcaag aaatacaacc agaaaaccgt ggttgcgatg   540
gacctggcgg gtgatgaaac catcgagggc agcagcctgt tccgggtca cgtggaagcg   600 tatgagggtg cggttaagaa cggcattcac cgtaccgtgc atgcgggtga agttggcagc   660
ccggaagtgt tcgtgaggc ggtggacatc ctgaaaaccg agcgtgttgg tcacggctac   720
cacaccattg aagatgaggc gctgtataac cgtctgctga aggaaaacat gcacttcgag   780
```

```
gtgtgcccgt ggagcagcta tctgaccggt gcgtgggacc cgaaaaccac ccacgcggtg      840
gttcgtttca agaacgataa agcgaactac agcctgaaca ccgacgatcc gctgatcttt      900
aagagcaccc tggacaccga ttatcagatg accaagaaag acatgggttt caccgaggaa      960
gagtttaagc gtctgaacat taacgcggcg aaaagcagct ttctgccgga agaggagaag     1020
aaggaactgc tggaacgcct gtatcgtgag tatcag                               1056
```

<210> SEQ ID NO 4
<211> LENGTH: 352
<212> TYPE: PRT
<213> ORGANISM: Mus musculus

<400> SEQUENCE: 4

```
Met Ala Gln Thr Pro Ala Phe Asn Lys Pro Lys Val Glu Leu His Val
1               5                   10                  15

His Leu Asp Gly Ala Ile Lys Pro Glu Thr Ile Leu Tyr Phe Gly Lys
            20                  25                  30

Lys Arg Gly Ile Ala Leu Pro Ala Asp Thr Val Glu Glu Leu Arg Asn
        35                  40                  45

Ile Ile Gly Met Asp Lys Pro Leu Ser Leu Pro Gly Phe Leu Ala Lys
    50                  55                  60

Phe Asp Tyr Tyr Met Pro Val Ile Ala Gly Cys Arg Glu Ala Ile Lys
65                  70                  75                  80

Arg Ile Ala Tyr Glu Phe Val Glu Met Lys Ala Lys Glu Gly Val Val
                85                  90                  95

Tyr Val Glu Val Arg Tyr Ser Pro His Leu Leu Ala Asn Ser Lys Val
            100                 105                 110

Asp Pro Met Pro Trp Asn Gln Thr Glu Gly Asp Val Thr Pro Asp Asp
        115                 120                 125

Val Val Asp Leu Val Asn Gln Gly Leu Gln Glu Gly Glu Gln Ala Phe
    130                 135                 140

Gly Ile Lys Val Arg Ser Ile Leu Cys Cys Met Arg His Gln Pro Ser
145                 150                 155                 160

Trp Ser Leu Glu Val Leu Glu Leu Cys Lys Lys Tyr Asn Gln Lys Thr
                165                 170                 175

Val Val Ala Met Asp Leu Ala Gly Asp Glu Thr Ile Glu Gly Ser Ser
            180                 185                 190

Leu Phe Pro Gly His Val Glu Ala Tyr Glu Gly Ala Val Lys Asn Gly
        195                 200                 205

Ile His Arg Thr Val His Ala Gly Glu Val Gly Ser Pro Glu Val Val
    210                 215                 220

Arg Glu Ala Val Asp Ile Leu Lys Thr Glu Arg Val Gly His Gly Tyr
225                 230                 235                 240

His Thr Ile Glu Asp Glu Ala Leu Tyr Asn Arg Leu Leu Lys Glu Asn
                245                 250                 255

Met His Phe Glu Val Cys Pro Trp Ser Ser Tyr Leu Thr Gly Ala Trp
            260                 265                 270

Asp Pro Lys Thr Thr His Ala Val Val Arg Phe Lys Asn Asp Lys Ala
        275                 280                 285

Asn Tyr Ser Leu Asn Thr Asp Asp Pro Leu Ile Phe Lys Ser Thr Leu
    290                 295                 300

Asp Thr Asp Tyr Gln Met Thr Lys Lys Asp Met Gly Phe Thr Glu Glu
305                 310                 315                 320
```

Glu Phe Lys Arg Leu Asn Ile Asn Ala Ala Lys Ser Ser Phe Leu Pro
                325                 330                 335

Glu Glu Glu Lys Lys Glu Leu Leu Glu Arg Leu Tyr Arg Glu Tyr Gln
            340                 345                 350

<210> SEQ ID NO 5
<211> LENGTH: 369
<212> TYPE: PRT
<213> ORGANISM: Artificial Sequence
<220> FEATURE:
<223> OTHER INFORMATION: Plasmid Construct

<400> SEQUENCE: 5

Met Asp Trp Thr Trp Ile Leu Phe Leu Val Ala Ala Thr Arg Val
1               5                   10                  15

His Ser Ala Gln Thr Pro Ala Phe Asn Lys Pro Lys Val Glu Leu His
                20                  25                  30

Val His Leu Asp Gly Ala Ile Lys Pro Glu Thr Ile Leu Tyr Phe Gly
            35                  40                  45

Lys Lys Arg Gly Ile Ala Leu Pro Ala Asp Thr Val Glu Glu Leu Arg
        50                  55                  60

Asn Ile Ile Gly Met Asp Lys Pro Leu Ser Leu Pro Gly Phe Leu Ala
65                  70                  75                  80

Lys Phe Asp Tyr Tyr Met Pro Val Ile Ala Gly Cys Arg Glu Ala Ile
                85                  90                  95

Lys Arg Ile Ala Tyr Glu Phe Val Glu Met Lys Ala Lys Glu Gly Val
            100                 105                 110

Val Tyr Val Glu Val Arg Tyr Ser Pro His Leu Leu Ala Asn Ser Lys
        115                 120                 125

Val Asp Pro Met Pro Trp Asn Gln Thr Glu Gly Asp Val Thr Pro Asp
130                 135                 140

Asp Val Val Asp Leu Val Asn Gln Gly Leu Gln Glu Gly Glu Gln Ala
145                 150                 155                 160

Phe Gly Ile Lys Val Arg Ser Ile Leu Cys Cys Met Arg His Gln Pro
                165                 170                 175

Ser Trp Ser Leu Glu Val Leu Glu Leu Cys Lys Lys Tyr Asn Gln Lys
            180                 185                 190

Thr Val Val Ala Met Asp Leu Ala Gly Asp Glu Thr Ile Glu Gly Ser
        195                 200                 205

Ser Leu Phe Pro Gly His Val Glu Ala Tyr Glu Gly Ala Val Lys Asn
210                 215                 220

Gly Ile His Arg Thr Val His Ala Gly Glu Val Gly Ser Pro Glu Val
225                 230                 235                 240

Val Arg Glu Ala Val Asp Ile Leu Lys Thr Glu Arg Val Gly His Gly
                245                 250                 255

Tyr His Thr Ile Glu Asp Glu Ala Leu Tyr Asn Arg Leu Leu Lys Glu
            260                 265                 270

Asn Met His Phe Glu Val Cys Pro Trp Ser Ser Tyr Leu Thr Gly Ala
        275                 280                 285

Trp Asp Pro Lys Thr Thr His Ala Val Val Arg Phe Lys Asn Asp Lys
290                 295                 300

Ala Asn Tyr Ser Leu Asn Thr Asp Asp Pro Leu Ile Phe Lys Ser Thr
305                 310                 315                 320

Leu Asp Thr Asp Tyr Gln Met Thr Lys Lys Asp Met Gly Phe Thr Glu
                325                 330                 335

```
Glu Glu Phe Lys Arg Leu Asn Ile Asn Ala Ala Lys Ser Ser Phe Leu
            340                 345                 350

Pro Glu Glu Lys Lys Glu Leu Leu Glu Arg Leu Tyr Arg Glu Tyr
        355                 360                 365

Gln

<210> SEQ ID NO 6
<211> LENGTH: 352
<212> TYPE: PRT
<213> ORGANISM: Mus musculus

<400> SEQUENCE: 6

Met Ala Gln Thr Pro Ala Phe Asn Lys Pro Lys Val Glu Leu His Val
1               5                   10                  15

His Leu Asp Gly Ala Ile Lys Pro Glu Thr Ile Leu Tyr Phe Gly Lys
            20                  25                  30

Lys Arg Gly Ile Ala Leu Pro Ala Asp Thr Val Glu Glu Leu Arg Asn
        35                  40                  45

Ile Ile Gly Met Asp Lys Pro Leu Ser Leu Pro Gly Phe Leu Ala Lys
    50                  55                  60

Phe Asp Tyr Tyr Met Pro Val Ile Ala Gly Cys Arg Glu Ala Ile Lys
65                  70                  75                  80

Arg Ile Ala Tyr Glu Phe Val Glu Met Lys Ala Lys Glu Gly Val Val
                85                  90                  95

Tyr Val Glu Val Arg Tyr Ser Pro His Leu Leu Ala Asn Ser Lys Val
            100                 105                 110

Asp Pro Met Pro Trp Asn Gln Thr Glu Gly Asp Val Thr Pro Asp Asp
        115                 120                 125

Val Val Asp Leu Val Asn Gln Gly Leu Gln Glu Gly Glu Gln Ala Phe
    130                 135                 140

Gly Ile Lys Val Arg Ser Ile Leu Cys Cys Met Arg His Gln Pro Ser
145                 150                 155                 160

Trp Ser Leu Glu Val Leu Glu Leu Cys Lys Lys Tyr Asn Gln Lys Thr
                165                 170                 175

Val Val Ala Met Asp Leu Ala Gly Asp Glu Thr Ile Glu Gly Ser Ser
            180                 185                 190

Leu Phe Pro Gly His Val Glu Ala Tyr Glu Gly Ala Val Lys Asn Gly
        195                 200                 205

Ile His Arg Thr Val His Ala Gly Glu Val Gly Ser Pro Glu Val Val
    210                 215                 220

Arg Glu Ala Val Asp Ile Leu Lys Thr Glu Arg Val Gly His Gly Tyr
225                 230                 235                 240

His Thr Ile Glu Asp Glu Ala Leu Tyr Asn Arg Leu Leu Lys Glu Asn
                245                 250                 255

Met His Phe Glu Val Cys Pro Trp Ser Ser Tyr Leu Thr Gly Ala Trp
            260                 265                 270

Asp Pro Lys Thr Thr His Ala Val Val Arg Phe Lys Asn Asp Lys Ala
        275                 280                 285

Asn Tyr Ser Leu Asn Thr Asp Asp Pro Leu Ile Phe Lys Ser Thr Leu
    290                 295                 300

Asp Thr Asp Tyr Gln Met Thr Lys Lys Asp Met Gly Phe Thr Glu Glu
305                 310                 315                 320

Glu Phe Lys Arg Leu Asn Ile Asn Ala Ala Lys Ser Ser Phe Leu Pro
                325                 330                 335
```

Glu Glu Glu Lys Lys Glu Leu Leu Glu Arg Leu Tyr Arg Glu Tyr Gln
            340                 345                 350

<210> SEQ ID NO 7
<211> LENGTH: 352
<212> TYPE: PRT
<213> ORGANISM: Mus musculus

<400> SEQUENCE: 7

Met Ala Gln Thr Pro Ala Phe Asn Lys Pro Lys Val Glu Leu His Val
1               5                   10                  15

His Leu Asp Gly Ala Ile Lys Pro Glu Thr Ile Leu Tyr Phe Gly Lys
            20                  25                  30

Lys Arg Gly Ile Ala Leu Pro Ala Asp Thr Val Glu Glu Leu Arg Asn
        35                  40                  45

Ile Ile Gly Met Asp Lys Pro Leu Ser Leu Pro Gly Phe Leu Ala Lys
    50                  55                  60

Phe Asp Tyr Tyr Met Pro Val Ile Ala Gly Cys Arg Glu Ala Ile Lys
65                  70                  75                  80

Arg Ile Ala Tyr Glu Phe Val Glu Met Lys Ala Lys Glu Gly Val Val
                85                  90                  95

Tyr Val Glu Val Arg Tyr Ser Pro His Leu Leu Ala Asn Ser Lys Val
            100                 105                 110

Asp Pro Met Pro Trp Asn Gln Thr Glu Gly Asp Val Thr Pro Asp Asp
        115                 120                 125

Val Val Asp Leu Val Asn Gln Gly Leu Gln Glu Gly Glu Gln Ala Phe
    130                 135                 140

Gly Ile Lys Val Arg Ser Ile Leu Cys Cys Met Arg His Gln Pro Ser
145                 150                 155                 160

Trp Ser Leu Glu Val Leu Glu Leu Cys Lys Lys Tyr Asn Gln Lys Thr
                165                 170                 175

Val Val Ala Met Asp Leu Ala Gly Asp Glu Thr Ile Glu Gly Ser Ser
            180                 185                 190

Leu Phe Pro Gly His Val Glu Ala Tyr Glu Gly Ala Val Lys Asn Gly
        195                 200                 205

Ile His Arg Thr Val His Ala Gly Asp Val Gly Ser Pro Glu Val Val
    210                 215                 220

Arg Glu Ala Val Asp Ile Leu Lys Thr Glu Arg Val Gly His Gly Tyr
225                 230                 235                 240

His Thr Ile Glu Asp Glu Ala Leu Tyr Asn Arg Leu Leu Lys Glu Asn
                245                 250                 255

Met His Phe Glu Val Cys Pro Trp Ser Ser Tyr Leu Thr Gly Ala Trp
            260                 265                 270

Asp Pro Lys Thr Thr His Ala Val Val Arg Phe Lys Asn Asp Lys Ala
        275                 280                 285

Asn Tyr Ser Leu Asn Thr Asp Asp Pro Leu Ile Phe Lys Ser Thr Leu
    290                 295                 300

Asp Thr Asp Tyr Gln Met Thr Lys Lys Asp Met Gly Phe Thr Glu Glu
305                 310                 315                 320

Glu Phe Lys Arg Leu Asn Ile Asn Ala Ala Lys Ser Ser Phe Leu Pro
                325                 330                 335

Glu Glu Glu Lys Lys Glu Leu Leu Glu Arg Leu Tyr Arg Glu Tyr Gln
            340                 345                 350

<210> SEQ ID NO 8

```
<211> LENGTH: 380
<212> TYPE: PRT
<213> ORGANISM: Artificial Sequence
<220> FEATURE:
<223> OTHER INFORMATION: IgE-hADA-1

<400> SEQUENCE: 8

Met Asp Trp Thr Trp Ile Leu Phe Leu Val Ala Ala Thr Arg Val
1               5                   10                  15

His Ser Ala Gln Thr Pro Ala Phe Asp Lys Pro Lys Val Glu Leu His
                20                  25                  30

Val His Leu Asp Gly Ser Ile Lys Pro Glu Thr Ile Leu Tyr Tyr Gly
            35                  40                  45

Arg Arg Arg Gly Ile Ala Leu Pro Ala Asn Thr Ala Glu Gly Leu Leu
    50                  55                  60

Asn Val Ile Gly Met Asp Lys Pro Leu Thr Leu Pro Asp Phe Leu Ala
65                  70                  75                  80

Lys Phe Asp Tyr Tyr Met Pro Ala Ile Ala Gly Cys Arg Glu Ala Ile
                85                  90                  95

Lys Arg Ile Ala Tyr Glu Phe Val Glu Met Lys Ala Lys Glu Gly Val
                100                 105                 110

Val Tyr Val Glu Val Arg Tyr Ser Pro His Leu Leu Ala Asn Ser Lys
            115                 120                 125

Val Glu Pro Ile Pro Trp Asn Gln Ala Glu Gly Asp Leu Thr Pro Asp
130                 135                 140

Glu Val Val Ala Leu Val Gly Gln Gly Leu Gln Glu Gly Glu Arg Asp
145                 150                 155                 160

Phe Gly Val Lys Ala Arg Ser Ile Leu Cys Cys Met Arg His Gln Pro
                165                 170                 175

Asn Trp Ser Pro Lys Val Val Glu Leu Cys Lys Lys Tyr Gln Gln Gln
                180                 185                 190

Thr Val Val Ala Ile Asp Leu Ala Gly Asp Glu Thr Ile Pro Gly Ser
            195                 200                 205

Ser Leu Leu Pro Gly His Val Gln Ala Tyr Gln Glu Ala Val Lys Ser
210                 215                 220

Gly Ile His Arg Thr Val His Ala Gly Glu Val Gly Ser Ala Glu Val
225                 230                 235                 240

Val Lys Glu Ala Val Asp Ile Leu Lys Thr Glu Arg Leu Gly His Gly
                245                 250                 255

Tyr His Thr Leu Glu Asp Gln Ala Leu Tyr Asn Arg Leu Arg Gln Glu
                260                 265                 270

Asn Met His Phe Glu Ile Cys Pro Trp Ser Ser Tyr Leu Thr Gly Ala
            275                 280                 285

Trp Lys Pro Asp Thr Glu His Ala Val Ile Arg Leu Lys Asn Asp Gln
290                 295                 300

Ala Asn Tyr Ser Leu Asn Thr Asp Asp Pro Leu Ile Phe Lys Ser Thr
305                 310                 315                 320

Leu Asp Thr Asp Tyr Gln Met Thr Lys Arg Asp Met Gly Phe Thr Glu
                325                 330                 335

Glu Glu Phe Lys Arg Leu Asn Ile Asn Ala Ala Lys Ser Ser Phe Leu
                340                 345                 350

Pro Glu Asp Glu Lys Arg Glu Leu Leu Asp Leu Leu Tyr Lys Ala Tyr
            355                 360                 365

Gly Met Pro Pro Ser Ala Ser Ala Gly Gln Asn Leu
    370                 375                 380
```

<210> SEQ ID NO 9
<211> LENGTH: 2999
<212> TYPE: DNA
<213> ORGANISM: Artificial Sequence
<220> FEATURE:
<223> OTHER INFORMATION: Pvax vector sequence

<400> SEQUENCE: 9

```
gactcttcgc gatgtacggg ccagatatac gcgttgacat tgattattga ctagttatta      60
atagtaatca attacggggt cattagttca tagcccatat atggagttcc gcgttacata     120
acttacggta atggcccgc ctggctgacc gcccaacgac ccccgcccat tgacgtcaat      180
aatgacgtat gttcccatag taacgccaat agggactttc cattgacgtc aatgggtgga    240
ctatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccactag tccagtgtgg tggaattctg cagatatcca gcacagtggc    780
ggccgctcga gtctagaggg cccgtttaaa cccgctgatc agcctcgact gtgccttcta    840
gttgccagcc atctgttgtt tgcccctccc ccgtgccttc cttgaccctg gaaggtgcca    900
ctcccactgt cctttcctaa taaaatgagg aaattgcatc gcattgtctg agtaggtgtc    960
attctattct ggggggtggg gtggggcagg acagcaaggg ggaggattgg gaagacaata   1020
gcaggcatgc tggggatgcg gtgggctcta tggcttctac tgggcggttt tatggacagc   1080
aagcgaaccg gaattgccag ctggggcgcc ctctggtaag gttgggaagc cctgcaaagt   1140
aaactggatg gctttctcgc cgccaaggat ctgatgcgc aggggatcaa gctctgatca   1200
agagacagga tgaggatcgt ttcgcatgat tgaacaagat ggattgcacg caggttctcc   1260
ggccgcttgg gtgagaggc tattcggcta tgactgggca caacagacaa tcggctgctc   1320
tgatgccgcc gtgttccggc tgtcagcgca ggggcgcccg gttcttttg tcaagaccga   1380
cctgtccggt gccctgaatg aactgcaaga cgaggcagcg cggctatcgt ggctggccac   1440
gacgggcgtt ccttgcgcag ctgtgctcga cgttgtcact gaagcgggaa gggactggct   1500
gctattgggc gaagtgccgg ggcaggatct cctgtcatct caccttgctc ctgccgagaa   1560
agtatccatc atggctgatg caatgcggcg gctgcatacg cttgatccgg ctacctgccc   1620
attcgaccac caagcgaaac atcgcatcga gcgagcacgt actcggatgg aagccggtct   1680
tgtcgatcag gatgatctgg acgaagagca tcaggggctc gcgccagccg aactgttcgc   1740
caggctcaag gcgagcatgc ccgacggcga ggatctcgtc gtgacccatg gcgatgcctg   1800
cttgccgaat atcatggtgg aaaatggccg cttttctgga ttcatcgact gtggccggct   1860
gggtgtggcg gaccgctatc aggacatagc gttggctacc cgtgatattg ctgaagagct   1920
tggcggcgaa tgggctgacc gcttcctcgt gctttacggt atcgccgctc ccgattcgca   1980
gcgcatcgcc ttctatcgcc ttcttgacga gttcttctga attattaacg cttacaattt   2040
```

```
cctgatgcgg tattttctcc ttacgcatct gtgcggtatt tcacaccgca tacaggtggc    2100
acttttcggg gaaatgtgcg cggaacccct atttgtttat ttttctaaat acattcaaat    2160
atgtatccgc tcatgagaca ataaccctga taaatgcttc aataatagca cgtgctaaaa    2220 cttcatttt aatttaaaag gatctaggtg aagatccttt ttgataatct catgaccaaa     2280
atcccttaac gtgagttttc gttccactga gcgtcagacc ccgtagaaaa gatcaaagga    2340
tcttcttgag atcctttttt tctgcgcgta atctgctgct tgcaaacaaa aaaaccaccg    2400
ctaccagcgg tggtttgttt gccggatcaa gagctaccaa ctcttttcc gaaggtaact     2460 ggcttcagca gagcgcagat accaaatact gtccttctag tgtagccgta gttaggccac    2520
cacttcaaga actctgtagc accgcctaca tacctcgctc tgctaatcct gttaccagtg    2580
gctgctgcca gtggcgataa gtcgtgtctt accgggttgg actcaagacg atagttaccg    2640
gataaggcgc agcggtcggg ctgaacgggg ggttcgtgca cacagcccag cttggagcga    2700
acgacctaca ccgaactgag atacctacag cgtgagctat gagaaagcgc cacgcttccc    2760
gaagggagaa aggcggacag gtatccggta agcggcaggg tcggaacagg agagcgcacg    2820
agggagcttc cagggggaaa cgcctggtat ctttatagtc ctgtcgggtt tcgccacctc    2880
tgacttgagc gtcgatttt gtgatgctcg tcagggggc ggagcctatg gaaaaacgcc      2940
agcaacgcgg ccttttacg gttcctgggc ttttgctggc cttttgctca catgttctt      2999
```

COMPOSITIONS AND METHODS EMPLOYING ADENOSINE DEAMINASE-1 (ADA-1) AS AN ADJUVANT

CROSS-REFERENCE TO RELATED APPLICATIONS

This application claims priority to U.S. Provisional application 63/108,642 filed Nov. 2, 2020, the entire contents being incorporated herein by reference as though set forth in full.

INCORPORATION-BY-REFERENCE OF MATERIAL SUBMITTED IN ELECTRONIC FORM

Incorporated herein by reference in its entirety is the sequence listing submitted via EFS-Web as a text file named DRX_ADA1_US_SEQLIST.txt, created Nov. 2, 2021, and having a size of 26 bytes.

FIELD OF THE INVENTION

This invention relates to compositions and methods incorporating Adenosine deaminase-1 (ADA-1) as an adjuvant.

BACKGROUND OF THE INVENTION

Adenosine deaminase-1 (ADA-1) is primarily responsible for regulating intra- and extracellular adenosine levels by deaminating adenosine to produce inosine. ADA-1 functions both enzymatically and extra-enzymatically to regulate immune function. It is estimated that approximately 15% of heritable severe-combined immunodeficiencies (SCID) have their etiology in ADA1 loss-of-function mutations[1]. These disorders are characterized by a stark reduction in the number of circulating lymphocytes. Death of these cells occurs via apoptosis following accumulation of detrimental adenosine products[2]. CD4+ T cells express CD26, an ADA-1 receptor, and it is proposed that ADA-1 may bridge the CD26 receptor on these cells and other ADA-1 receptors expressed on antigen-presenting cells, promoting the formation of an immunological synapse. Indeed, it has been demonstrated that ADA-1-pulsed dendritic cells (DCs) induce robust proliferation of CD4+ T cells in co-culture experiments, independent of ADA-1 enzymatic activity[2,3]. Furthermore, ADA) is critical to the $T_{FH}$ program, and addition of exogenous ADA-1 enhances the ability of less efficient pre-$T_{FH}$ to provide help to B cells[4].

ADA-1 is also able to directly affect DC maturation and immunogenicity. ADA-1 stimulation of human monocyte-derived DCs (mDCs) resulted in upregulation of surface costimulatory molecules (CD80, CD83, CD86 and CD40) on immature cells from healthy and HIV-infected individuals. ADA-1 also induced the production of pro-inflammatory cytokines/chemokines, including IL-12, IL-6 and TNF-α. These effects enhanced dendritic cell immunogenicity leading to increased CD4+ and CD8+ T cell proliferation[5]. Previous studies have shown that human mDCs are endowed with the ability to induce $T_{FH}$ differentiation as they can adopt a "pro-$T_{FH}$" phenotype and secrete or express $T_{FH}$-polarizing cytokines, chemokines, chemokine receptors and co-stimulatory ligands[6-9]. These include but are not limited to IL-6, IL-12, IL-23, and CXCR5. However, it remains to be proven if ADA-1-treated DCs can induce differentiation of naïve CD4+ T into $T_{FH}$ cells.

Induction of neutralizing antibodies (nAbs) against HIV-1, COVID-19, and other viruses and cancers is critical to the generation of a successful prophylactic vaccine. The development of nAbs occurs to some extent in many HIV patients however, these responses develop slowly, allowing for the evolution of viral escape mutants. Generating nAbs targeting the envelope (env) glycoprotein of the virus remains a challenge for vaccination. Recent research has shown that while native env protein trimer immunization elicited similar quantities of env-binding antibodies in non-human primates (NHPs), not all animals developed nAbs. Fine-needle aspiration of lymph nodes revealed that nAb development correlated with germinal center (GC) B cell magnitude and the quality of $T_{FH}$ responses[10]. In mice, immunization with native-like env trimers was unable to induce autologous tier-2 neutralizing antibody responses and epitope mapping revealed a mouse-bias toward non-neutralizing antibody lineages[11]. Therefore, there is a critical need to develop immunogens which display neutralizing epitopes as well as vaccine modalities that can enhance GC function in the context of immunization with HIV-1 env vaccine antigens. The ability to encode molecular adjuvants targeting specific immune pathways makes DNA a useful platform for such modifications.

What is needed are more effective vaccine compositions for HIV-1, COVID-19, and other viruses and cancers.

SUMMARY OF THE INVENTION

Adenosine deaminase-1 (ADA-1) is identified herein as a molecule that is able to enhance differentiation of $T_{FH}$ cells and thus should be useful as a novel adjuvant in vaccine development. ADA-1 was able to enhance $T_{FH}$ differentiation in vitro and in vivo. The results herein also show that ADA-1 was able to improve anti-HIV antibody response in mice by more than 10-fold in 12 mice tested. Thus ADA-1 is a good candidate for an adjuvant for many infectious diseases and cancers.

In one aspect, a polynucleotide encoding Adenosine deaminase-1 (ADA-1) is provided. In one embodiment, the polynucleotide includes the sequence of SEQ ID NO: 1, or a sequence sharing at least 90% identity therewith. In another embodiment, the polynucleotide includes the sequence of SEQ ID NO: 3, or a sequence sharing at least 90% identity therewith. In another embodiment, the polynucleotide encodes a fusion protein, said fusion protein comprising an IgE signal peptide and an ADA-1. In one embodiment, the fusion protein has the sequence of SEQ ID NO: 5 or a sequence sharing at least 95% identity therewith.

In another aspect, a vector is provided which includes a polynucleotide encoding ADA-1 or a fusion protein comprising ADA-1. In one embodiment, the vector is a plasmid. In one embodiment, the vector is a viral vector.

In another aspect, a fusion protein comprising an IgE signal peptide and an ADA-1 is provided. In one embodiment, the fusion protein has the sequence of SEQ ID NO: 5, or a sequence sharing at least 95% identity therewith.

In another aspect, a vaccine composition is provided. The composition includes a vector comprising a polynucleotide encoding ADA-1 as an adjuvant, and a pharmaceutically acceptable carrier.

In yet another aspect, a method of increasing vaccine response in a subject is provided. The method includes administering a polynucleotide, vector, fusion protein, or composition as described herein, in combination with a vaccine composition. In one embodiment, the vaccine composition is a COVID-19 vaccine. In another embodiment, the vaccine composition is an HIV-1 vaccine.

These and other advantages of the various embodiments described herein will be apparent from the following detailed description of the invention.

BRIEF DESCRIPTION OF THE DRAWINGS

FIG. 1A-1K. ADA-1 treatment promotes DC maturation and the secretion of pro-$T_{FH}$ cytokines. Myeloid dendritic cells (mDCs) differentiated in vitro from monocytes of healthy human PBMCs, were treated with 0.5 μg/ml LPS plus 40 ng/ml IFN-γ or 2.5 μM ADA-1 for 24 h, and compared to unstimulated cells as controls. mDCs were harvested and stained for surface HLA and costimulatory molecule expression and analyzed by flow cytometry. Values are shown as the frequencies of (FIG. 1A) CD40, (FIG. 1B) CD83, (FIG. 1C) CD86, (FIG. 1D) HLA-DR and (FIG. 1E) ICOS L expression in the live, CD3− CD19− CD11c+ mDC population. Results are expressed as mean±SEM of 2 independent experiments (n=10). Culture supernatants were collected 24 h post-stimulation and analyzed for the levels of pro-$T_{FH}$ cytokine/chemokine production. Levels of (FIG. 1F) IL-6 and (FIG. 1G) IL-12p70 were assessed by ELISA whereas levels of (FIG. 1H) IL-4, (FIG. 1I) IL-10, (FIG. 1J) IL-1β and (FIG. K) BCA-1/CXCL13 were assessed by the Luminex assay. Results are expressed as mean±SEM of 4 independent experiments (n=10) for (FIG. 1F) and (FIG. 1G), and as mean±SEM of 2 independent experiments (n=6) for (H-K). Each individual circle represents one individual subject. *P<0.05, P<0.01, *P<0.001, and ****P<0.0001 by one-way ANOVA FIG. 2A-2C. Co-immunization with pADA enhances GC formation. (FIG. 2A) female C57BL/6 mice were immunized thrice, separated by 2 weeks with either empty plasmid (pVAX), HIV envelope B consensus gp160-encoding plasmid (pEnvB), or co-immunized with pEnvB and pADA (+pADA). All immunizations was delivered via intramuscular injection, followed by electroporation using the Cellectra device (Inovio). (FIG. 2B) Frequency of $T_{FH}$ in spleens and (FIG. 2C) Popliteal and inguinal lymph nodes at day 7 post-$3^{rd}$ immunization.

(FIG. 5A) Mice were immunized three times with envelope C DNA alone (pCapC), pCapC with simultaneous administration of matched recombinant envelope in alum adjuvant (+rCapC), DNA plus molecular ADA (+pADA), or DNA plus molecular ADA and simultaneous protein in alum (+pADA+rCapC). All DNA was delivered intramuscularly with in vivo electroporation in the left tibialis. All protein was delivered intramuscularly in the right quadriceps. env-binding IgG was quantified in the serum of vaccinated animals by ELISA at days 3 (FIG. 5B), 6 (FIG. 5C), and 12 (FIG. 5D) post-$3^{rd}$ immunization. Each point represents the average of duplicate samples from an individual animal, bars represent the mean and SEM. *p<0.05, p<0.01, *p<0.001, ****p<0.0001 by one-way ANOVA. Data are representative of one experiment with n=5/group.

FIG. 6A-6F. pADA supports protein-mediated GC formation. Mice were immunized as in FIG. 5. $T_{FH}$ (FIG. 6A-FIG. 6C) and GC B (FIG. 6D-FIG. 6F) cell frequencies were determined in the right DLNs at days 3 (FIG. 6A, FIG. 6D), 6 (FIG. 6B, FIG. 6E), and 12 (FIG. 6C, FIG. 6F) post-$3^{rd}$ immunization. Each point represents an individual animal, bars represent the mean and SD. *p<0.05, p<0.01, *p<0.001, ****p<0.0001 by one-way ANOVA. Data are representative of one experiment with n=5/group.

(FIG. 10A) Gating Strategy for GC $T_{FH}$ and GC B. Representative conventional flow cytometry plots from mouse draining lymph node cells showing the hierarchical phenotype staining from singlet lymphocytes to GC $T_{FH}$ and (FIG. 10B) GC B cells (n=5 per group). (FIG. 10B) Myeloid dendritic cells (mDCs) differentiated in vitro from monocytes of healthy human PBMCs, were treated with 0.5 µg/ml LPS plus 40 ng/ml IFN-γ or 2.5 µM ADA-1 for 24 h, and compared to unstimulated cells as controls. Harvested and stained mDCs were analyzed by flow cytometry for their expression of surface CD14, HLA-DR, CD40, CD83, CD86 and ICOS L. After gating out dead cells and removing doublets, the myeloid dendritic cell population was defined as Vivid⁻ Annexin V⁻ CD3⁻ CD19⁻ CD11c⁺ and expressed very low or no CD14.

FIG. 12A-12D. Addition of molecular ADA and enhances splenic GC B frequency in a DNA-protein co-immunization regimen. Mice were immunized as in FIG. 5. $T_{FH}$ (FIG. 12A, FIG. 12C) and GC B (FIG. 12B, FIG. 12D) cell frequencies were determined in the spleens at days 6 (FIG. 12A-FIG. 12B), and 12 (FIG. 12C-FIG. 12D) post-$3^{rd}$ immunization. Each point represents an individual animal, bars represent the mean and error bars represent SD. *p<0.05, p<0.01, *p<0.001, ****p<0.0001 by one-way ANOVA. Data are representative of one experiment with n=5/group.

(FIG. 13A) 100 ng of transformation amplified plasmids were digested with BamH1 and EcoR1. Resulting products were run on 0.7% agarose gel alongside undigested products. Lane 1=undigested human pADA, lane 2=digested human pADA, lane 3=undigested mouse pADA, and lane 4=digested mouse pADA. M=marker. (FIG. 13B) ADA was detected in the supernatant and lysates from 293T cells transfected with human ADA (hADA) and mouse ADA (mADA) via western blot. Lane 1=empty, lane 2=human ADA-transfected cell supernatant, lane 3=human ADA-transfected cell lysate from 1 sample. lane 4=mouse ADA-transfected cell supernatant, lane 5=mouse ADA-transfected cell lysate from 1 sample. Lane 6=human ADA-transfected cell supernatant, lane 7=human ADA-transfected cell lysate from a replicate transfected well. Lane 8=mouse ADA-transfected cell supernatant, lane 9=mouse ADA-transfected cell lysate from a replicate transfected well. Lane 10 and 11=supernatant and lysate from GFP transfected wells. Lanes 12 and 13=supernatant and lysate from non-transfected wells. (FIG. 13C) Green fluorescent protein (GFP) transfected 293T cells.

FIG. 14A-14G. pADA co-immunization enhances SARS-CoV-2 RBD-specific serum IgG after a single immunization. (FIG. 14A) Mice were immunized twice with pS alone or co-immunized with pS and pADA (+pADA) and serum RBD-specific IgG was quantified at days 7 (FIG. 14B), 14 (FIG. 14C), 21 (FIG. 14D) post $1^{st}$ immunization and day 7 post $2^{nd}$ immunization (FIG. 14E). In a second cohort of mice, sera were collected at day 18 post-$1^{st}$ (FIG. 14F) or $2^{nd}$ (FIG. 14G) immunization (prior to challenge) and assayed for pseudoviral neutralization. Symbols represent the average of replicates for an individual animal. Bars represent the mean and SEM. * p<0.05, p<0.01, *p<0.01, ****p<0.0001 by Dunnett's multiple comparison test (ANOVA) or Kruskall-Wallis test (F,G). Data are representative of 2 independent experiments (B, D, E), 4 independent experiments (FIG. 14C), or 1 experiment (FIG. 14F, FIG. 14G) with n=5/group.

(FIG. 15C, FIG. 15D) In a second experiment, animals were immunized at either day 14-post 1 immunization (FIG. 15C, left) or day 60-post 1 immunization (FIG. 15C right and FIG. 15D) and lymph nodes were harvested to quantify RBD-binding memory B or OX40L+$T_{FH}$ cells via flow cytometry. In FIG. 15A and FIG. 15B each symbol represents the average of a replicate assays for a group of 5 animals and bars represent the SEM. In FIG. 15C and FIG. 15D each symbol represents a single animal and bars represent the SD. *p<0.05, p<0.01, **p<0.0001 by t-test (FIG. 15A) or Dunnett's multiple comparison test (FIG. 15C, FIG. 15D).

FIG. 16A-16D. pADA co-immunization enhances SARS-CoV-2 cellular immunity in vivo. Mice were immunized twice separated by four weeks with pS alone or co-immunized with pS and pADA (+pADA) and rested for 14 or 60 days. Isolated splenocytes were stimulated with overlapping spike peptides and CD8⁺ T cells (top) and CD4⁺ T cells (bottom) were assayed for intracellular IL-2 (FIG. 16A, FIG. 16C), and TNFα (FIG. 16B, FIG. 16D) secretion via flow cytometry. Each symbol represents a single animal and bars represent the SD. *p<0.05, p<0.01, *p<0.001 by Dunnett's multiple comparison test.

DETAILED DESCRIPTION OF THE INVENTION

Figure 1A:
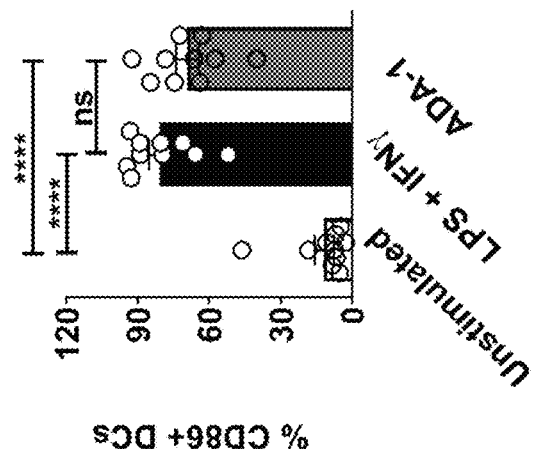

Provided herein are compositions and methods which employ adenosine deaminase-1 constructs, polynucleotides, and polypeptides as an adjuvant for use with various vaccines. ADA-1 fusion protein expression constructs have been developed for use in subjects in need thereof, including humans.

The inventors hypothesized that the co-delivery of plasmid-encoded ADA-1 (pADA) as a molecular adjuvant would improve the quality and quantity of immune responses to viral immunogens, including humoral immune responses to HIV-1 env DNA immunogens in a GC $T_{FH}$-dependent manner. In vitro, it was observed that treatment of human mDCs with ADA-1 induced maturation and resulted in a cytokine/chemokine secretion profile which likely supports $T_{FH}$ differentiation. In vivo, in the context of a consensus clade B HIV env DNA immunogen[12], a significant increase in the levels of HIV-binding IgG in the serum of mice co-immunized with pADA was observed. These responses correlated with increased frequencies of GC $T_{FH}$ in the draining lymph nodes (DLNs) of vaccinated animals. Increases in autoantibody in the serum of these vaccinated animals were undetectable, indicating that pADA-mediated enhancement of GC responses is antigen-specific. As heterologous DNA prime-protein boost and simultaneous DNA-protein vaccination regimens have shown the most promise for the development of anti-HIV immunity, the ability of pADA to enhance GC activities in the context of a DNA-protein co-immunization regimen was evaluated. Again, addition of molecular ADA-1 to the DNA arm of this regimen resulted in superior HIV-binding antibody production. Finally, addition of pADA to the DNA arm of this regimen resulted in the production of heterologous tier-1 nAbs in vaccinated mice. These data indicate that pADA co-immunization enhances antigen-specific IgG in the serum of vaccinated animals in a GC $T_{FH}$-dependent manner and does so without any enhancement of autoimmune antibodies. Thus, ADA-1 is a promising adjuvant that targets vaccine-induced GC responses.

Adenosine deaminase-1 (ADA1 or ADA-1) is an intracellular enzyme, as well as an ecto-enzyme (cell surface-bound), of the purine metabolism pathway. ADA-1 exerts its functions through both enzymatic and non-enzymatic mechanisms. The enzymatic function of ADA-1 is achieved by irreversible catabolism of adenosine or 2'-deoxyadenosine into inosine or 2'-deoxyinosine via deamination1. In humans, functional mutations of ADA-1 leads to early-onset severe combined immunodeficiency (SCID), which is characterized by the loss of functional T, B, and NK lymphocytes, impaired both cellular and humoral immunity, and an extreme susceptibility to repeated and persistent infections which are often caused by "opportunistic" organisms.

In one aspect, provided herein are engineered polynucleotides that encode murine or human adenosine deaminase-1. In the case of ADA-1, the native gene employs tandem rare codons that can reduce the efficiency of translation or even disengage the translational machinery. The inventors increased the codon usage bias in *E. coli* by upgrading the CAI to 0.96. GC content and unfavorable peaks have been optimized to prolong the half-life of the mRNA. The Stem-Loop structures, which impact ribosomal binding and stability of mRNA, were broken. In addition, the inventors screened and successfully modified negative cis-acting sites. Thus, provided herein, in one embodiment, is a polynucleotide encoding human ADA-1 comprising the sequence of SEQ ID NO: 1, or a sequence sharing at least 90% identity therewith. In another embodiment, a polynucleotide encoding murine ADA-1 comprising the sequence of SEQ ID NO: 3, or a sequence sharing at least 90% identity therewith is provided. In another embodiment, the polynucleotide shares at least 91%, 92%, 93%, 94%, 95%, 96%, 97%, 98%, or 99% identity with SEQ ID NO: 1. In yet another embodiment, the polynucleotide shares at least 91%, 92%, 93%, 94%, 95%, 96%, 97%, 98%, or 99% identity with SEQ ID NO: 3.

In another aspect, an ADA-1 fusion protein is provided. In one embodiment, the fusion protein comprises an IgE signal sequence in combination with an ADA-1 polypeptide. In one embodiment, the fusion protein comprises the sequence of SEQ ID NO: 5, or a sequence sharing at least 90% identity therewith. In another embodiment, the fusion protein comprises the sequence of SEQ ID NO: 8, or a sequence sharing at least 90% identity therewith. In another embodiment, the fusion protein shares at least 91%, 92%, 93%, 94%, 95%, 96%, 97%, 98%, or 99% identity with SEQ ID NO: 5. In yet another embodiment, the fusion protein shares at least 91%, 92%, 93%, 94%, 95%, 96%, 97%, 98%, or 99% identity with SEQ ID NO: 8. In one embodiment, the fusion protein has the sequence of SEQ ID NO: 5 with a 234E41D substitution. In one embodiment, the fusion protein has the sequence of SEQ ID NO: 8 with a 234E41D substitution.

In another aspect, polynucleotides which encode the ADA-1 fusion proteins described herein, are provided. In one aspect, the polynucleotide comprises any sequence which encodes the polypeptide of SEQ ID NO: 5, or a sequence sharing at least 90%, 91%, 92%, 93%, 94%, 95%, 96%, 97%, 98%, or 99% identity therewith. In another embodiment, the polynucleotide comprises any sequence which encodes the polypeptide of SEQ ID NO: 8, or a sequence sharing at least 90%, 91%, 92%, 93%, 94%, 95%, 96%, 97%, 98%, or 99% identity therewith.

In another aspect, the nucleic acid sequences described herein may be engineered into any suitable vector. The term "vector" refers to a nucleic acid molecule into which a second nucleic acid molecule can be inserted for introduction into a host cell where it will be replicated, and in some cases expressed. In other words, a vector is capable of transporting a nucleic acid molecule to which it has been linked. Cloning vectors as well as expression vectors are contemplated by the term "vector", as used herein. Certain vectors are capable of autonomous replication in a host into which they are introduced (e.g., vectors having a bacterial origin of replication can replicate in bacteria). Other vectors can be integrated into the genome of a host upon introduction into the host cell, and thereby are replicated along with the host genome. Vectors according to the invention can be made by methods well known to the person skilled in the art.

In one embodiment, the vector is a plasmid suitable for use as, or in combination with, a DNA vaccine. In one embodiment, the vector is the pVAX1™ plasmid vector from Invitrogen. pVAX1™ is a 3.0 kb plasmid vector designed for use in the development of DNA vaccines. The pVAX vector sequence is shown in SEQ ID NO: 9. The vector was constructed to be consistent with the Food and Drug Administration (FDA) document, "Points to Consider on Plasmid DNA Vaccines for Preventive Infectious Disease Indications", published Dec. 22, 1996. Features of the vector allow high-copy number replication in *E. coli* and high-level transient expression of the protein of interest in most mammalian cells. The vector contains the following elements: human cytomegalovirus immediate-early (CMV) promoter for high-level expression in a wide range of mammalian cells; bovine growth hormone (BGH) polyadenylation signal for efficient transcription termination and polyadenylation of mRNA; and a kanamycin resistance gene for selection in *E. coli*. Other suitable plasmids are known in the art, and include pcDNA3.1. See, Gomez and Onate, Plasmid-Based DNA Vaccines, 10.5772/intechopen.76754, published Nov. 5, 2018, available from intechopen-com/books/plasmid/plasmid-based-dna-vaccines.

In another embodiment, the vector is a viral vector, such as an adenoviral (Ad) vector or adeno-associated viral (AAV) vector.

In addition to the coding sequences for ADA-1, the vector also includes conventional control elements necessary which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences may include, without limitation, a enhancer; transcription factor; transcription terminator, promoter; efficient RNA processing signals such as splicing and polyadenylation (polyA) signals; sequences that stabilize cytoplasmic mRNA, for example Woodchuck Hepatitis Virus (WHP) Posttranscriptional Regulatory Element (WPRE); sequences that enhance translation efficiency (i.e., Kozak consensus sequence); sequences that enhance protein stability; and when desired, sequences that enhance secretion of the encoded product.

The regulatory control elements typically contain a promoter sequence as part of the expression control sequences. Constitutive promoters, regulatable promoters [see, e.g., WO 2011/126808 and WO 2013/04943], tissue specific promoters, or a promoter responsive to physiologic cues may be used may be utilized in the vectors described herein. In one embodiment, the promoter is a CMV promoter.

Examples of constitutive promoters suitable for controlling expression of the therapeutic products include, but are not limited to chicken β-actin (CB) promoter, CB7 promoter, human cytomegalovirus (CMV) promoter, ubiquitin C promoter (UbC), the early and late promoters of simian virus 40 (SV40), U6 promoter, metallothionein promoters, EF1α promoter, ubiquitin promoter, hypoxanthine phosphoribosyl transferase (HPRT) promoter, dihydrofolate reductase (DHFR) promoter (Scharfmann et al., Proc. Natl. Acad. Sci. USA 88:4626-4630 (1991), adenosine deaminase promoter, phosphoglycerol kinase (PGK) promoter, pyruvate kinase promoter phosphoglycerol mutase promoter, the s-actin promoter (Lai et al., Proc. Natl. Acad. Sci. USA 86: 10006-10010 (1989)), the long terminal repeats (LTR) of Moloney Leukemia Virus and other retroviruses, the thymidine kinase promoter of Herpes Simplex Virus and other constitutive promoters known to those of skill in the art.

In one embodiment, the vector comprises one or more expression enhancers. In one embodiment, the vector contains two or more expression enhancers. These enhancers may be the same or may differ from one another. For example, an enhancer may include a CMV immediate early enhancer. This enhancer may be present in two copies which are located adjacent to one another. Alternatively, the dual copies of the enhancer may be separated by one or more sequences. In still another embodiment, the expression cassette further contains an intron, e.g., the chicken beta-actin intron. Other suitable introns include those known in the art, e.g., such as are described in WO 2011/126808. Examples of suitable polyA sequences include, e.g., rabbit binding globulin (rBG), SV40, SV50, bovine growth hormone (bGH), human growth hormone, and synthetic polyAs. Optionally, one or more sequences may be selected to stabilize mRNA. An example of such a sequence is a modified WPRE sequence, which may be engineered upstream of the polyA sequence and downstream of the coding sequence (see, e.g., M A Zanta-Boussif, et al, Gene Therapy (2009) 16: 605-619).

Vector Production

After recombinant plasmids are designed and constructed using known techniques, they are introduced into bacteria using electroporation (electric pulses) or chemical transformation (calcium chloride) methods. Transformed bacteria, usually *E. coli*, are cultured until reaching their logarithmic growth phase, allowing the production of multiple copies of the recombinant plasmid. Subsequently, the plasmids are extracted from these bacteria, avoiding contamination with lipopolysaccharide (LPS), a component of the *E. coli* outer membrane, which is pro-inflammatory and whose administration can produce adverse reactions in individuals vaccinated with this DNA. DNA concentrations obtained are adjusted in physiological saline or phosphate buffered saline (PBS) and stored for later administration. Methods of preparing plasmid-based vectors are known. See, e.g., pVAX1 manual, Invitrogen, available at assets.thermofisher-com/TFS-Assets/LSG/manuals/pvax1_man-pdf.

For use in producing a viral vector, the expression cassettes can be carried on any suitable vector, e.g., a plasmid, which is delivered to a packaging host cell. The plasmids useful in this invention may be engineered such that they are suitable for replication and packaging in vitro in prokaryotic cells, insect cells, mammalian cells, among others. Suitable transfection techniques and packaging host cells are known and/or can be readily designed by one of skill in the art. Methods of preparing AAV-based vectors are known. See, e.g., US Published Patent Application No. 2007/0036760 (Feb. 15, 2007), which is incorporated by reference herein.

Compositions and Uses

In another aspect, a composition is provided which includes one or more of the polynucleotides, fusion proteins, or vectors described herein. In one embodiment, the composition is a vaccine composition. In one embodiment, the composition is an adjuvant composition. An adjuvant is a component or composition that helps the body create a stronger immune response to a vaccine or other immunotherapy.

In one embodiment, the composition includes a vector comprising a polynucleotide encoding adenosine deaminase-1 (ADA-1) as an adjuvant. In one embodiment, the vector is a plasmid. In another embodiment, the vector is a viral vector.

In another embodiment, the composition comprises a polynucleotide that encodes an ADA-1 fusion protein comprising an IgE signal peptide and an ADA-1. In one embodiment, the ADA is a human ADA-1. In one embodiment, the ADA is a murine ADA-1. In one embodiment, the polynucleotide is SEQ ID NO: 1, or a sequence sharing at least 90% identity therewith. In yet another embodiment, the polynucleotide is SEQ ID NO: 3, or a sequence sharing at least 90% identity therewith. In another embodiment, the polynucleotide shares at least 91%, 92%, 93%, 94%, 95%, 96%, 97%, 98%, or 99% identity with SEQ ID NO: 1. In yet another embodiment, the polynucleotide shares at least 91%, 92%, 93%, 94%, 95%, 96%, 97%, 98%, or 99% identity with SEQ ID NO: 3. In one aspect, the polynucleotide comprises any sequence which encodes the polypeptide of SEQ ID NO: 5, or a sequence sharing at least 90%, 91%, 92%, 93%, 94%, 95%, 96%, 97%, 98%, or 99% identity with SEQ ID NO: 5. In another embodiment, the polynucleotide comprises any sequence which encodes the polypeptide of SEQ ID NO: 8, or a sequence sharing at least 90%, 91%, 92%, 93%, 94%, 95%, 96%, 97%, 98%, or 99% identity with SEQ ID NO: 8.

In one embodiment, the composition includes a pharmaceutically acceptable carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host. Delivery vehicles such as liposomes, nanocapsules, microparticles, microspheres, lipid particles, vesicles, and the like, may be used for the introduction of the compositions of the present invention into suitable host cells.

In one embodiment, a composition includes a final formulation suitable for delivery to a subject, e.g., is an aqueous liquid suspension buffered to a physiologically compatible pH and salt concentration. Optionally, one or more surfactants are present in the formulation. In another embodiment, the composition may be transported as a concentrate which is diluted for administration to a subject. In other embodiments, the composition may be lyophilized and reconstituted at the time of administration.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

The vectors are administered in sufficient amounts provide a therapeutic benefit without undue adverse effects, or with medically acceptable physiological effects, which can be determined by those skilled in the medical arts. In certain embodiments, the vectors are formulated for intravenous delivery. In certain embodiments, the vectors are formulated for intramuscular delivery. In certain embodiments, the vectors are formulated for delivery via intranasal delivery devices for targeted delivery to nasal and/or nasopharynx epithelial cells. Other conventional and pharmaceutically acceptable routes of administration include, but are not limited to, direct delivery to a desired organ (e.g., lung), oral inhalation, intrathecal, intratracheal, intraarterial, intraocular, intravenous, intramuscular, subcutaneous, intradermal, and other parenteral routes of administration.

Dosages of the viral vector will depend primarily on factors such as the condition being treated, the age, weight and health of the patient, and may thus vary among patients. For example, a therapeutically effective human dosage of a viral vector is generally in the range of from about 25 to about 1000 microliters to about 25 mL of aqueous suspending liquid containing doses of from about 0.1 mg to about 100 mg plasmid DNA. A therapeutically effective human dosage of a viral vector is generally in the range of from about 25 to about 1000 microliters to about 25 mL of aqueous suspending liquid containing doses of from about $10^9$ to $4 \times 10^{15}$ GC of vector.

The plasmid compositions can be formulated in dosage units to contain an amount of plasmid in the range of about 0.1 to about 100 mg plasmid DNA (to treat an average subject of 70 kg in body weight) including all integers or fractional amounts within the range, and preferably 0.1 to about 5 mg DNA for a human patient. In one embodiment, the dosage is about 0.1 mg plasmid DNA. In another embodiment, the dosage is about 0.5 mg plasmid DNA. In another embodiment, the dosage is about 0.75 mg plasmid DNA. In another embodiment, the dosage is about 1.0 mg plasmid DNA. In another embodiment, the dosage is about 1.5 mg plasmid DNA. In another embodiment, the dosage is about 2.0 mg plasmid DNA. In another embodiment, the dosage is about 2.5 mg plasmid DNA. In another embodiment, the dosage is about 3.0 mg plasmid DNA. In another embodiment, the dosage is about 3.5 mg plasmid DNA. In another embodiment, the dosage is about 4.0 mg plasmid DNA. In another embodiment, the dosage is about 4.5 mg plasmid DNA. In another embodiment, the dosage is about 5.0 mg plasmid DNA. In another embodiment, the dosage is about 5.5 mg plasmid DNA. In another embodiment, the dosage is about 6.0 mg plasmid DNA. In another embodiment, the dosage is about 6.5 mg plasmid DNA. In another embodiment, the dosage is about 7.0 mg plasmid DNA. In another embodiment, the dosage is about 7.5 mg plasmid DNA. In another embodiment, the dosage is about 8.0 mg plasmid DNA. In another embodiment, the dosage is about 8.5 mg plasmid DNA. In another embodiment, the dosage is about 9.0 mg plasmid DNA. In another embodiment, the dosage is about 9.5 mg plasmid DNA. In another embodiment, the dosage is about 10.0 mg plasmid DNA. In another embodiment, the dosage is about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg plasmid DNA.

The viral vector compositions can be formulated in dosage units to contain an amount of replication-defective virus that is in the range of about $10^9$ GC to about $10^{16}$ GC (to treat an average subject of 70 kg in body weight) including all integers or fractional amounts within the range, and preferably $10^{12}$ GC to $10^{14}$ GC for a human patient.

These above doses may be administered in a variety of volumes of carrier, excipient or buffer formulation, ranging from about 25 to about 1000 microliters, or higher volumes, including all numbers within the range, depending on the size of the area to be treated, the plasmid concentration or viral titer used, the route of administration, and the desired effect of the method. In one embodiment, the volume of carrier, excipient or buffer is at least about 25 µL. In one embodiment, the volume is about 50 µL. In another embodiment, the volume is about 75 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 225 µL. In yet another embodiment, the volume is about 250 µL. In yet another embodiment, the volume is about 275 µL. In yet another embodiment, the volume is about 300 µL. In yet another embodiment, the volume is about 325 µL. In another embodiment, the volume is about 350 µL. In another embodiment, the volume is about 375 µL. In another embodiment, the volume is about 400 µL. In another embodiment, the volume is about 450 µL. In another embodiment, the volume is about 500 µL. In another embodiment, the volume is about 550 µL. In another embodiment, the volume is about 600 µL. In another embodiment, the volume is about 650 µL. In another embodiment, the volume is about 700 µL. In another embodiment, the volume is between about 700 and 1000 µL.

Methods suitable for assessing the amount of ADA-1 in a sample using antibodies that bind to hADA-1 include those of Enzyme Linked Immunosorbent Assay (ELISA). Specifically, NOVUS Human Adenosine Deaminase/ADA ELISA Kit (Chemiluminescence) Kit, which can specifically detect human ADA in various samples such as serum, plasma and other biological fluids. The kit is utilized according to manufacturing instruction.

Methods of Use

In another aspect, a method of increasing vaccine response in a subject is provided. The method includes providing a composition comprising ADA-1 in combination with a vaccine composition. In one embodiment, the method includes administering the polynucleotide, vector, fusion protein, or composition as described herein. In one embodiment, the composition is administered intramuscularly.

In on embodiment, the subject is desirably a human. In another embodiment, the subject is an older adult, e.g., over the age of 40. In another embodiment, the subject is at least 45, 50, 55, or 60 years of age. In yet another embodiment, the subject is a senior adult, i.e., over 60 years of age.

The ADA-1 adjuvant compositions are useful with various vaccine compositions. In one embodiment, the vaccine composition is a DNA vaccine composition. In one embodiment, the vaccine composition is for COVID-19. In another embodiment, vaccine composition is for HIV-1.

The ADA-1 adjuvant composition may be administered prior to, concurrently with, or after a vaccine composition. In one embodiment, the ADA-1 composition and vaccine composition are administered approximately simultaneously.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length and may be up to about 700 amino acids. Examples of suitable fragments are described herein.

Generally, when referring to "identity", "homology", or "similarity" between two different nucleic acid or amino acids, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Examples of such programs include, "Clustal Omega", "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fast™, a program in GCG Version 6.1. Fast™ provides alignments and percent sequence identity of the regions of the best overlap between the query and search sequences. For instance, percent sequence identity between nucleic acid sequences can be determined using Fast™ with its default parameters (a word size of 6 and the NOPAM factor for the scoring matrix) as provided in GCG Version 6.1, herein incorporated by reference. Multiple sequence alignment programs are also available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, an "effective amount" refers to the amount of the ADA-1 composition which provides sufficient levels of ADA-1 to increase the immune response of a subject to a vaccine composition. An effective amount may be determined based on an animal model, rather than a human patient. Examples of a suitable murine model are described herein.

As described above, the term "about" when used to modify a numerical value means a variation of ±10%, unless otherwise specified.

As used throughout this specification and the claims, the terms "comprise" and "contain" and its variants including, "comprises", "comprising", "contains" and "containing", among other variants, is inclusive of other components, elements, integers, steps and the like. The term "consists of" or "consisting of" are exclusive of other components, elements, integers, steps and the like.

It is to be noted that the term "a" or "an", refers to one or more, for example, "an enhancer", is understood to represent one or more enhancer(s). As such, the terms "a" (or "an"), "one or more," and "at least one" is used interchangeably herein.

With regard to the description of these inventions, it is intended that each of the compositions herein described, is useful, in another embodiment, in the methods of the invention. In addition, it is also intended that each of the compositions herein described as useful in the methods, is, in another embodiment, itself an embodiment of the invention.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

EXAMPLES

Adenosine deaminase-1 (ADA-1) plays both enzymatic and non-enzymatic roles in regulating immune cell function. ADA-1 inhibits the accumulation of adenosine and elicits T cell proliferation. Mutations in the ADA) gene account for 15% of heritable severe-combined immunodeficiencies. We determined that ADA1 expression distinguishes and is instrumental for the germinal center follicular helper T cell ($T_{FH}$) program using in vitro human assays. Herein, we tested whether ADA-1 can be used as an adjuvant to improve vaccine efficacy in vivo.

$T_{FH}$ cells are ideal targets for HIV vaccines. $T_{FH}$ cells play a critical role in the generation of Broad neutralizing antibodies against HIV. These antibodies are able to neutralize a large number of primary HIV isolates and have been shown to be protective against HIV acquisition in NHP models and humans. All identified broad neutralizing antibodies are heavily mutated in a process which is orchestrated by $T_{FH}$ cells. Additionally, there is a positive association between frequency of circulating $T_{FH}$ cells and the presence of broad neutralizing antibodies. By orchestrating isotype switching. $T_{FH}$ cells impact the nature of antibody effector functions.

First, we studied the effect of ADA-1 on antigen presenting cells as a possible mechanism for enhancing immune responses. ADA-1 induced myeloid dendritic cell (mDC) maturation as measured by increased frequencies of CD40–, CD83–, CD86–, and HLA-DR-positive mDCs. ADA-1 treatment also promoted the secretion of the $T_{FH}$-polarizing cytokine IL-6 from mDCs. In the context of an HIV-1 envelope (env) DNA vaccine, co-immunization with plasmid-encoded ADA-1 (pADA) enhanced humoral immunity. Animals co-immunized with env DNA and pADA had significantly increased frequencies of $T_{FH}$ cells in their draining lymph nodes and increased HIV-binding IgG in serum.

Next, mice were co-immunized with subtype C env gp160 DNA and pADA along with simultaneous immunization with matched gp140 trimeric protein. Mice that received env gp160 DNA, pADA, and gp140 glycoprotein had significantly more heterologous HIV-specific binding IgG in their serum. Furthermore, only mice that received the combination ADA-1 adjuvanted vaccine had detectable neutralizing antibody responses. These studies indicate that ADA-1 can be used as a vaccine adjuvant to qualitatively enhance germinal center responses, and represent a novel application of an existing therapeutic agent that can be quickly translated for clinical use.

The following examples are illustrative only and are not a limitation on the invention described herein.

Example 1: Adenosine Deaminase-1 Enhances Germinal Center Formation and Functional Antibody Responses to HIV-1 Envelope DNA and Protein Vaccines Materials and Methods DNA plasmid preparation. DNA vaccine constructs expressing HIV-1 consensus EnvA, EnvB, and EnvC were generated by Inovio Pharmaceuticals (Bluebell, PA) and have been previously reported[13, 59, 60]. Murine adenosine deaminase-1 (Gene Bank accession number NM001272052) was cloned into the pVAX vector (Invitrogen) and amplified by Genescript (Piscataway, NJ). Expression of the construct was confirmed in-house via lipofectamine (Invitrogen) transfection of 293T cells and western blot for expression of mouse ADA-1. Plasmid constructs expressing subtype C Env gp160 from subject CAP257 were kindly provided by Penny Moore and collaborators working with the CAPRISA cohort, as described[39]. The CAP257 54 week env gene sequence (CAP257 54wk_D) was motif-optimized using the Robins-Krasnitz methodology and cloned as gp160 into pEMC*. Plasmid DNA was purified using Endo-free reagents (Qiagen, Valencia, CA). Expression of full length gp160 in vitro was verified by immunofluorescence surface staining of transfected cells using the human mAb b12 and by complementation of env-negative HIV genomes to produce HIV pseudovirus expressing the Env-CAP257-54wk_D.

Protein production. The gp140 DNA was derived from the gp160 envelope 54wk_D sequence by site-directed mutagenesis (QuickChange Multi Site-Directed Mutagenesis Kit, Stratagene, La Jolla, CA) to insert the previously described mutations[61] in the primary and secondary protease cleavage sites respectively: REKR was mutated to RSKS and KAKRR was mutated to KAISS. A large-scale endotoxin-free plasmid preparation (Qiagen, Valencia, CA) was used for stable expression in 293F cells for protein production[62]

Plasmid immunizations. 6- to 12-week-old male and female C57BL/6 (Charles River) mice were immunized thrice, 2 weeks apart, in the tibialis anterior muscle with either 50 μg of pVAX, 10 μg of HIV-1 antigenic plasmid (pEnvB), or 10 μg of EnvB with 20 μg of ADA-1 (pADA) (n=4-6 animals per group). The injection was followed by in vivo electroporation using the constant current Cellectra device (Inovio Pharmaceuticals, Blue Bell, PA).

Protein immunizations. 6- to 12-week-old female C57BL/6 mice were immunized thrice separated by two weeks in the right quadricepsfemoris with 30 μl containing 10 μg of purified gp140 (CAP257-54wk_D). Protein immunogen was formulated in aluminum phosphate (Adjuphos) adjuvant (Invivogen, San Diego, CA). All animals were housed in a temperature-controlled, light-cycled facility at the Drexel University animal care facility (accredited by the Association for Assessment and Accreditation of Laboratory Animal Care). Animal work was performed according to protocols approved by our Institutional Animal Care and Use Committee.

Mouse sacrifice, sample collection, and tissue harvest. At time points designated in the immunization schedule, the animals were sedated using avertin anesthetic (Vedco, St. Joseph, MI) prior to cardiac puncture and cervical dislocation. Blood, cecal contents, spleens, popliteal, and inguinal lymph nodes, were collected. The popliteal and inguinal lymph nodes (DLNs) and spleens from each mouse were collected in petri dishes containing 5 ml of ice-cold RPMI 1640 medium containing 10% FBS and 1% antibiotic/antimycotic (R10). Spleens were disrupted in sterile sample bags containing 5 ml of ice-cold RPMI 1640 using a Seward Stomacher (Seward, West Sussex, UK). DLNs were disrupted by crushing the tissues with a sterile syringe plunger. Splenocyte suspensions were pelleted and incubated for 5 min at room temperature in ACK lysing buffer (Thermo Fischer, Waltham, MA) to lyse red blood cells. The resulting single cell suspensions from DLNs and spleens were washed and resuspended in R10 medium. All cells were counted, and cell viability was determined using a Countess Automated Cell Counter (Invitrogen, Life Technologies). Blood was collected in minicollect serum gel tubes (Grenier-Bio) and centrifuged at 13,000 RPM for 30 min at 4° C. to separate serum.

Flow cytometry. Single cell suspension of lymphocytes harvested from the DLNs, and spleens were suspended in cold RPMI 1640 containing 10% FBS and stained with the live/dead Fixable Aqua Dead Cell Stain Kit (Invitrogen) (dilution: 1/100; Cat. Number: L34957) to exclude dead cells. All cytometric analyses were performed using an LSR II flow cytometer (BD), and data were analyzed using FlowJo software (Treestar). All B-cell analyses were performed after gating out dead, IgD$^+$, and CD3$^+$F4/80+Gr1$^+$ cells in the dump channel. $T_{FH}$ cells were stained with the following fluorochrome-conjugated anti-mouse antibodies: CD3 (17A2) (dilution: 1/100; Cat. Number: 100216), CD4 (GK1.5) (dilution: 1/200; Cat. Number: 100414), CD25 (PC61) (dilution: 1/100; Cat. Number: 102010), PD-1 (RMP1-30) (dilution: 1/100; Cat. Number: 109110), IgD (11-26c.2a) (dilution: 1/100; Cat. Number: 405742), B220 (RA3-6B2) (dilution: 1/100; Cat. Number: 103211), CD95 (SA367H8) (dilution: 1/100; Cat. Number: 152612), CD44 (IM7) (dilution: 1/100; Cat. Number: 103047), GL7 (GL7) (dilution 1/200; Cat. Number: 144610) were all from BioLegend. CXCR5 (2G8) (dilution: 1/20; Cat. Number: 560615) and CD62L (MEL-14) (dilution 1/100; Cat. Number: 564108), were from BD Biosciences.

Enzyme-linked immunosorbent assays. ELISA was used to determine HIV-1 EnvB-specific IgG and IgA in mouse serum. Mouse blood samples were collected by cardiac puncture. Enzyme immunoassay/radioimmunoassay plates (Costar) were coated with HIV-1 EnvA (UG37), EnvB (MNgp41), or EnvC (96Z) protein (NIH AIDS reagent repository) diluted in PBS at a concentration of 0.5 µg/ml in a final volume of 100 µl per well and incubated overnight at 4° C. Plates were washed with PBS/Tween-20 (0.05%) 3 times and blocked against nonspecific binding with 200 µl of 3% BSA and 0.1% Tween-20 in 1×PBS for 2 hours at room temperature. The plates were washed, and sera or fecal extract diluted in PBS/1% BSA containing protease inhibitor (Pierce) were added in triplicate at a final volume of 100 µl and incubated overnight at 4° C. Bound antibodies were detected with HRP-labeled goat anti-mouse IgG or IgA (KPL/Seracare, Gaithersburg, MD) and developed using TMB Ultra substrate (Thermo Fisher, Waltham, MA) according to the manufacturer's instructions. The amount of total IgG (or subtypes) or IgA in sera or fecal extract was calculated by interpolating the optical densities on calibration curves created with known quantities of mouse immunoglobulin. For fecal extract ELISA, values are reported as ng/ml immunoglobulin per gram of stool.

Detection of anti-nuclear antibody. Mouse anti-nuclear antibody (ANA) was detected in the serum from vaccinated animals using a commercially available ELISA kit from Express Biotech (Frederick, MD), according to the manufacturer's protocol. ANA in serum was also detected using a modified ANA/Hep-2 immunofluorescence assay (IFA) (Hemagen, Columbia, MD). Briefly, slides pre-coated with fixed Hep-2 cells expressing nuclear antigens were incubated with a 1:40 dilution of serum from vaccinated mice for 30 min at room temperature, followed by incubation with anti-mouse IgG FITC conjugate. Images were collected on a Leica DM500B microscope at 10× and 40× magnifications. Fluorescence intensity was graded blindly on a 0-4 scale according to the manufacturer's protocol.

Neutralization assays. The TZM-bl assay was performed as previously described[63] using purified mouse IgG (purified with Protein A). Recovery of IgG was determined by PAGE and Coomassie staining. All values were calculated with respect to virus only wells [(value for virus only minus cells only) minus (value for serum minus cells only)] divided by (value for virus minus cells only). The human monoclonal antibody VRC01, which is an IgG1, was used as a positive control. Viruses were grown as described as pseudoviruses and strains tested included HIV-SF162, HIV-MW965, and HIV-CAP257-54wk_D.

Human samples. Blood samples from healthy donors were obtained from the Martin Memorial Health System (Stuart, Florida) after signed informed consent from all participants. All procedures were performed according to the Institutional Review Boards of the Martin Memorial Health System and Drexel University College of Medicine.

Generation of human monocyte-derived dendritic cells (mDCs). Human PBMCs from healthy donors were obtained immediately after blood withdrawal using the Ficoll-Paque (GE Healthcare) gradient method and stored in liquid nitrogen until usage. The cells were thawed in RPMI 1640 (Corning) supplemented with 10% fetal bovine serum (Access Biologicals) and 1% penicillin/streptomycin (Gibco). CD14$^+$ CD16$^+$ monocytes were then enriched from total PBMCs by negative selection using the EasySep™ human monocyte enrichment kit without CD16 depletion (STEMCELL Technologies) according to the manufacturer's protocol and counted. Cells were then resuspended in serum-free CellGenix® GMP dendritic cell medium (CellGenix) with 100 ng/ml of recombinant human GM-CSF (BioLegend) and 20 ng/ml of recombinant human IL-4 (Gemini Bio-Products) at a density of 2×10$^6$ per ml in 24-well plates. After 48 h of incubation, cells were stimulated with 0.5 µg of LPS (Invivogen) plus 40 ng/ml of IFNγ (Gemini Bio-Products) or 2.5 µM of ADA-1 (Sigma Aldrich) in 1 ml medium and compared to the unstimulated control. Dendritic cells were harvested after 24 h of stimulation, and analyzed by flow cytometry.

Flow cytometric analysis of stimulated human mDCs. Harvested mDCs were incubated with TruStain FcγR block (BioLegend) and fluorochrome-conjugated antibodies for 15-20 minutes on ice in the dark. The following BioLegend fluorochrome-conjugated anti-human antibodies were used: CD3 (clone HIT3α), CD19 (clone HIB19), CD14 (clone M5E2), CD11c (clone 3.9), HLA-DR (clone L243), CD86 (clone IT2.2), CD83 (clone HB15e), CD40 (clone 5C3) and ICOS L (clone 2D3). Dead cells were identified using both LIVE/DEAD fixable Aqua Dead Cell Stain Kit for flow cytometry (Vivid) (Life Technologies) and Annexin V (BD Biosciences). mDC samples were washed then resuspended in PBS plus 2% FBS then acquired on a BD LSR II and analyzed with FlowJo software (Treestar). The gating strategy excluded doublet cells and mDCs were gated on live (Vivid$^-$ Annexin V$^-$) CD3$^-$CD19$^-$ CD11c$^+$ cells.

Analysis of cytokine level production by stimulated human mDCs using EISA. Cell culture supernatants were collected 24 h post-stimulation and were analyzed for the levels of IL-6 and IL-12p70, using the BioLegend human IL-6 and human IL-12p70 ELISA kits respectively, according to the manufacturer's protocol. Briefly, plates were coated overnight at 4° C. with 100 µl of the appropriate capture antibody (anti-IL-6 or anti-IL-12-p70) diluted 1:200 in coating buffer. Plates were then incubated with 200 µl of assay diluent for 1 h to avoid non-specific binding. A 100 µl of standards, samples and controls diluted in assay diluent, were subsequently added to the appropriate wells and incubated for 2 h. Standards were run in duplicates in a 2-fold serial dilution. A 100 µl of the appropriate biotinylated detection antibody was diluted 1:200 in assay diluent and then added to all wells for 1 h, followed by a 100 µl of Avidin-HRP diluted 1:1000 in assay buffer and incubated for 30 minutes. Plates were developed with a 100 µl of TMB substrate and incubated in the dark until the desired color was observed. The reaction was stopped with a 100 µl of stop solution added to each well. Plates were washed between each step to remove non-specific binding. All incubations were done on a shaker at room temperature (RT). Absorbance was read at 450 nm using a Synergy HTX multi-mode (BioTek) spectrophotometer within 15 minutes of stopping the reaction. Standard curves were generated and sample concentrations were calculated in pg/ml.

Analysis of cytokine/chemokine level production by stimulated human mDCs using the Luminex® assay. The Bio-Plex Pro Human Chemokine Assay (40-Plex) (Bio-Rad) was used to determine the level of a 40 cytokine/chemokine panel produced by mDCs, 24 h after stimulation. The following human chemokine/cytokine premixed panel was used according to the manufacturer's protocol: 6Ckine (CCL21), MIG (CXCL9), GCP-2 (CXCL6), IL-6, I-309 (CCL1), IFNγ, SDF-1α+β (CXCL12), I-TAC (CXCL11), MCP-3 (CCL7), IL-16, MCP-4 (CCL13), MDC (CCL22), Eotaxin-2 (CCL24), GM-CSF, MIF, TNF-α, MPIF-1 (CCL23), IL-2, IL-1β, Eotaxin-1 (CCL 11), TECK (CCL25), IL-4, MCP-1 (CCL2), IL-8, MIP-1α (CCL3), IL-10, MCP-2 (CCL8), Gro-α (CXCL1), MIP-3α (CCL20), SCYB16 (CXCL16), Eotaxin-3 (CCL26), MIP-1o (CCL15), TARC (CCL17), CTACK (CCL27), ENA-78 (CXCL5), BCA-1 (CXCL13), MIP-36 (CCL19), Fractalkine (CXC3CL1), Gro-B (CXCL2). Briefly, 50 µl of (1×) beads were vortexed and added to each well of the assay plate, then removed by plate washing. Fifty microliters of vortexed samples, standards, blank and controls were then loaded onto appropriate wells and incubated for 1 h. Standards were run in duplicates in a 4-fold serial dilution. Following that, 25 µl of (1×) detection antibodies were added to all wells and incubated for 30 minutes before the addition of 50 µl of (1×) streptavidin-PE for 10 minutes. Beads were resuspended in 125 µl assay buffer and plates shaken for 30 seconds. Plates were washed between each step to remove non-specific binding. All incubations were done on a shaker, at RT, protected from the light. Data was acquired on a Bio-Plex 200 System using beads regions defined in the protocol and analyzed with the Bio-Plex Manager 6.1 software (Bio-Rad). Standard curves were generated and sample concentrations were calculated in pg/ml.

Statistical analysis. All statistical analysis was performed using GraphPad Prism software version 6. Flow cytometry data were analyzed using Flowjo versions 7 or 10 (Treestar). All data are representative of at least two independent experiments except where noted. Data are presented as the mean±standard error of the mean or standard deviation as noted. Where appropriate, the statistical difference between immunization groups or treatment conditions was assessed using an ordinary one-way analysis of variance (ANOVA) (Tukey's multiple comparison test). Correlations were assessed using a Pearson correlation. *$p<0.05$, $p<0.01$, *$p<0.001$, ****$p<0.0001$.

Results

ADA-4 Induces the Maturation of Human mDCs

Figure 1B:
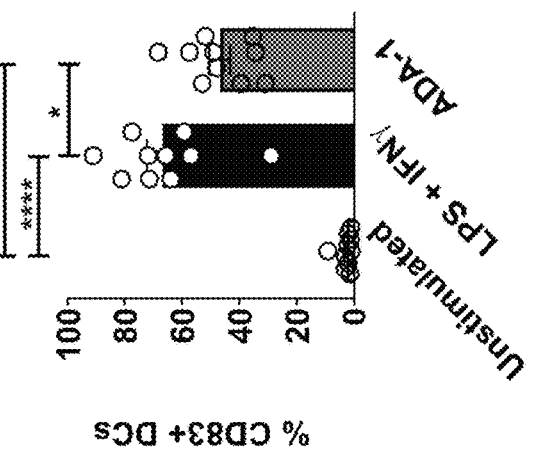
Figure 1C:
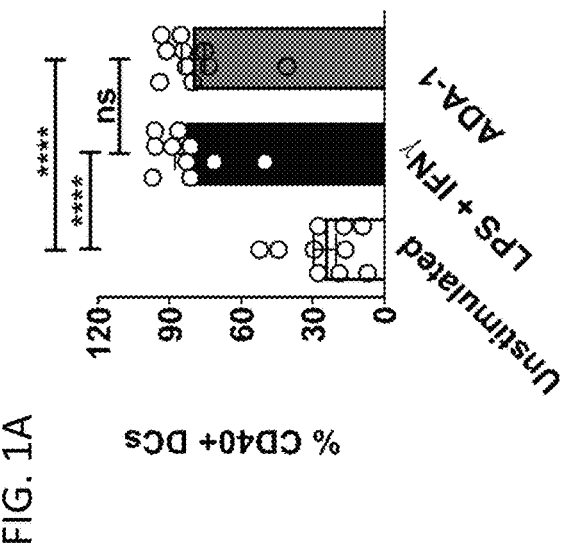
Figure 1D:
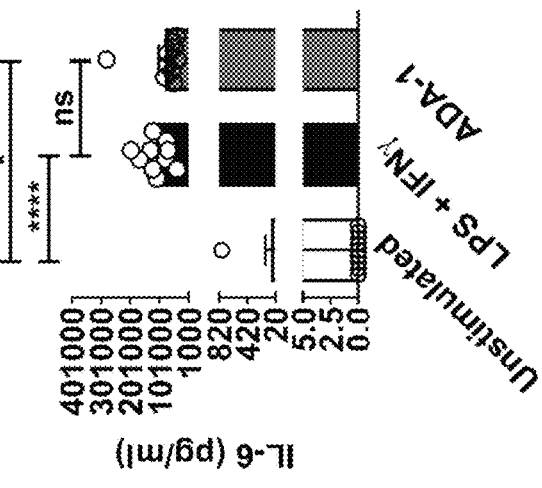
Figure 1E:
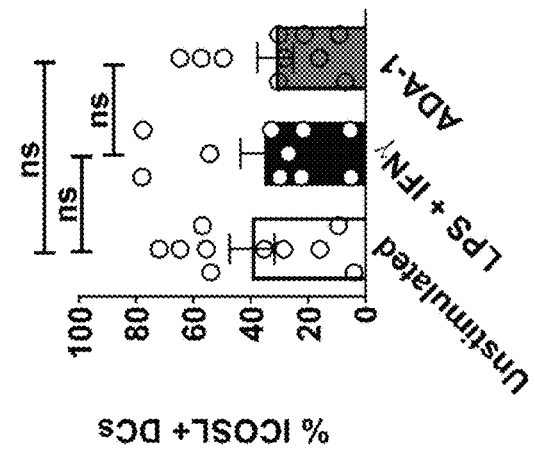
Figure 10A:
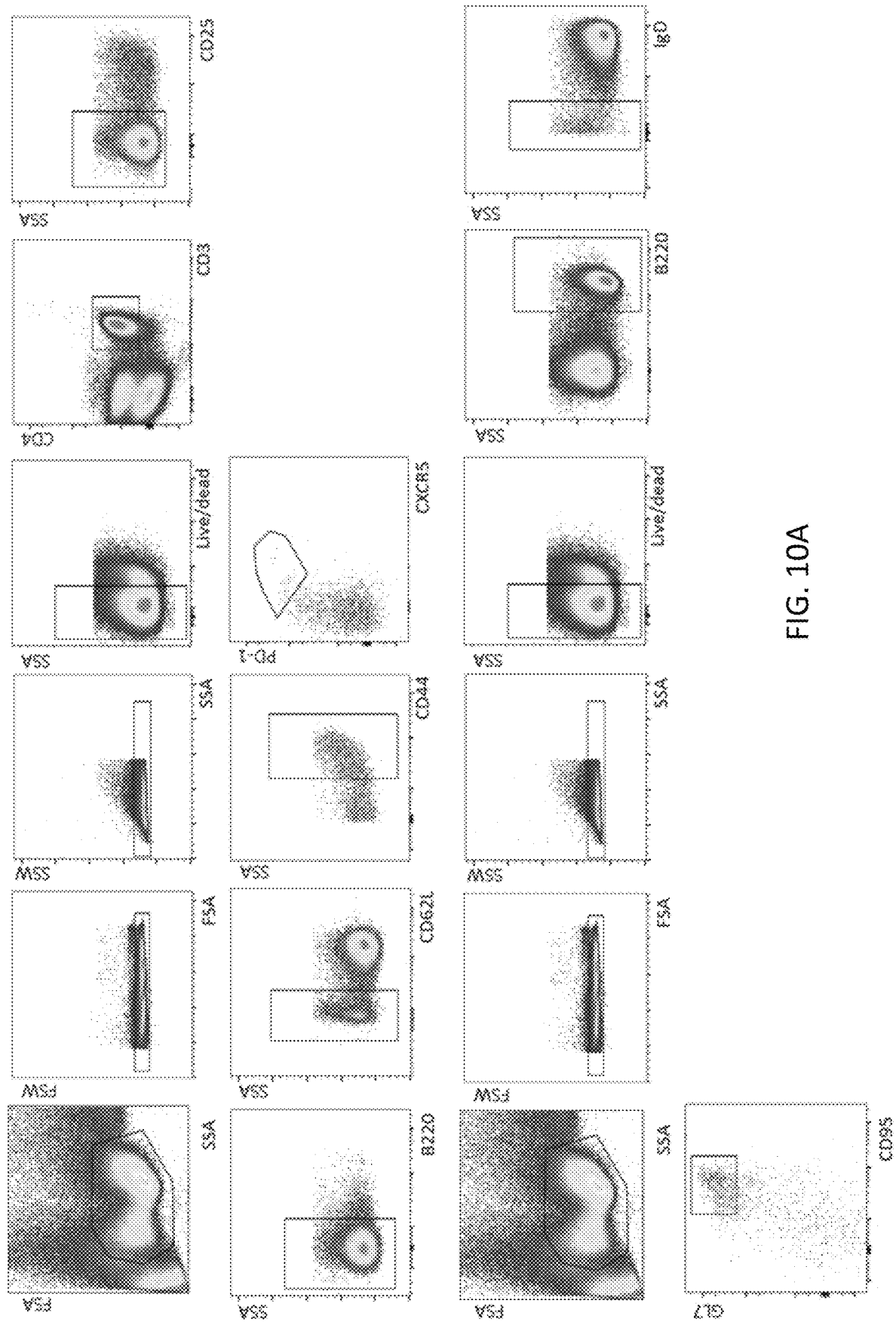
FIG. 10A-10B. Gating strategies.
Figure 10B:
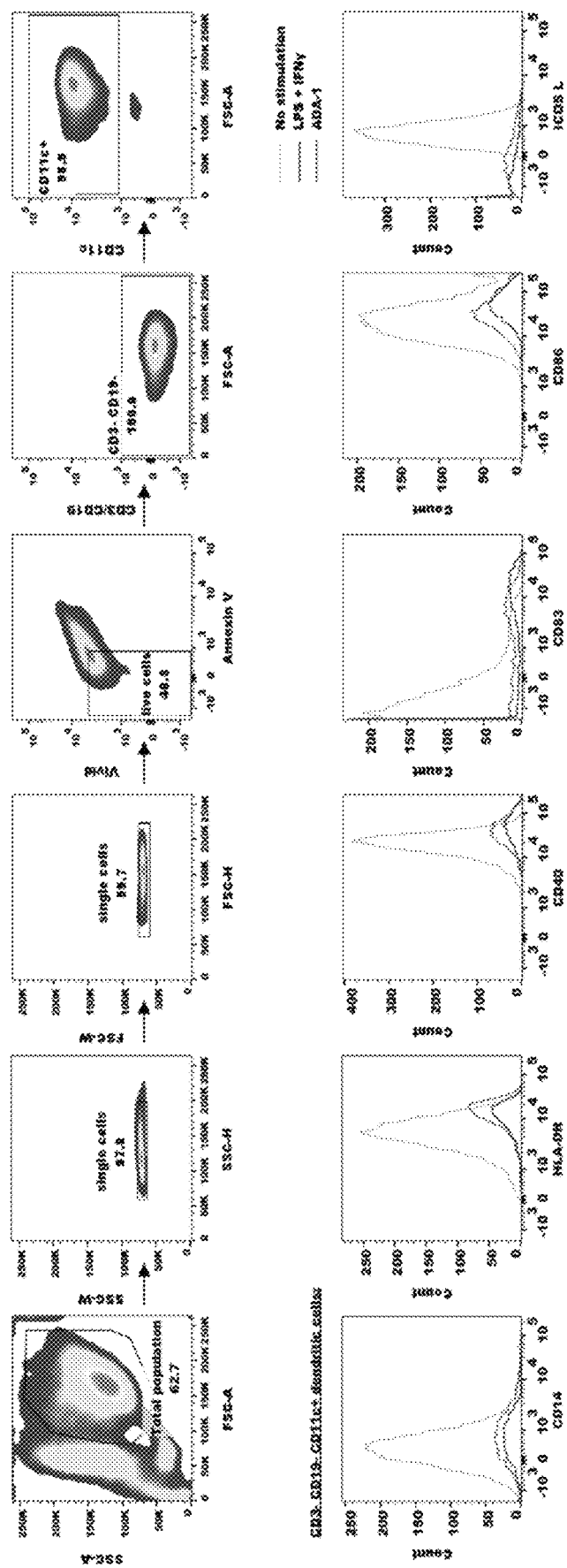
Figure 11A:
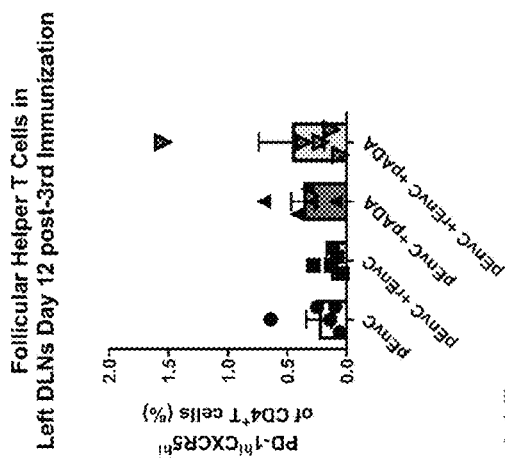
FIG. 11A-11F. DNA-protein co-immunization requires simultaneous delivery of DNA and protein immunogens. Mice were immunized as in FIG. 5. $T_{FH}$ (FIG. 11A-FIG. 11C) and GC B (FIG. 11D-FIG. 11F) cell frequencies were determined in the left DLNs at days 3 (FIG. 11A, FIG. 11D), 6 (FIG. 11B, FIG. 11E), and 12 (FIG. 11C, FIG. 11F) post-$3^{rd}$ immunization. Each point represents an individual animal, bars represent the mean and SD. *p<0.05, p<0.01, *p<0.001, ****p<0.0001 by one-way ANOVA. Data are representative of one experiment with n=5/group.
Figure 11B:
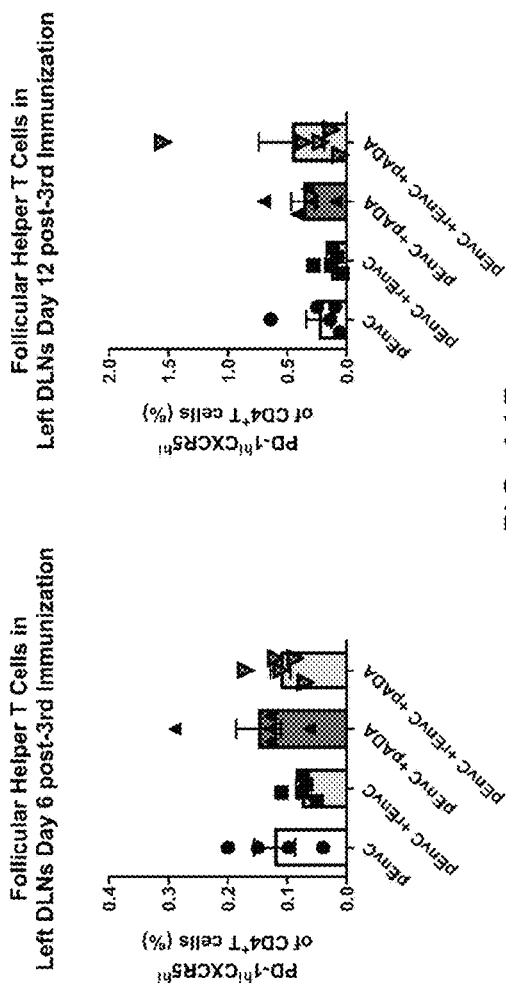
Figure 11C:
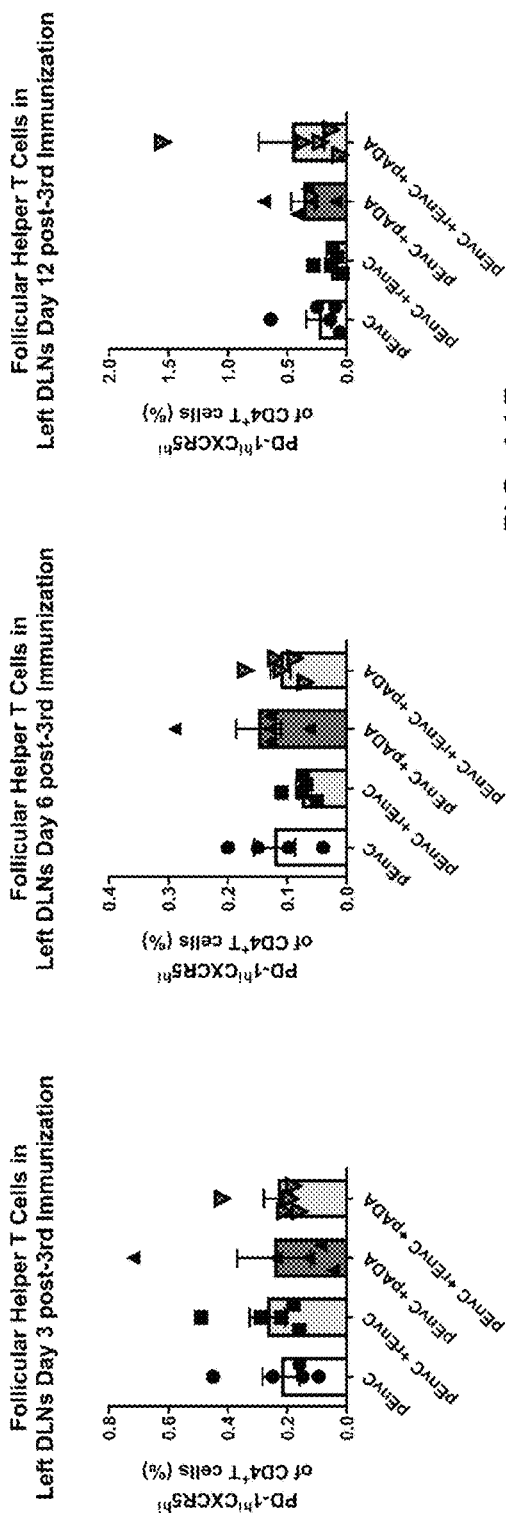
Figure 11D:
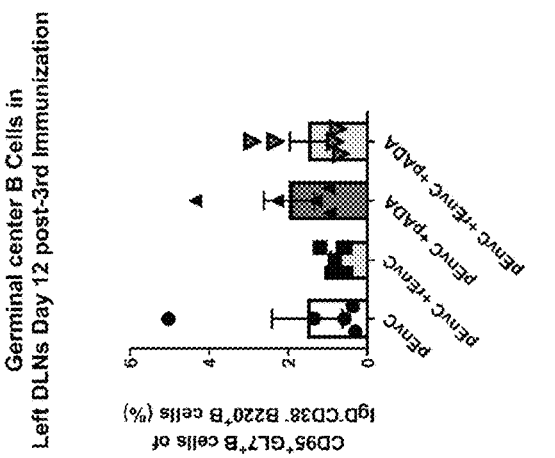
Figure 11E:
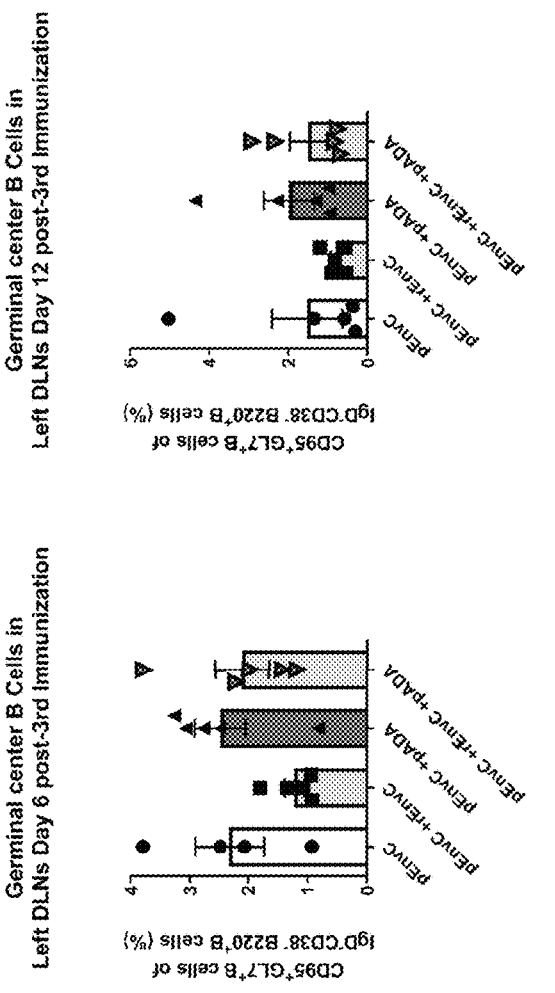
Figure 11F:
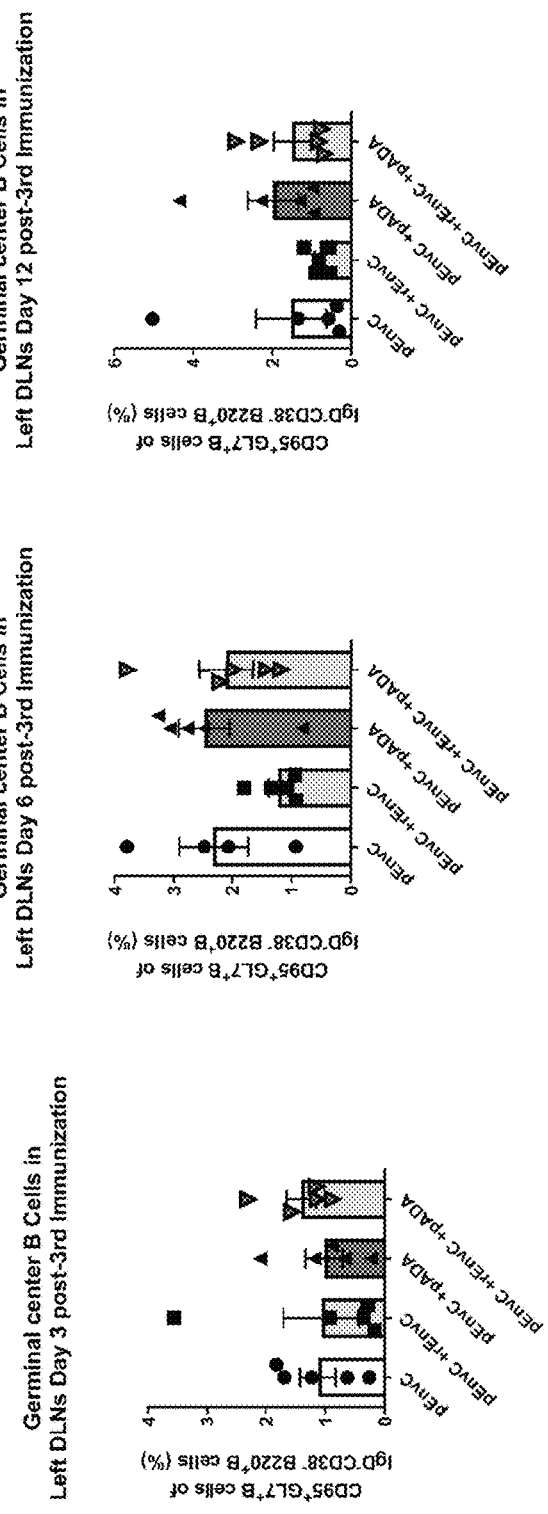

Extracellular adenosine limits the function of antigen-presenting cells, and it has been demonstrated that deamination of adenosine supports murine dendritic cell (DC) activation in vitro[13]. Moreover, ADA-1 has been shown to directly affect human myeloid-derived DCs (mDCs) from healthy and HIV-infected individuals by inducing their maturation and immunogenicity[5]. However, whether ADA-1-matured mDCs influence the differentiation of CD4+ T cells towards a $T_{FH}$ phenotype has yet to be determined. To test this, monocytes from healthy PBMCs were treated with GM-CSF/IL-4 48 h followed by maturation with either ADA-1 or LPS/IFNγ as a positive control for 24 hrs. The frequency of surface costimulatory and HLA marker-expressing cells was assessed in ADA-1-treated mDCs compared to unstimulated cells after 24 hours. The gating strategy used for mDCs and the determination of their surface marker frequencies is shown in FIG. 10. This indicated that LPS/IFNγ and ADA-1 significantly up-regulated the percentage of CD40– (mean 80.13% of mDCs, $p<0.0001$), CD83– (mean 46.77% of mDCs, $p<0.0001$), CD86– (mean 69.33% of mDCs, $p<0.0001$) and HLA-DR– (mean 88.6% of mDCs, $p<0.001$) positive human mDCs compared to unstimulated control. (FIG. 1A-1D). The increase in ADA-1-mediated CD83 expression however, was noted to be significantly higher than immature unstimulated cells (mean 46.77% compared to 1.25%, $p<0.0001$) (FIG. 1B). FIG. Importantly, both LPS/IFNγ and ADA-1 induced the expression of CD40 (means of 80.13% and 83.08% respectively, compared to 25.08% in unstimulated, $p<0.0001$) (FIG. 1A), which is known to be important for human $T_{FH}$ helper function through interaction with CD40L. These data confirm that ADA-1 induces the maturation of human mDCs in our in vitro culture system, and indicates that ADA-1 mediates its effect on $T_{FH}$ function, at least in part, by altering the phenotype and maturation status of antigen-presenting cells.

ADA-4 Alters the Cytokine and Chemokine Profile of Human mDCs In Vitro into a Pro-$T_{FH}$ Phenotype In order to further characterize ADA-1-mediated effects on the mDC phenotype in vitro, human mDCs were generated and treated as described above to evaluate their cytokine and chemokine profile. LPS/IFNγ significantly induced the production of high levels of cytokines and chemokines consistent with a pro-inflammatory phenotype compared to unstimulated cells, namely IL-6 ($p<0.0001$), IL-12p70 ($p<0.01$), IL-1β ($p<0.01$) and CXCL13 ($p<0.0001$) (FIG. 1F, 1G, 1J, 1K). IL-12p70[20] (FIG. 1G) is reflective of a pro-$T_H1$ DC profile. LPS plus IFNγ also induced minimal secretion of the anti-inflammatory cytokine IL-10 from mDCs (FIG. 1I), but not the $T_H2$ cytokine IL-4 (FIG. 1H).

ADA-1 administration significantly increased the secretion of the pro-inflammatory molecules IL-6 ($p<0.05$), IL-1β ($p<0.01$) and CXCL13 ($p<0.01$) (FIG. 1F, 1J, 1K) from mDCs compared to untreated cells. ADA-1 administration also significantly increased the secretion of the anti-inflammatory molecules IL-4 ($p<0.05$) and IL-10 ($p<0.01$) (FIG. 1H, 1I) from mDCs compared to unstimulated cells and to those stimulated by LPS/IFNγ ($p<0.01$ for both).

IL-6 is the most crucial cytokine for human $T_{FH}$ cell differentiation and is key regulator of the master $T_{FH}$ cell transcription factor Bcl6[21-24]. IL-1β and CXCL13 have also been implicated in $T_{FH}$ development/function[25-27]. IL-12p70FIG., although associated with promoting $T_{FH}$ cells[2], is mostly reflective of a pro-$T_{H}1$ DC profile. Thus, the combination of cytokines elicited by ADA-1 maturation in mDCs provides an appropriate environment to support $T_{FH}$ differentiation. The levels of ADA-1-induced IL-12p70 were significantly lower than those induced by LPS and IFNγ ($p<0.01$ and $p<0.001$, respectively) (FIG. 1G), while the levels of IL-4 and IL-10 were significantly greater than those induced by LPS and IFNγ ($p<0.01$) (FIG. 1H, 1I). This observation indicates that inflammatory responses mediated by ADA-1 are reduced as compared to LPS/IFNγ inflammatory responses. Thus, ADA-1-stimulated mDCs produce high levels of the key pro-$T_{FH}$ cytokine IL-6, high amounts of IL-1β and CXCL13, which indicates a role in $T_{FH}$ cell differentiation, function, and proliferation[26,27], alongside robust levels of the regulatory cytokines IL-4 and IL-10.

Overall, our results demonstrate that ADA-1 can induce the maturation of dendritic cells and elicits an mDC cytokine/chemokine secretion phenotype that is distinct from $T_{H}1$ and $T_{H}2$ cytokine profiles, and which supports $T_{FH}$ cell differentiation.

pADA Enhances $T_{FH}$ Cell Frequency In Vivo

Figure 2D:
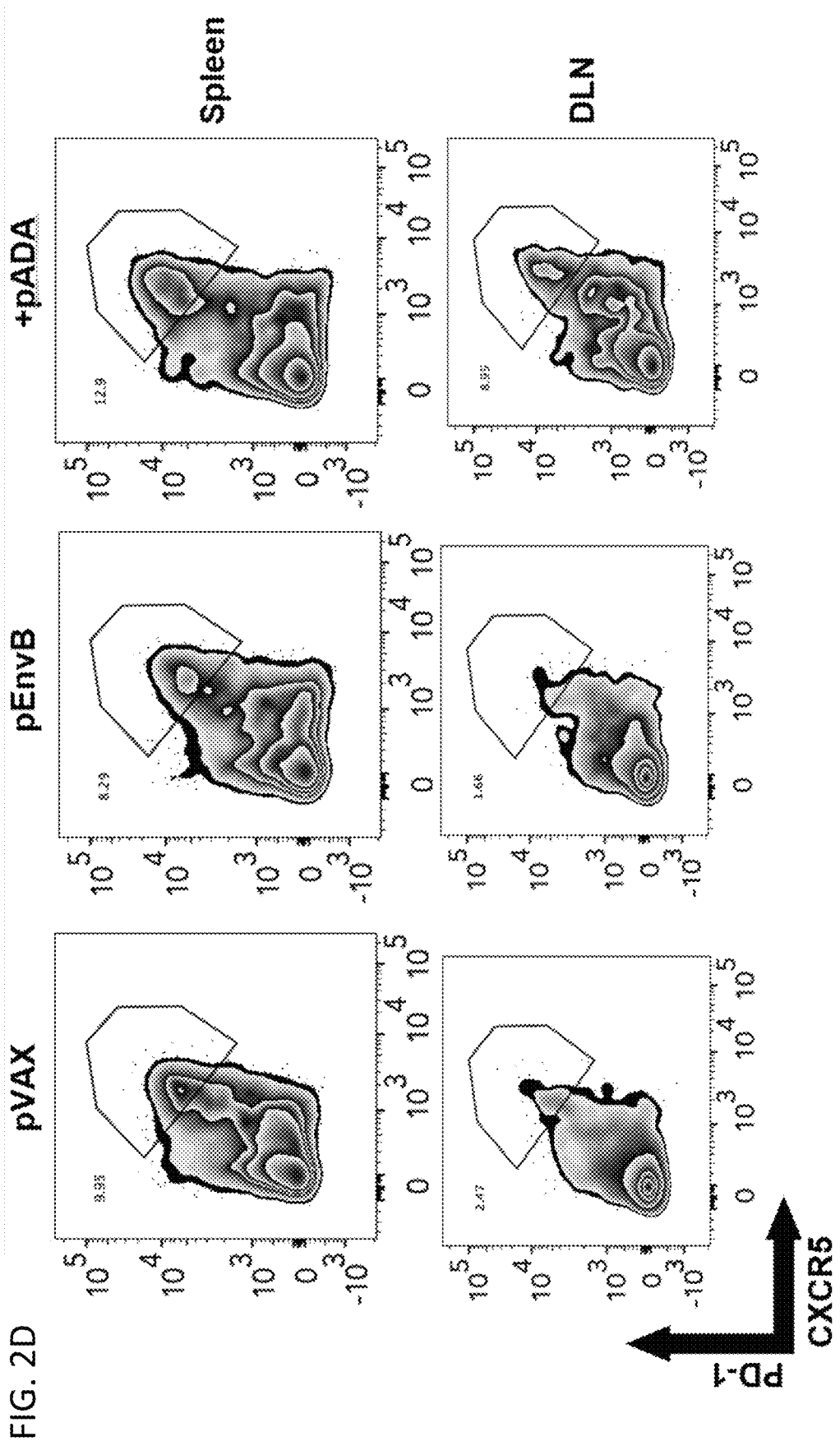
(FIG. 2D) Representative flow plots for the data presented in FIG. 2B and FIG. 2C. Each point represents an individual animal, bars represent the mean and SD. Each point represents the average of duplicate samples from an individual animal, bars represent the mean and error bars represent the SEM. *p<0.05, p<0.01, *p<0.001, ****p<0.0001 by one-way ANOVA. Data are representative of four independent experiments with n=3-6/group.

We have previously published that addition of exogenous ADA-1 enhanced pre-$T_{FH}$ helper function in an in vitro T:B co-culture system, and demonstrated that this enhancement supported robust IgG secretion[4]. To determine the effect that pADA co-immunization has on $T_{FH}$ cells in vivo, mice were vaccinated three times, separated by two weeks, with either empty plasmid (pVAX), DNA-encoded HIV-1 gp160 consensus envelop antigen from clade B viruses (pEnvB), or co-immunized with pEnvB and plasmid-encoded ADA-1 (+pADA) (FIG. 2A), and the frequency of $T_{FH}$ cells in the spleens and DLNs of vaccinated animals was quantified at day 7 post-3$^{rd}$ immunization by flow cytometry. We observed statistically significant increases in the frequency of GC $T_{FH}$ cells in the DLNs of pADA co-immunized animals as compared to animals receiving either empty plasmid vector or pEnvB alone ($p<0.001$) (FIG. 2C). This increased frequency of $T_{FH}$ appears limited to the local DLNs (popliteal and inguinal), as such enhancements were not observed in the spleens of pADA co-immunized animals (FIG. 2B). These results indicate that molecular ADA-1 can enhance $T_{FH}$ cell frequency in vivo and importantly, demonstrate that the adjuvant effect of pADA is local and not systemic.

pADA Enhances HIV-Specific IgG in Vaccinated Animals

Figure 3A:
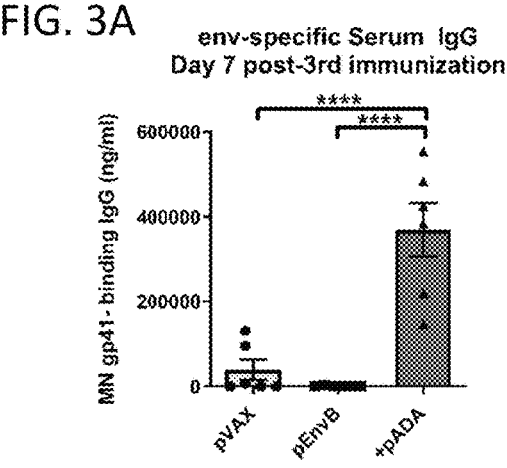
FIG. 3A-3F. Co-immunization with pADA enhances serum IgG. Mice were immunized as in FIG. 1. Total HIV-specific serum IgG (FIG. 3A), IgA (FIG. 3B), IgG1 (FIG. 3C), IgG2b (FIG. 3D), IgG2c (FIG. 3E), and IgG3 (FIG. 3F) was quantitated in serum via ELISA at day 7 post $3^{rd}$ immunization. Each point represents the average of duplicate samples from an individual animal, bars represent the mean and SEM. *p<0.05, p<0.01, *p<0.001, ****p<0.0001 by one-way ANOVA. Data are representative of two independent experiments with n=6/group FIG. 4A-4B. Co-immunization with pADA does not increase anti-nuclear antibody production.
Figure 3B:
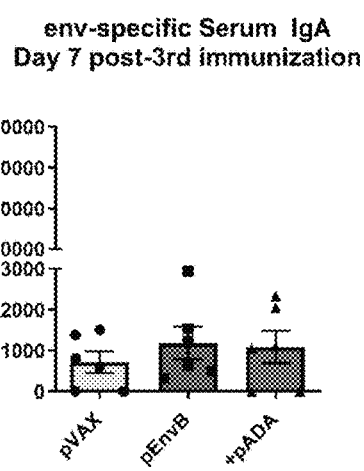
Figure 3C:
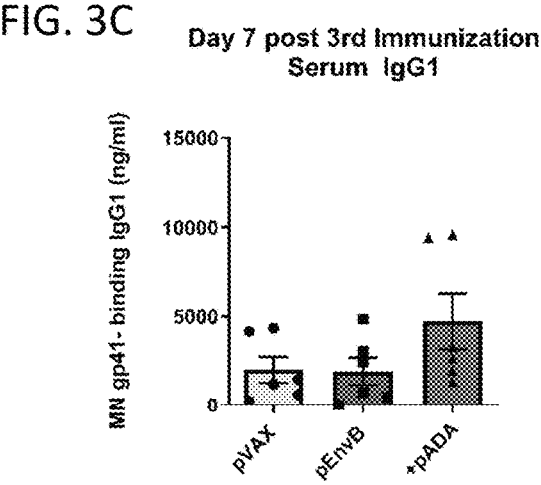
Figure 3D:
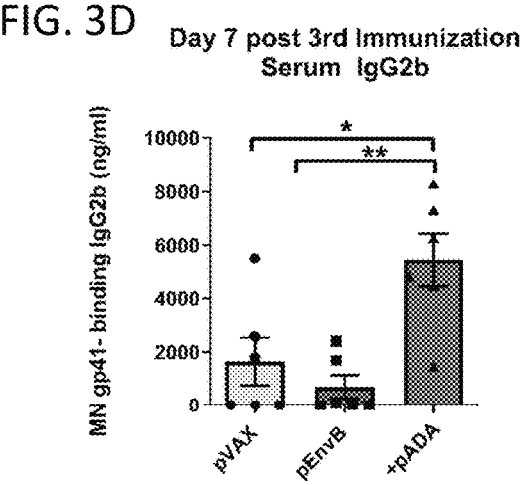
Figure 3E:
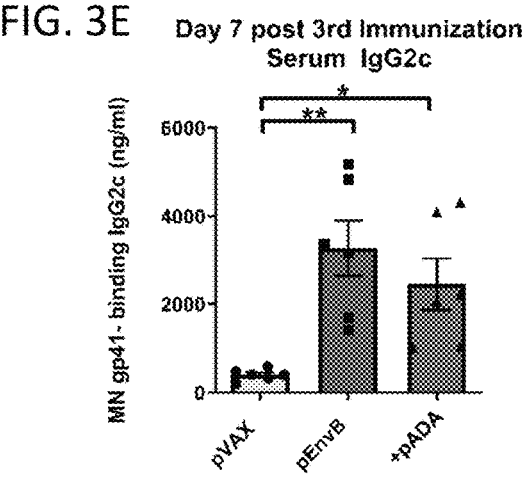
Figure 3F:
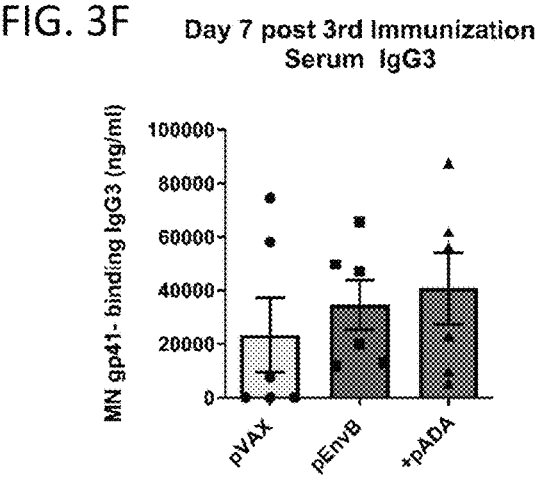

Since ADA-1 enhanced GC-$T_{FH}$ cell frequency, we then determined if ADA-1 improves Ab response in vivo. We hypothesized that co-delivery of plasmid-encoded ADA-1 (pADA) in the context of our anti-HIV DNA vaccine would enhance HIV-specific IgG in vaccinated animals. Serum ELISA from vaccinated animals (FIG. 2A) revealed statistically significant increases in HIV-1 envB-binding IgG in pADA co-immunized animals compared to those receiving either empty plasmid ($p<0.0001$) or antigen alone ($p<0.0001$) (FIG. 3A). No differences in serum IgA (FIG. 3B) or IgM (not shown) were detected at this time point. These data indicate that pADA co-immunization enhances antigen-specific serum antibody responses in the context of an HIV-1 DNA vaccine. Further analysis of the IgG subclasses produced revealed that pADA co-immunization resulted in a statistically significant increase in HIV-specific IgG2b compared to animals which received antigen alone ($p<0.001$) (FIG. 3D), which is indicative of $T_{FH}$-type immunity. This was not true for IgG1 (FIG. 3C), IgG2c (FIG. 3E), or IgG3 (FIG. 3F). Importantly, IgG2 antibodies have been associated with long-term non-progression in HIV-infected human patients[29, 30].

Co-Immunization with pADA does not Elicit the Production of Auto-Antibodies

Figure 4A:
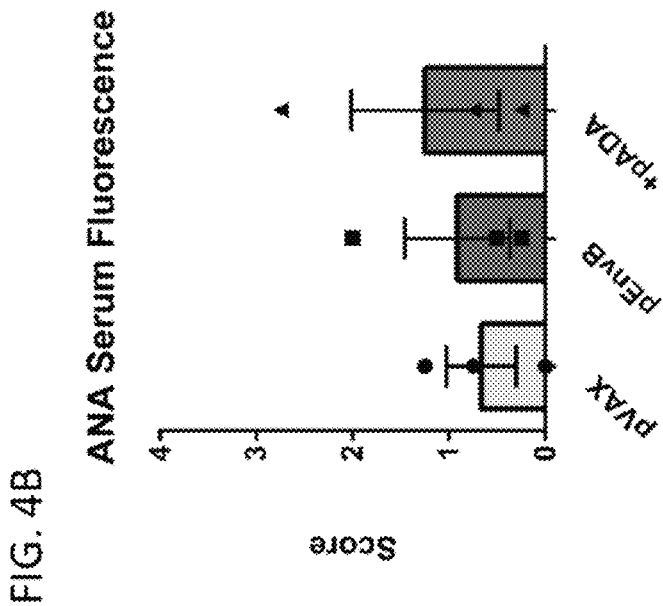
(FIG. 4A) Mice were immunized as in FIG. 1, and anti-nuclear antibody was quantified in serum at day 7 post-$3^{rd}$ immunization via ELISA. Each point represents the average of duplicate samples from an individual animal, bars represent the mean and error bars represent the SEM.
Figure 4B:
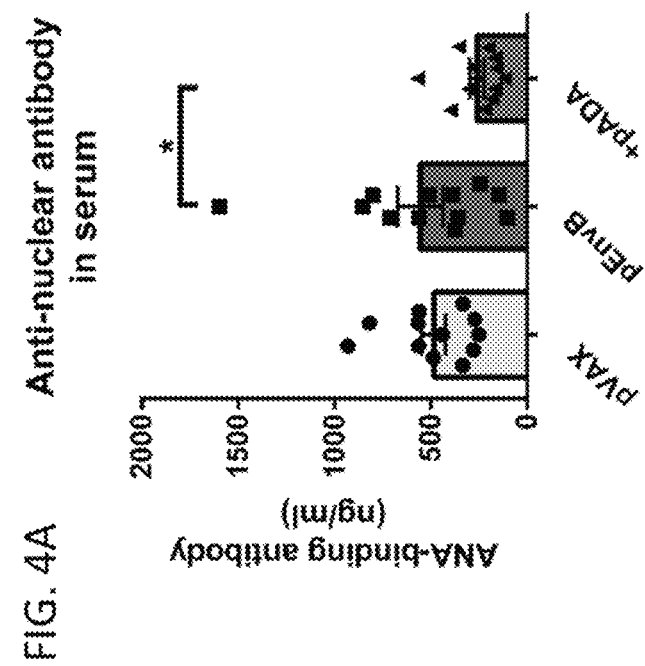
(FIG. 4B) Hep-2 ANA slides were incubated with 1:40 dilutions of serum from vaccinated animals, and ANA was detected by immunofluorescence using FITC-conjugated donkey, anti-mouse IgG. Images were scored for ANA fluorescence on a 0-4 scale according to the manufacturer's protocol. Each point represents the mean of 5 individual blind scores for 3 mice in each group. Bars represent the mean and error bars represent the SEM.

As increased $T_{FH}$ frequency has been associated with autoimmunity[31-33], we quantified the levels of anti-nuclear antibody (ANA) present in the serum of vaccinated animals after three immunizations using a mouse ANA ELISA. There was no detectable increase in the levels of ANA in the serum of mice co-immunized with pADA compared to mice receiving either empty plasmid vector or pEnvB alone (FIG. 4A). While envelope-vaccinated animals did not display increased ANAs compared to mice receiving empty plasmid, co-immunization with pADA resulted in a statistically significant decrease in serum ANA as compared to animals receiving envelope only ($p<0.05$). The presence of anti-nuclear antibodies were also evaluated using a modified ANA/Hep-2 immunofluorescence assay. There was no detectable difference in ANA fluorescence intensity between animals vaccinated with empty plasmid vector, our env DNA immunogen only, or animals co-immunized with DNA and molecular ADA-1 (FIG. 4B). These data indicate that ADA-1 supports the expansion of antigen-specific $T_{FH}$ cells in the post-vaccination GC and does not promote autoimmune antibody formation in this model. This information is critical to translating the use of ADA-1 as a vaccine adjuvant in the clinic.

pADA Enhances Serum IgG in a DNA-Protein Co-Immunization Regimen

DNA-prime protein-boost vaccination regimens and other heterologous prime-boost regimens have demonstrated significantly enhanced humoral responses when compared to either DNA-only or protein-only vaccination regimens[34]. This technique has been shown to enhance immunity in pre-clinical and clinical trials[35-37]. Recently we demonstrated that simultaneous delivery of DNA immunogens and protein immunogens together is superior to protein-only immunization with respect to the kinetics, magnitude, and breadth of antibody responses[38]. Such vaccination regimens can capitalize on the ability of the DNA platform to engender robust cell-mediated responses and the ability of the protein-adjuvant platform to induce robust humoral responses, while potentiating a shortened immunization regimen in the clinic.

Figure 5A:
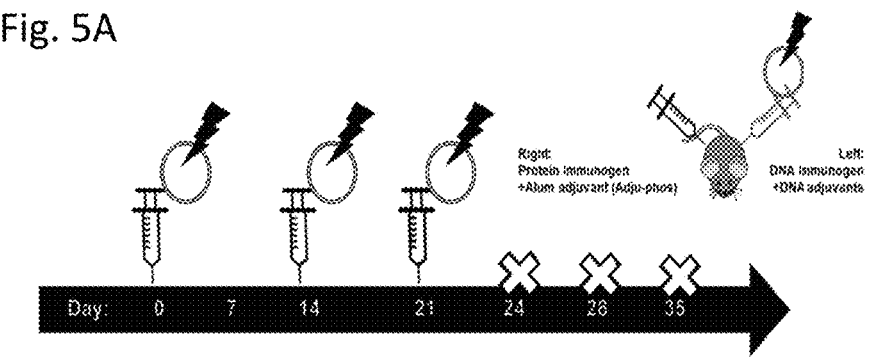
FIG. 5A-5D. Co-immunization with pADA enhances serum IgG in a DNA-protein co-immunization regimen.
Figure 5B:
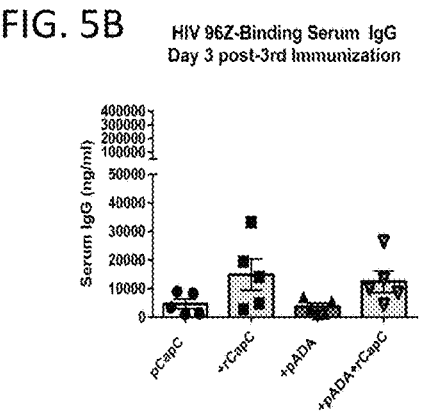
Figure 5C:
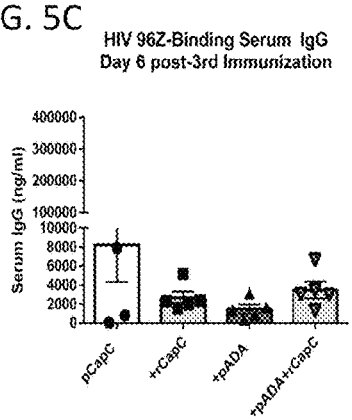

It was determined herein, that addition of pADA to the DNA arm of this regimen would enhance anti-HIV IgG quantitatively and qualitatively, in a GC $T_{FH}$-dependent manner. The env immunogens used in this study were cloned from the plasma of an HIV subtype C-infected subject in the CAPRISA cohort who developed nAbs early in infection and continued to broaden subsequently over 4.5 years of study[39]. A single env sequence from 54 weeks post infection was motif optimized and used in this vaccine study as DNA plasmid expressing gp160 native trimer (pCAP257-54wk_D) and as a modified truncated, non-cleaved trimeric glycoprotein gp140. We vaccinated mice with either clade C pCAP257-54wk_D env DNA alone (pEnvC), pCAP257-54wk_D DNA and gp140 CAP257-54wk_D protein (pEnvC+rEnvC), pCAP257-54wk_D DNA and pADA without protein (pEnvC+pADA), or pCAP257-54wk_D DNA and pADA with simultaneous gp140 CAP257-54wk_D protein immunization (pEnvC+rEnvC+pADA). All DNA immunogens and adjuvants were delivered to the left tibialis anterior followed by in vivo electroporation. Protein immunogens were delivered in aluminum phosphate adjuvant (AdjuPhos) in the right quadricepsfemoris (FIG. 5A). While protein-adjuvant GC responses typically develop in 9-14 days, the kinetics of the GC response to DNA immunogens has not been well characterized, thus we vaccinated animals and sacrificed them at days 3, 6, and 12 post-$3^{rd}$ immunization and quantified the frequencies of GC $T_{FH}$ and GC B in the DLNs and env-binding IgG in the serum. FIG. 5B, C).

Figure 5D:
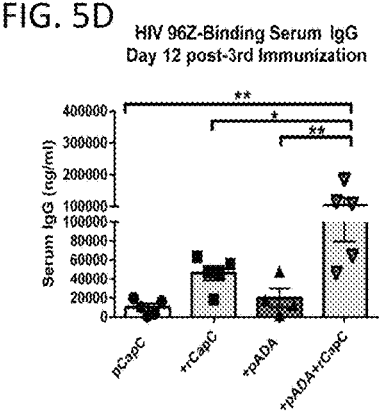
Figure 7A:
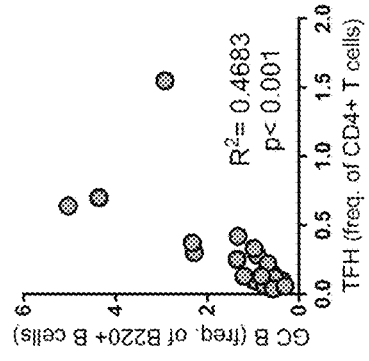
FIGS. 7A-7F. GC B and $T_{FH}$ frequencies strongly correlate during DNA-protein co-immunization. Mice were immunized as in FIG. 5. $T_{FH}$ and GC B frequencies were correlated in the left (top) and right (bottom) DLNs at days 3 (FIG. 7A, FIG. 7D), 6 (FIG. 7B, FIG. 7E), and 12 (FIG. 7C, FIG. 7F) post-$3^{rd}$ immunization. Each point represents an individual animal. *p<0.05, p<0.01, *p<0.001, ****p<0.0001 by Pearson correlation. Data are representative of one experiment with n=5/group.
Figure 7B:
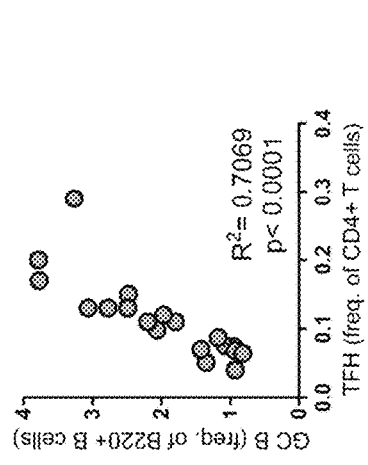
Figure 7C:
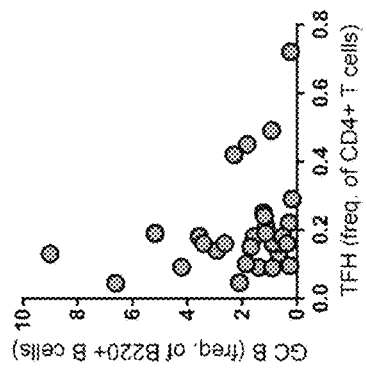
Figure 7D:
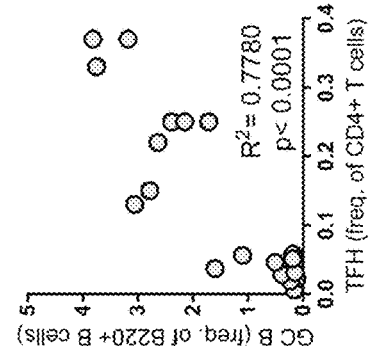
Figure 7E:
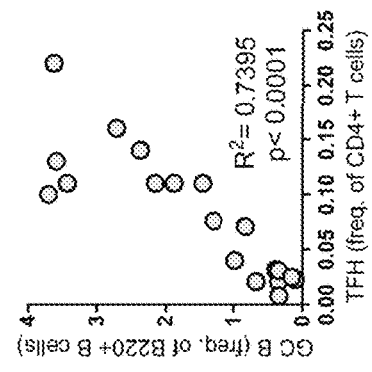
Figure 7F:
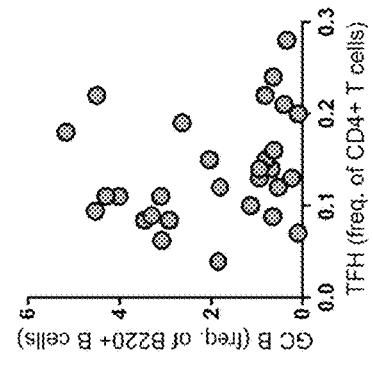

Animals that received pADA with pEnvC and simultaneous protein immunization, had significantly more envC-binding IgG in serum than animals that received either DNA alone (p<0.001), DNA and protein (p<0.05), or DNA with pADA (p<0.001) (FIG. 5D). These data confirm that pADA co-immunization can enhance antigen-specific serum antibody responses in the context of a DNA-protein co-immunization.

Figure 8:
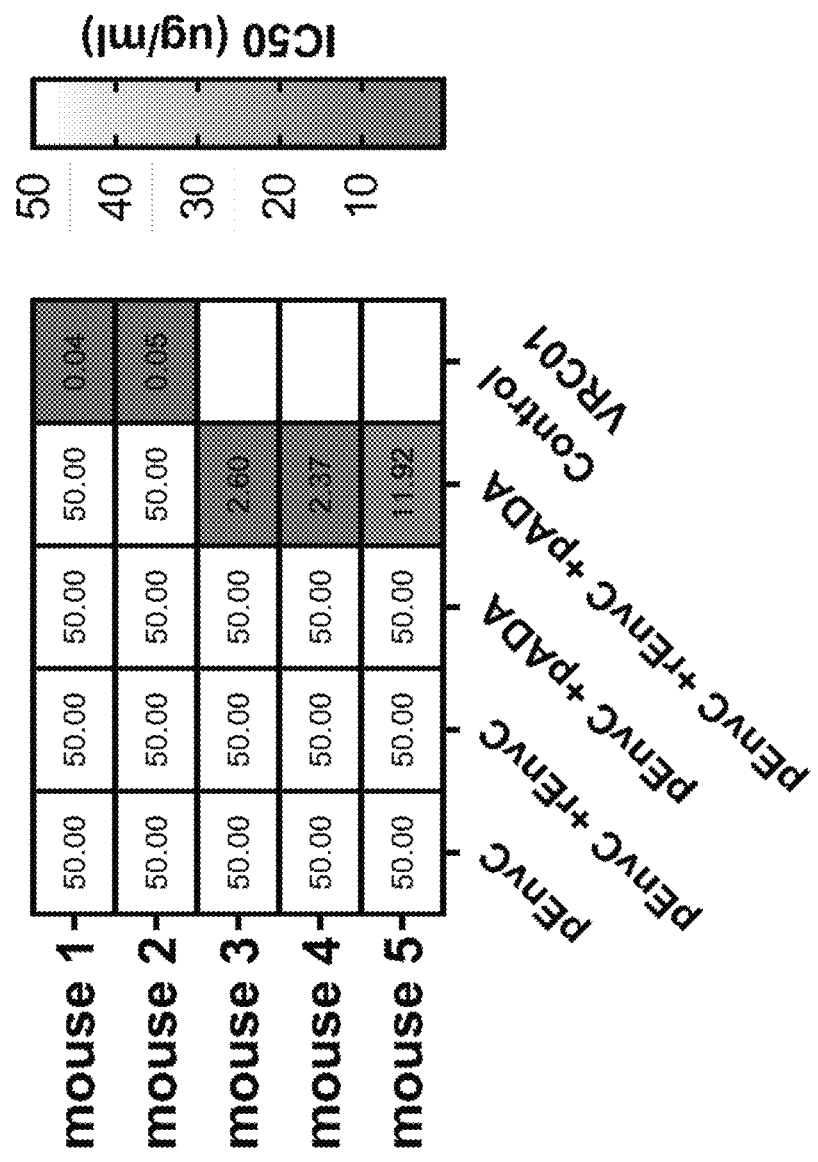
FIG. 8. ADA promotes the development of neutralizing antibodies during DNA-protein co-immunization. Mice were immunized as in FIG. 5. IC50 values for purified mouse IgG were determined using the single-cycle TZM-bl neutralization assay. 50 μg/ml of mouse sera were added to test wells and values greater than 50 μg/ml are represented as 50 μg/ml. Each rectangle represents a single mouse within a group. 2 μg/ml of VRC01 was used as a positive control for neutralization. Data are representative of one experiment with n=5/group.

Immunization with pADA Enhances $T_{FH}$ Function in a DNA-Protein Co-Immunization Regimen Analysis of HIV-specific IgG in the serum of animals receiving pEnvC and pADA with simultaneous rEnvC glycoprotein immunization indicated that pADA enhanced GC activities. This was confirmed by collecting the popliteal and inguinal lymph nodes from the left and right leg of each animal and quantifying GC $T_{FH}$ and GC B cell frequencies by flow cytometry. Surprisingly, despite the observed increase in env-binding IgG in the serum of animals which received pEnvC, pADA, and simultaneous protein compared to those receiving pEnvC and simultaneous protein without pADA (FIG. 5D), all groups that received protein simultaneously displayed increases in the frequencies of GC $T_{FH}$ and GC B cells in the right DLNs irrespective of pADA co-immunization (FIG. 6A-6F). This data indicates that pADA enhances GC $T_{FH}$ function, but not necessarily GC $T_{FH}$ frequency, in this model. At all time points, there was no difference in the frequencies of GC $T_{FH}$ or GC B cells in the left DLNs (FIG. 11). As expected, at the later time points, GC B frequencies most strongly correlated with $T_{FH}$ frequencies in the right DLNs but not in the left DLNs (FIG. 7A-7F). As observed in our DNA only immunization regimen (FIG. 2), these responses appeared to be specific to the DLNs, as we were only able to detect differences in the spleen at day 12 post-$3^{rd}$ immunization, when animals that received pADA co-immunization and simultaneous protein immunization exhibited increased GC B cell frequency compared to animals receiving pEnvC alone (p<0.05) or pEnvC with pADA (p<0.01), but not those receiving pEnvC and protein (FIG. 12). The data indicates that the discrepancy between $T_{FH}$ frequencies induced by DNA and pADA alone in this experiment compared to our DNA only experiments (FIG. 2) is likely be due to differences in immunogenicity or kinetics of GC formation between the two env plasmids. The data indicates that the robust GC formation observed upon immunization with protein and alum adjuvant likely make it difficult to distinguish pADA-mediated changes in the frequencies of GC cells.

pADA Promotes the Generation of HIV Neutralizing Antibodies During DNA-Protein Co-Immunization Only animals that received DNA and protein in the presence of pADA displayed increased envC-binding IgG at day 12 post-$3^{rd}$ immunization (FIG. 5). However, all animals that received protein co-immunization had increased frequencies of GC cells in the right draining lymph nodes (FIG. 6). This indicates that administration of pADA supports enhanced GC function and thus alters the quality of humoral responses in this vaccination model. Therefore, the quality of pADA-induced humoral responses was evaluated in the mouse vaccination model using a TZM-bl neutralization assay. Murine IgG was purified from the individual serum samples in order to remove any serological agents that can inhibit viral infection in vitro. Remarkably, despite the similar frequencies of GC cells in animals which received simultaneous protein immunization, we detected neutralization of heterologous, tier-1 subtype C HIV-MW965 pseudovirus using IgG from mice that received DNA and protein along with pADA co-immunization (FIG. 8). Three of the five immunized mice developed nAbs with potent activity, with IC50 concentrations ranging from 2.4 to 11.9 μg/ml. These data indicate that pADA enhances the function of GCs, independent of increases in frequencies of GC cell populations.

pADA Promotes T Cell Responses in a DNA-Protein Co-Immunization Regimen

Figure 9A:
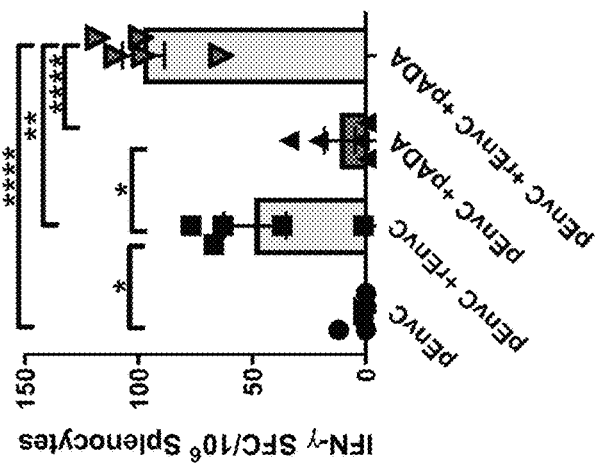
FIG. 9A-9C. Molecular ADA enhances IFNγ secretion during DNA-protein co-immunization. Mice were immunized as in FIG. 5. Splenocytes were assayed for HIV-specific IFNγ production at days 3 (FIG. 9A), 6 (FIG. 9B), and 12 (FIG. 9C) post-$3^{rd}$ immunization. Each point represents the average of duplicate assays for an individual animal for days 3 and 6, and error bars represent the SEM. Each point represents a single assay for an individual animal for day 12 and error bars represent the SD. *p<0.05, p<0.01, *p<0.001, ****p<0.0001 by one-way ANOVA. Data are representative of one experiment with n=5/group.
Figure 9B:
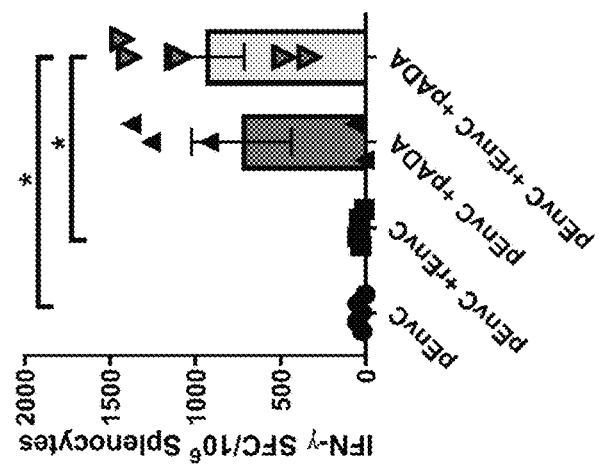
Figure 9C:
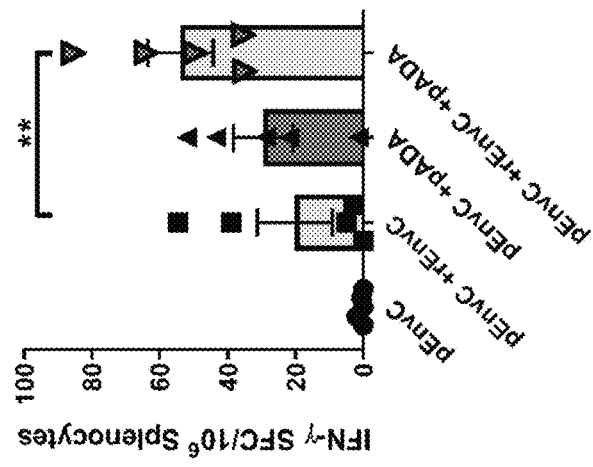

Next, the effect of pADA co-immunization on cell mediated immunity was investigated as both CD4$^+$ and CD8$^+$ T cell responses are required for HIV protection. Thus the function of CD8$^+$ and CD4$^+$ splenic T cells was evaluated in the context of this DNA-protein co-immunization regimen by IFNγ ELISpot. Increased frequencies of IFNγ spot-forming units (SFUs) were detected in groups that were co-immunized with pADA and protein simultaneously at days 3 and 6 post $3^{rd}$ immunization (FIG. 9A-9B). At day 12 post-$3^{rd}$ immunization, groups which received simultaneous protein co-immunization with or without pADA had statistically significant increases in IFNγ-secreting cells in the spleen compared to groups which received pEnvC alone or pEnvC with pADA (p<0.05) (FIG. 9C). However, at day 12 post $3^{rd}$ immunization, animals which received pEnvC, pADA, and rEnvC had significantly more IFNγ SFUs compared to animals which received wither pEnvC alone (p<0.0001), pEnvC with pADA (p<0.0001), or pEnvC with protein (P<0.01). These data indicate that co-immunization with pADA in the context of a DNA-protein regimen promotes effector T cell function. This knowledge is critical as both humoral and cell-mediated responses will be necessary for the development of a successful HIV vaccine. Overall, our findings indicate that pADA enhances $T_{FH}$ function which in turn, improves the quality of both humoral and cell mediated immune responses to vaccine antigens.

Discussion

GCs are dynamic sites within secondary lymphoid organs where $T_{FH}$ cells provide B cells with the necessary receptor-ligand and cytokine-mediated stimuli to induce affinity maturation, somatic hypermutation, and class-switching of B cell receptors. Subsequently B cells exit the GC as memory B cells or long-lived plasma cells. Thus, the GC is the inductive site for quality humoral responses[40]. Importantly, it has been demonstrated that the GC reaction is critical to the development of protective, broadly neutralizing antibody responses to HIV as such antibodies show evidence of extensive hypermutation[10, 41-43]. Furthermore, this site can be used to assess the efficacy of env-based HIV vaccines[44].

Adenosine deaminase is a critical metabolic enzyme required for the function of lymphocytes[45]. Our previous work demonstrates that ADA) is significantly upregulated in GC $T_{FH}$ cells[4]. Importantly we demonstrated that addition of exogenous ADA-1 to less-efficient pre-$T_{FH}$ cells enhanced the ability of these cells to induce IgG production by autologous B cells in vitro[4]. In this study we evaluated the ability of plasmid-encoded ADA-1 to enhance GC $T_{FH}$ frequency and function in vivo, in the context of a DNA vaccine targeting HIV-1 envelope immunogens.

In vitro studies of human mDCs treated with ADA-1 indicated that treatment of professional antigen-presenting cells with ADA-1 induces maturation and promotes cytokine production[5]. Testing the effect of ADA-1 on mDCs in our in vitro system provided a critical way to evaluate the direct effect of ADA-1 on mDCs, independent of other cell types. We observed increased frequencies of mDCs positive for surface costimulatory and antigen-presenting molecules, such as CD40 and HLA-DR following ADA-1 treatment in our in vitro culture system. This supports the conclusion that stimulation with ADA-1 up-regulated the expression of surface markers of maturation on mDCs from both healthy and HIV-infected human subjects. ADA-1 treatment also altered the cytokine/chemokine secretion profile of these cells and enhanced their immunogenicity[5]. The finding that ADA-1 induced an increase in the frequency of mDCs positive for the activation markers CD40, CD86 and HLA-DR to frequencies similar to those induced by LPS and IFNγ, is indicative of robust ADA-1 potency. Importantly, this happens in the absence of an overtly inflammatory environment as ADA-1 was not able to elicit IL-12 secretion from treated DCs. Interestingly, we did not detect differences in the frequencies of ICOSL+ mDCs in this system. This establishes that ICOSL is required on the surface of cognate B cells for $T_{FH}$ cell development and function in mouse models Furthermore, absence of ICOSL upregulation can be compensated for by antigen abundance[19]. In addition, the importance of ICOSL expression in the DC contribution to the $T_{FH}$ cell program appears to be more important for plasmacytoid DCs (pDCs) than mDCs, where the former cells may promote interactions between ICOS and ICOSL to mount $T_{FH}$ responses against certain viruses such as influenza 6.

Figure 1F:
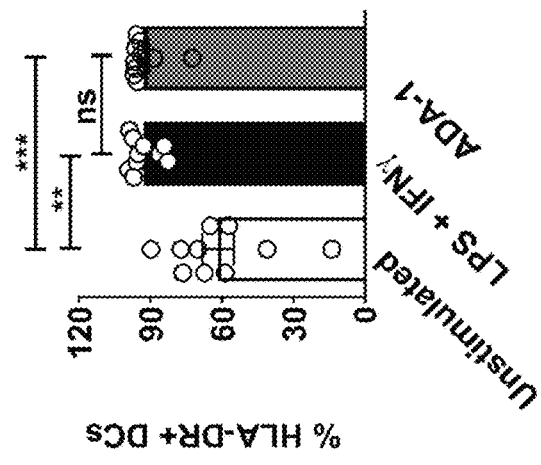

The data herein indicates that ADA-1 altered the cytokine and chemokine profile of mDCs to one that promotes a $T_{FH}$ program. ADA-1 induced robust IL-6 production along with low levels of IL-12p70 from mDCs (FIG. 1F, 1G). While IL-6 is required to support the expression of the GC master regulator Bcl6 via STAT1[22, 24, 8], the role of IL-12 in $T_{FH}$ differentiation is controversial. IL-12 can support the expression of Bcl6 via STAT4, however it also supports T-bet function, a master regulator which inhibits Bcl6[47,9]. These responses have also been demonstrated to remain intact in STAT4-deficient animals, suggesting that IL-6 signaling through STAT1/STAT3 can compensate for IL-12 signaling. The balance between Bcl6 and T-bet may be regulated by expression of IL-2, where high expression of IL-2 in the context of IL-12 signaling promotes T-bet, and low expression of IL-2 in the context of IL-12 signaling promotes Bcl6 function[16, 48]. It is in fact not just the presence or absence of IL-12 or any other cytokine or chemokine that contributes to the $T_{FH}$ differentiation pathway, but rather the amount secreted, duration, timing, location, and intensity of the signal along with the antigen involved, that shape the response[8]. Recent evidence indicates that IL-1B has a positive role in $T_{FH}$ development[27]. Finally, CXCL13, a key $T_{FH}$ chemokine and ligand for the characteristic $T_{FH}$ marker CXCR5, was increased in the supernatant of ADA-1-treated mDCs. CXCL13 promotes CXCR5 expression on immune cells[2]. Thus, the data indicate that increased CXCL13 expression promotes the expression of follicle-trafficking chemokine receptors in our system. It has been previously demonstrated that mDCs can upregulate CXCR5 to enter the follicles and prime $T_{FH}$ responses in the interfollicular area[8, 9]. Furthermore, CXCL13 has been shown to be crucial in the development of murine lymphoid tissues in vivo[49].

The ADA-1-mediated increase in IL-4 and IL-10 is suggestive of a balance in the established mDC response. Although high levels of IL-4 were observed with all treatments due to the presence of recombinant IL-4 in the culture medium, the significant increase observed upon ADA-1 treatment indicates a regulatory response which dampens inflammation. This is consistent with the absence of autoantibody in pADA co-immunized animals. Likewise, the high level of IL-10 observed in mDC cultures treated with ADA-1 counterbalances the inflammation induced by other inflammatory mediators and indicates a regulatory role, preventing an overactive $T_{FH}$ response[50]. Both IL-4 and IL-10 have strong effects on B cell activation and antibody responses[51, 52]. The ADA-1-induced mDC profile did not correlate with a pro-$T_H2$ profile, as other non-$T_H2$-associated cytokines and chemokines (IL-6, IL-1B, and CXCL13) were also increased by ADA-1 treatment in this system. Importantly, ADA-1 treatment robustly increased mDC secretion of IL-6, which is a critical driver of human $T_{FH}$ cell differentiation[21-24]. Hence, our findings indicate that ADA-1 treatment promotes an mDC profile that supports $T_{FH}$ differentiation (FIG. 1).

These data indicate that ADA-1 supports GC function by at least two distinct, but not mutually exclusive mechanisms. Firstly, immunization with plasmid-encoded ADA-1 (pADA) by electroporation leads to the expression and release of extracellular ADA-1 in the GC where it supports the GC $T_{FH}$:B cell interaction. This is supported by our data which demonstrate that exogenous ADA-1 treatment improves the $T_{FH}$ phenotype and enhances the capacity of less-efficient CD4+ T cells to provide help to antibody secreting cells resulting in increased IgG secretion. Secondly, ADA-1 promotes the maturation of and secretion of potentially $T_{FH}$-polarizing cytokines from antigen presenting cells in vitro. It is demonstrated herein that mDC maturation by ADA-1 induces the production of $T_{FH}$-polarizing cytokines IL-6 and CXCL13 (FIG. 1). Thus the data indicate that, in vivo, in the context of HIV DNA antigens, administration of pADA would enhance GC formation and promote $T_{FH}$-mediated help to B cells resulting in increased antibody production.

In support of these mechanisms, in vivo co-immunization with pADA in the context of an HIV-1 env DNA vaccine resulted in increased DLN $T_{FH}$ cell frequencies and increased env-binding antibody in the serum of vaccinated mice (FIG. 2). pADA co-immunization significantly enhanced IgG2b in this immunization model, suggestive of T-cell dependent antibody responses (FIG. 3). While $T_{FH}$ function is critical for humoral immunity, uncontrolled expansion of this population has been associated with the pathogenic inflammation that occurs in autoimmune disorders. Therefore, it was critical to evaluate the production of self-reactive antibodies in the context of pADA co-immunization. We were unable to detect increases in mouse anti-nuclear antibody (ANA) in the serum of animals that received pADA co-immunization (FIG. 4). These animals had statistically significant decreases in serum ANA compared to animals receiving envelope DNA immunogens Previous HIV clinical trials have demonstrated that heterologous prime-boost vaccination regimens will be most effective at generating protective responses. These regimens require multiple immunizations with different formulations given over a prolonged period. We have recently demonstrated that simultaneous DNA-protein immunization improved env-specific humoral responses compared to protein-only immunizations[38]. Thus, we sought to determine if addition of molecular ADA-1 to the DNA arm of a DNA-protein co-immunization regimen would improve antibody responses compared to envelope DNA and protein alone.

Indeed, addition of pADA to the envelope DNA arm, and simultaneous co-delivery of protein-in-adjuvant, significantly increased HIV-specific IgG in the serum of vaccinated animals (FIG. 5D) compared to those which received envelope DNA alone, DNA and protein, or DNA and pADA without protein. Interestingly in this experiment, while DNA, pADA, and protein together significantly enhanced serum IgG, we detected significant increases in $T_{FH}$ frequencies in the DLNs of the protein-vaccinated limb of all animals which received protein, irrespective of co-immunization with pADA (FIG. 6). These data verify that protein and aluminum adjuvant formulations increase $T_{FH}$ cell frequency; however, the enhanced frequency of $T_{FH}$ cells induced by protein-in-alum without pADA did not result in significant enhancement of serum IgG in our experiments. This indicates that pADA enhanced the function of $T_{FH}$ cells as measured by antigen-binding antibody. The data indicate that this is due to increased survivability of antigen-specific $T_{FH}$ cells and not necessarily increased proliferation of these cells which would explain the similar frequencies of $T_{FH}$ between groups that received protein with and without pADA. Recent elegant experiments indeed suggest that antigen availability is the primary driver for the plasma cell fate choice in the GC[55] and as DNA vaccine-transformed cells would likely be expressing both ADA-1 and env immunogens in the local DLN GCs, this directly impacts plasma cell differentiation. However, other factors such as the strength of T:B interactions[5] and CD40 signaling[57, 58] can also affect plasma cell differentiation.

The development of HIV neutralizing antibodies only in the sera of mice immunized with the triple combination of pCAP257 (gp160), pADA, and CAP257 gp140 glycoprotein, but not in those mice receiving pCAP257 (gp160) and matched glycoprotein gp140 without pADA (FIG. 8), further indicates that pADA promotes enhanced $T_{FH}$ function in vivo. These data indicate that pADA enhances the functional output of the GC, namely the development of neutralizing antibodies. These results not only strongly support the use of pADA as a vaccine adjuvant to enhance humoral responses and T cell function, but also have applications for therapeutic interventions for SCID and autoimmune patients. Finally, as PEGylated ADA-1 is approved for the treatment of SCID patients and has an established safety and tolerability profile in the clinic, the use of ADA-1 to adjuvant vaccine-induced responses represents a novel application of an extant therapy with the potential to be fast-tracked for clinical application.

REFERENCES CITED IN EXAMPLE 1

1. Buckley R H: Molecular defects in human severe combined immunodeficiency and approaches to immune reconstitution. *Annu Rev Immunol* 2004, 22:625-655.
2. Franco R, Pacheco R, Gatell J M, Gallart T, Lluis C: Enzymatic and extraenzymatic role of adenosine deaminase 1 in T-cell-dendritic cell contacts and in alterations of the immune function. *Critical Reviews™ in Immunology* 2007, 27(6).
3. Pacheco R, Martinez-Navio J, Lejeune M, Climent N, Oliva H, Gatell J, Gallart T, Mallol J, Lluis C, Franco R: CD26, adenosine deaminase, and adenosine receptors mediate costimulatory signals in the immunological synapse. *Proceedings of the National Academy of Sciences* 2005, 102(27):9583-9588.
4. Tardif V, Muir R, Cubas R, Chakhtoura M, Wilkinson P, Metcalf T, Herro R, Haddad E K: Adenosine deaminase-1 delineates human follicular helper T cell function and is altered with HIV. *Nature communications* 2019, 10(1): 823.
5. Casanova V, Naval-Macabuhay I, Massanella M, Rodrfguez-Garcifa M, Blanco J, Gatell J M, Garcfa F, Gallart T, Lluis C, Mallol J: Adenosine deaminase enhances the immunogenicity of human dendritic cells from healthy and HIV-infected individuals. *PloS one* 2012, 7(12):e51287.
6. Schmitt N, Morita R, Bourdery L, Bentebibel S E, Zurawski S M, Banchereau J, Ueno H: Human dendritic cells induce the differentiation of interleukin-21-producing T follicular helper-like cells through interleukin-12. *Immunity* 2009, 31(1):158-169.
7. Chakarov S, Fazilleau N: Monocyte-derived dendritic cells promote T follicular helper cell differentiation. *EMBO molecular medicine* 2014, 6(5):590-603.
8. Ballesteros-Tato A, Randall T D: Priming of T follicular helper cells by dendritic cells. *Immunology and cell biology* 2014, 92(1):22-27.
9. León B, Ballesteros-Tato A, Browning J L, Dunn R, Randall T D, Lund F E: Regulation of T H 2 development by CXCR5+ dendritic cells and lymphotoxin-expressing B cells. *Nature immunology* 2012, 13(7):681.
10. Havenar-Daughton C, Carnathan D G, de la Pefa A T, Pauthner M, Briney B, Reiss S M, Wood J S, Kaushik K, van Gils M J, Rosales S L: Direct probing of germinal center responses reveals immunological features and bottlenecks for neutralizing antibody responses to HIV Env trimer. *Cell reports* 2016, 17(9):2195-2209.
11. Hu J K, Crampton J C, Cupo A, Ketas T, van Gils M J, Sliepen K, de Taeye S W, Sok D, Ozorowski G, Deresa I: Murine antibody responses to cleaved soluble HIV-1 envelope trimers are highly restricted in specificity. *Journal of virology* 2015, 89(20):10383-10398.
12. Yan J, Yoon H, Kumar S, Ramanathan M P, Corbitt N, Kutzler M, Dai A, Boyer J D, Weiner D B: Enhanced cellular immune responses elicited by an engineered HIV-1 subtype B consensus-based envelope DNA vaccine. *Molecular Therapy* 2007, 15(2):411-421.
13. Desrosiers M D, Cembrola K M, Fakir M J, Stephens L A, Jama F M, Shameli A, Mehal W Z, Santamaria P, Shi Y: Adenosine deamination sustains dendritic cell activation in inflammation. *The Journal of Immunology* 2007, 179(3):1884-1892.
14. Choi Y S, Kageyama R, Eto D, Escobar T C, Johnston R J, Monticelli L, Lao C, Crotty S: ICOS receptor instructs T follicular helper cell versus effector cell differentiation via induction of the transcriptional repressor Bcl6. *Immunity* 2011, 34(6):932-946.
15. Choi Y S, Kageyama R, Eto D, Escobar T C, Johnston R J, Monticelli L, Lao C, Crotty S: Bcl6 dependent T follicular helper cell differentiation diverges from effector cell differentiation during priming and depends on the gene Icos. *Immunity* 2011, 34(6):932.
16. Choi Y S, Yang J A, Crotty S: Dynamic regulation of Bcl6 in follicular helper CD4 T (Tfh) cells. *Current opinion in immunology* 2013, 25(3):366-372.
17. Crotty S: T follicular helper cell differentiation, function, and roles in disease. *Immunity* 2014, 41(4):529-542.
18. Pedros C, Zhang Y, Hu J K, Choi Y S, Canonigo-Balancio A J, Yates III JR, Altman A, Crotty S, Kong K-F: A TRAF-like motif of the inducible costimulator ICOS controls development of germinal center T FH cells via the kinase TBK1. *Nature immunology* 2016, 17(7):825.
19. Weinstein J S, Bertino S A, Hernandez S G, Poholek A C, Teplitzky T B, Nowyhed H N, Craft J: B cells in T follicular helper cell development and function: separable roles in delivery of ICOS ligand and antigen. *The Journal of Immunology* 2014, 192(7):3166-3179.
20. Blanco P, Palucka A K, Pascual V, Banchereau J: Dendritic cells and cytokines in human inflammatory and autoimmune diseases. *Cytokine & growth factor reviews* 2008, 19(1):41-52.
21. Chavele K-M, Merry E, Ehrenstein M R: Cutting edge: circulating plasmablasts induce the differentiation of human T follicular helper cells via IL-6 production. *The Journal of Immunology* 2015, 194(6):2482-2485.
22. Eto D, Lao C, DiToro D, Barnett B, Escobar T C, Kageyama R, Yusuf I, Crotty S: IL-21 and IL-6 are critical for different aspects of B cell immunity and redundantly induce optimal follicular helper CD4 T cell (Tfh) differentiation. *PloS one* 2011, 6(3):e17739.
23. Papillion A M, Bachus H, Fuller M, León B, Ballesteros-Tato A: IL-6 counteracts IL-2-dependent suppression of T follicular helper cell responses. In.: Am Assoc Immnol; 2018.
24. Choi Y S, Eto D, Yang J A, Lao C, Crotty S: Cutting edge: STAT1 is required for IL-6-mediated Bcl6 induction for early follicular helper cell differentiation. *The Journal of Immunology* 2013, 190(7):3049-3053.
25. Wu X-B, Cao D-L, Zhang X, Jiang B-C, Zhao L-X, Qian B, Gao Y-J: CXCL13/CXCR5 enhances sodium channel Nav1.8 current density via p38 MAP kinase in primary sensory neurons following inflammatory pain. *Scientific reports* 2016, 6:34836.
26. Cucak H, Yrlid U, Reizis B, Kalinke U, Johansson-Lindbom B: Type I interferon signaling in dendritic cells stimulates the development of lymph-node-resident T follicular helper cells. *Immunity* 2009, 31(3):491-501.
27. Ritvo P-G, Klatzmann D: Interleukin-1 in the response of follicular helper and follicular regulatory T cells. *Frontiers in immunology* 2019, 10.
28. Schmitt N, Bustamante J, Bourdery L, Bentebibel S E, Boisson-Dupuis S, Hamlin F, Tran M V, Blankenship D, Pascual V, Savino D A: IL-12 receptor β1 deficiency alters in vivo T follicular helper cell response in humans. *Blood* 2013, 121(17):3375-3385.
29. Martinez V, Costagliola D, Bonduelle O, N'go N, Schnuriger A, Thodorou I, Clauvel J-P, Sicard D, Agut H, Debr P: Combination of HIV-1-specific CD4 Th1 cell responses and IgG2 antibodies is the best predictor for persistence of long-term nonprogression. *Journal of Infectious Diseases* 2005, 191(12):2053-2063.
30. Ngo-Giang-Huong N, Candotti D, Goubar A, Autran B, Maynart M, Sicard D, Clauvel J-P, Agut H, Costagliola D, Rouzioux C: HIV type 1-specific IgG2 antibodies: markers of helper T cell type 1 response and prognostic marker of long-term nonprogression. *AIDS research and human retroviruses* 2001, 17(15):1435-1446.
31. Zhu C, Ma J, Liu Y, Tong J, Tian J, Chen J, Tang X, Xu H, Lu L, Wang S: Increased frequency of follicular helper T cells in patients with autoimmune thyroid disease. *The Journal of Clinical Endocrinology & Metabolism* 2012, 97(3):943-950.
32. Linterman M A, Rigby R J, Wong R K, Yu D, Brink R, Cannons J L, Schwartzberg P L, Cook M C, Walters G D, Vinuesa C G: Follicular helper T cells are required for systemic autoimmunity. *Journal of Experimental Medicine* 2009, 206(3):561-576.
33. Morita R, Schmitt N, Bentebibel S-E, Ranganathan R, Bourdery L, Zurawski G, Foucat E, Dullaers M, Oh S, Sabzghabaei N: Human blood CXCR5+CD4+ T cells are counterparts of T follicular cells and contain specific subsets that differentially support antibody secretion. *Immunity* 2011, 34(1):108-121.
34. Lu S: Heterologous prime-boost vaccination. *Current opinion in immunology* 2009, 21(3):346-351.
35. Wang S, Kennedy J S, West K, Montefiori D C, Coley S, Lawrence J, Shen S, Green S, Rothman A L, Ennis F A: Cross-subtype antibody and cellular immune responses induced by a polyvalent DNA prime-protein boost HIV-1 vaccine in healthy human volunteers. *Vaccine* 2008, 26(31):3947-3957.
36. Letvin N L, Montefiori D C, Yasutomi Y, Perry H C, Davies M-E, Lekutis C, Alroy M, Freed D C, Lord C I, Handt L K: Potent, protective anti-HIV immune responses generated by bimodal HIV envelope DNA plus protein vaccination. *Proceedings of the National Academy of Sciences* 1997, 94(17):9378-9383.
37. van Diepen M T, Chapman R, Douglass N, Galant S, Moore P L, Margolin E, Ximba P, Morris L, Rybicki E P, Williamson A-L: Prime-boost immunizations with DNA, modified vaccinia virus Ankara, and protein-based vaccines elicit robust HIV-1 tier 2 neutralizing antibodies against the CAP256 superinfecting virus. *Journal of Virology* 2019, 93(8):e02155-02118.
38. Pissani F, Malherbe D C, Schuman J T, Robins H, Park B S, Krebs S J, Barnett S W, Haigwood N L: Improvement of antibody responses by HIV envelope DNA and protein co-immunization. *Vaccine* 2014, 32(4):507-513.
39. Wibmer C K, Bhiman J N, Gray E S, Tumba N, Karim S S A, Williamson C, Morris L, Moore P L: Viral escape from HIV-1 neutralizing antibodies drives increased plasma neutralization breadth through sequential recognition of multiple epitopes and immunotypes. *PLoS pathogens* 2013, 9(10):e1003738.
40. Crotty S: Follicular helper CD4 T cells (Tfh). *Annual review of immunology* 2011, 29:621-663.
41. Binley J M, Wrin T, Korber B, Zwick M B, Wang M, Chappey C, Stiegler G, Kunert R, Zolla-Pazner S, Katinger H: Comprehensive cross-clade neutralization analysis of a panel of anti-human immunodeficiency virus type 1 monoclonal antibodies. *Journal of virology* 2004, 78(23):13232-13252.
42. Kepler T B, Liao H-X, Alam S M, Bhaskarabhatla R, Zhang R, Yandava C, Stewart S, Anasti K, Kelsoe G, Parks R: Immunoglobulin gene insertions and deletions in the affinity maturation of HIV-1 broadly reactive neutralizing antibodies. *Cell host & microbe* 2014, 16(3):304-313.
43. Klein F, Diskin R, Scheid J F, Gaebler C, Mouquet H, Georgiev I S, Pancera M, Zhou T, Incesu R-B, Fu B Z: Somatic mutations of the immunoglobulin framework are generally required for broad and potent HIV-1 neutralization. *Cell* 2013, 153(1):126-138.
44. Locci M, Havenar-Daughton C, Landais E, Wu J, Kroenke M A, Arlehamn C L, Su L F, Cubas R, Davis M M, Sette A: Human circulating PD-1+ CXCR3− CXCR5+ memory Tfh cells are highly functional and correlate with broadly neutralizing HIV antibody responses. *Immunity* 2013, 39(4):758-769.
45. Franco R, Valenzuela A, Lluis C, Blanco J: Enzymatic and extraenzymatic role of ecto-adenosine deaminase in lymphocytes. *Immunological reviews* 1998, 161(1):27-42.
46. Ogata M, Ito T, Shimamoto K, Nakanishi T, Satsutani N, Miyamoto R, Nomura S: Plasmacytoid dendritic cells have a cytokine-producing capacity to enhance ICOS ligand-mediated IL-10 production during T-cell priming. *International immunology* 2012, 25(3):171-182.

47. Ma C S, Suryani S, Avery D T, Chan A, Nanan R, Santner-Nanan B, Deenick E K, Tangye S G: Early commitment of naïve human CD4+ T cells to the T follicular helper (TFH) cell lineage is induced by IL-12. *Immunology and cell biology* 2009, 87(8):590-600.
48. Oestreich K J, Mohn S E, Weinmann A S: Molecular mechanisms that control the expression and activity of Bcl-6 in T H 1 cells to regulate flexibility with a T FH-like gene profile. *Nature immunology* 2012, 13(4):405.
49. McDonald K G, McDonough J S, Dieckgraefe B K, Newberry R D: Dendritic cells produce CXCL13 and participate in the development of murine small intestine lymphoid tissues. *The American journal of pathology* 2010, 176(5):2367-2377.
50. Cai G, Nie X, Zhang W, Wu B, Lin J, Wang H, Jiang C, Shen Q: A regulatory role for IL-10 receptor signaling in development and B cell help of T follicular helper cells in mice. *The Journal of Immunology* 2012, 189(3):1294-1302.
51. Avery D T, Bryant V L, Ma C S, de Waal Malefyt R, Tangye S G: IL-21-induced isotype switching to IgG and IgA by human naive B cells is differentially regulated by IL-4. *The Journal of Immunology* 2008, 181(3):1767-1779.
52. Lim H W, Hillsamer P, Banham A H, Kim C H: Cutting edge: direct suppression of B cells by CD4+ CD25+ regulatory T cells. *The Journal of Immunology* 2005, 175(7):4180-4183.
53. Rahim S S, Khan N, Boddupalli C S, Hasnain S E, Mukhopadhyay S: Interleukin-10 (IL-10) mediated suppression of IL-12 production in RAW 264.7 cells also involves c-rel transcription factor. *Immunology* 2005, 114(3):313-321.
54. Brigida I, Sauer A V, Ferrua F, Giannelli S, Scaramuzza S, Pistoia V, Castiello M C, Barendregt B H, Cicalese M P, Casiraghi M: B-cell development and functions and therapeutic options in adenosine deaminase-deficient patients. *Journal of Allergy and Clinical Immunology* 2014, 133(3):799-806. e710.
55. Krautler N J, Suan D, Butt D, Bourne K, Hermes J R, Chan T D, Sundling C, Kaplan W, Schofield P, Jackson J: Differentiation of germinal center B cells into plasma cells is initiated by high-affinity antigen and completed by Tfh cells. *Journal of Experimental Medicine* 2017, 214 (5):1259-1267.
56. Ise W, Fujii K, Shiroguchi K, Ito A, Kometani K, Takeda K, Kawakami E, Yamashita K, Suzuki K, Okada T: T follicular helper cell-germinal center B cell interaction strength regulates entry into plasma cell or recycling germinal center cell fate. *Immunity* 2018, 48(4):702-715. e704.
57. Ise W, Kurosaki T: Plasma cell differentiation during the germinal center reaction. *Immunological reviews* 2019, 288(1):64-74.
58. Suan D, Sundling C, Brink R: Plasma cell and memory B cell differentiation from the germinal center. *Current opinion in immunology* 2017, 45:97-102.
59. Yan J, Corbitt N, Pankhong P, Shin T, Khan A, Sardesai N Y, Weiner D B: Immunogenicity of a novel engineered HIV-1 clade C synthetic consensus-based envelope DNA vaccine. *Vaccine* 2011, 29(41):7173-7181.
60. Muthumani K, Zhang D, Dayes N S, Hwang D S, Calarota S A, Choo A Y, Boyer J D, Weiner D B: Novel engineered HIV-1 East African Clade-A gp160 plasmid construct induces strong humoral and cell-mediated immune responses in vivo. *Virology* 2003, 314(1):134-146.
61. Malherbe D C, Doria-Rose N A, Misher L, Beckett T, Puryear W B, Schuman J T, Kraft Z, O'Malley J, Mori M, Srivastava I: Sequential immunization with a subtype B HIV-1 envelope quasispecies partially mimics the in vivo development of neutralizing antibodies. *Journal of virology* 2011, 85(11):5262-5274.
62. Sellhorn G, Caldwell Z, Mineart C, Stamatatos L: Improving the expression of recombinant soluble HIV Envelope glycoproteins using pseudo-stable transient transfection. *Vaccine* 2009, 28(2):430-436.
63. Montefiori D C: Measuring HIV neutralization in a luciferase reporter gene assay. In: *HIV protocols.* Springer; 2009: 395-405.

Example 2: Mouse and Human ADA DNA Constructs Express In Vitro

Figure 13A:
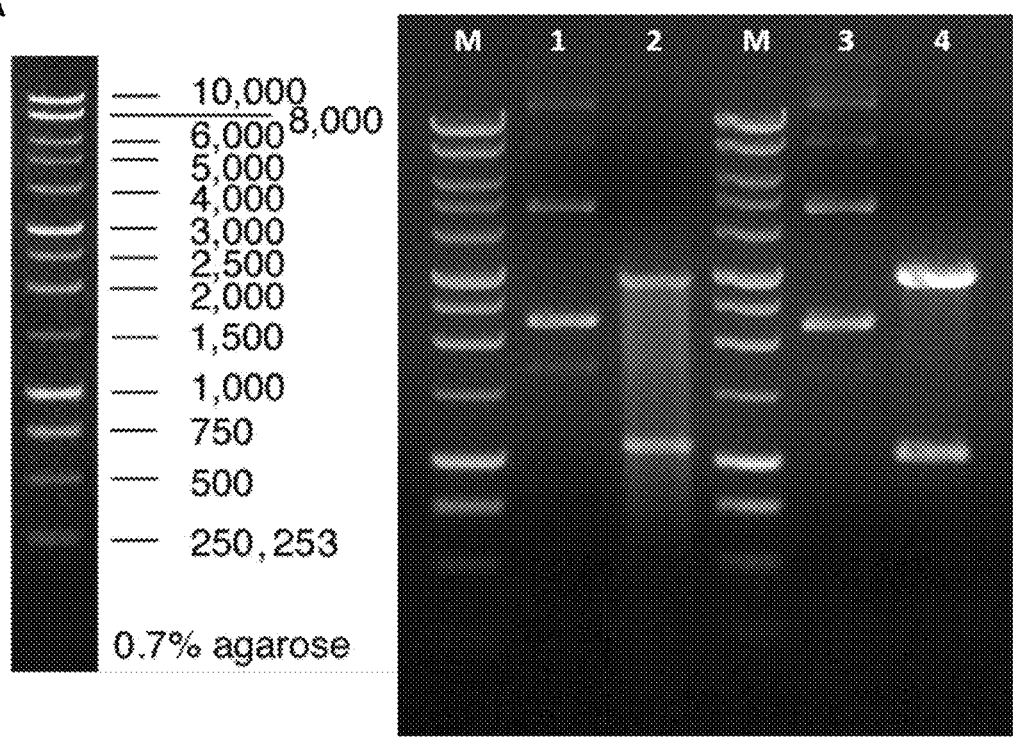
FIG. 13A-13C. In vitro validation and expression of mouse and human adenosine deaminase DNA constructs.
Figure 13B:
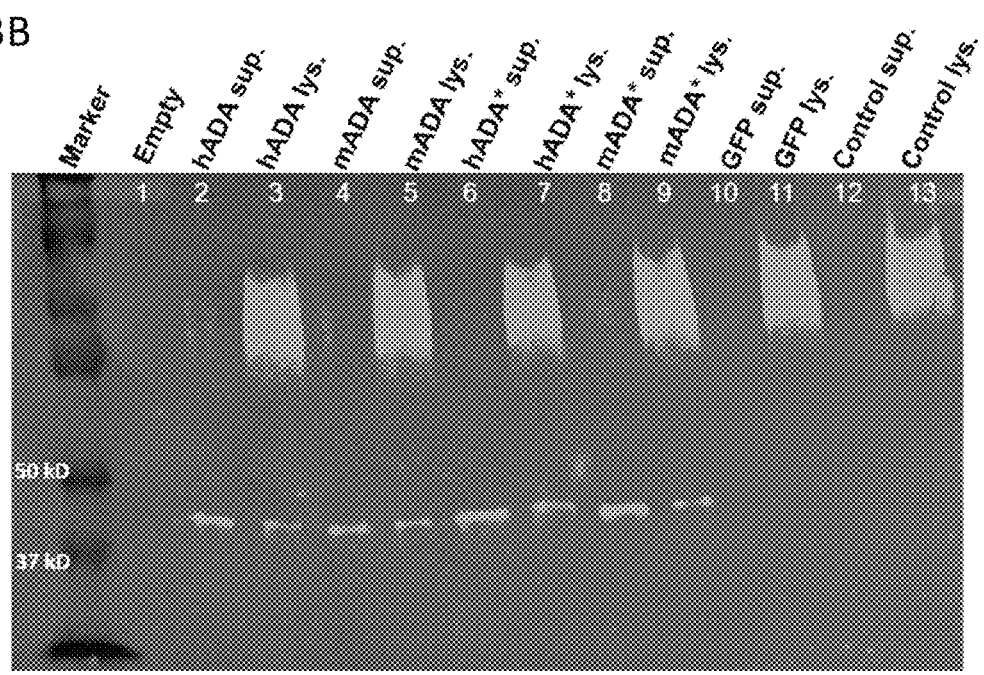
Figure 13C:
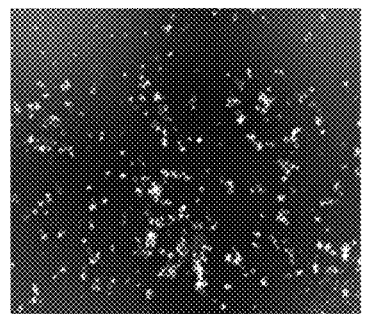

The coding sequences for *Mus musculus* (NCBI reference sequence NM_001272052.1) and *Homo sapiens* (NCBI reference sequence NM_000022.4) ADA1 were codon optimized for mammalian expression and cloned into the pVAX vector (Thermo Fisher) for expression at Genescript (Piscataway, NJ). The presence of the supercoiled 1,080 bp ADA insert was detected in both constructs (FIG. 13A). Next, we transfected 293T cells using lipofectamine (Thermo Fisher) in order to confirm expression in mammalian cells. We detected the ~41 kD ADA protein by western blot in both the supernatant and lysate of both human and mouse ADA-transfected cells (FIG. 13) but not in either the supernatant or lysate of GFP-transfected cells which was used a positive control for transfection (FIG. 13B-13C). These data demonstrate that the pVAX construct successfully expresses both mouse and human ADA protein in mammalian cells.

ADA_HUMANAdenosinedeaminase

SEQ ID NO: 1

ATGGCGCAAACCCCGGCGTTCGATAAGCCGAAAGTGGAGCTGCATGTTCATCTGGAC

GGTAGCATCAAACCGGAA

ACCATTCTGTATTATGGTCGTCGTCGTGGTATTGCGCTGCCGGCGAACACCGCGGAA

GGTCTGCTGAACGTGATT

GGCATGGACAAGCCGCTGACCCTGCCGGACTTCCTGGCGAAATTTGATTACTATATG

CCGGCGATTGCGGGTTGC

CGTGAGGCGATCAAGCGTATTGCGTATGAGTTCGTGGAGATGAAGGCGAAAGAAGG

TGTGGTTTACGTTGAGGTG

-continued

```
CGCTATAGCCCGCACCTGCTGGCGAACAGCAAAGTTGAACCGATCCCGTGGAACCAA

GCGGAAGGCGACCTGACC

CCGGATGAGGTGGTTGCGCTGGTTGGTCAAGGCCTGCAGGAAGGTGAACGTGATTTT

GGCGTTAAGGCGCGTAGC

ATTCTGTGCTGCATGCGTCACCAGCCGAACTGGAGCCCGAAAGTGGTTGAACTGTGC

AAGAAATACCAGCAACAG

ACCGTGGTTGCGATCGACCTGGCGGGTGATGAAACCATCCCGGGCAGCAGCCTGCTG

CCGGGTCATGTGCAAGCG

TATCAGGAAGCGGTTAAGAGCGGTATCCACCGTACCGTGCATGCGGGTGAGGTTGGC

AGCGCGGAAGTGGTTAAA

GAGGCGGTGGACATTCTGAAAACCGAACGTCTGGGTCACGGCTACCACACCCTGGA

GGATCAAGCGCTGTATAAC

CGTCTGCGTCAGGAAAACATGCACTTCGAGATTTGCCCGTGGAGCAGCTATCTGACC

GGTGCGTGGAAGCCGGAC

ACCGAACACGCGGTTATCCGTCTGAAAAACGATCAAGCGAACTACAGCCTGAACAC

CGACGATCCGCTGATTTTC

AAGAGCACCCTGGACACCGATTATCAGATGACCAAACGTGACATGGGTTTCACCGAG

GAAGAGTTTAAGCGTCTG

AACATTAACGCGGCGAAAAGCAGCTTTCTGCCGGAAGATGAGAAACGTGAGCTGCT

GGACCTGCTGTATAAAGCG

TATGGTATGCCGCCGAGCGCGAGCGCGGGCCAAAATCTG

ADA_HUMANAdenosinedeaminase
                                                   SEQ ID NO: 2
MAQTPAFDKPKVELHVHLDGSIKPETILYYGRRRGIALPANTAEGLLNVIGMDKPLTLPD

FLAKFDYYMPAIAGCREAIKRIAYEFVEMKAKEGVVYVEVRYSPHLLANSKVEPIPWNQ

A

EGDLTPDEVVALVGQGLQEGERDFGVKARSILCCMRHQPNWSPKVVELCKKYQQQTVV

AI

DLAGDETIPGSSLLPGHVQAYQEAVKSGIHRTVHAGEVGSAEVVKEAVDILKTERLGHG

Y

HTLEDQALYNRLRQENMHFEICPWSSYLTGAWKPDTEHAVIRLKNDQANYSLNTDDPLI

F

KSTLDTDYQMTKRDMGFTEEEFKRLNINAAKSSFLPEDEKRELLDLLYKAYGMPPSASA

G

QNL

ADA_MOUSEAdenosinedeaminase
                                                   SEQ ID NO: 3
ATGGCGCAAACCCCGGCGTTCAATAAACCGAAAGTGGAGCTGCACGTTCATCTGGAC

GGCGCGATTAAACCGGAG

ACCATTCTGTATTTCGGTAAGAAACGTGGTATTGCGCTGCCGGCGGACACCGTGGAG

GAACTGCGTAACATCATT

GGCATGGATAAGCCGCTGAGCCTGCCGGGTTTCCTGGCGAAATTTGACTACTATATG
```

-continued

```
CCGGTGATTGCGGGCTGC

CGTGAAGCGATCAAGCGTATTGCGTACGAATTTGTTGAGATGAAGGCGAAAGAAGG

TGTGGTTTACGTTGAGGTG

CGCTATAGCCCGCACCTGCTGGCGAACAGCAAAGTTGATCCGATGCCGTGGAACCAA

ACCGAGGGTGATGTGACC

CCGGATGATGTGGTTGATCTGGTTAACCAGGGTCTGCAAGAAGGCGAGCAGGCGTTC

GGTATCAAAGTGCGTAGC

ATTCTGTGCTGCATGCGTCACCAACCGAGCTGGAGCCTGGAAGTTCTGGAGCTGTGC

AAGAAATACAACCAGAAA

ACCGTGGTTGCGATGGACCTGGCGGGTGATGAAACCATCGAGGGCAGCAGCCTGTTT

CCGGGTCACGTGGAAGCG

TATGAGGGTGCGGTTAAGAACGGCATTCACCGTACCGTGCATGCGGGTGAAGTTGGC

AGCCCGGAAGTGGTTCGT

GAGGCGGTGGACATCCTGAAAACCGAGCGTGTTGGTCACGGCTACCACACCATTGAA

GATGAGGCGCTGTATAAC

CGTCTGCTGAAGGAAAACATGCACTTCGAGGTGTGCCCGTGGAGCAGCTATCTGACC

GGTGCGTGGGACCCGAAA

ACCACCCACGCGGTGGTTCGTTTCAAGAACGATAAAGCGAACTACAGCCTGAACACC

GACGATCCGCTGATCTTT

AAGAGCACCCTGGACACCGATTATCAGATGACCAAGAAAGACATGGGTTTCACCGA

GGAAGAGTTTAAGCGTCTG

AACATTAACGCGGCGAAAAGCAGCTTTCTGCCGGAAGAGGAGAAGAAGGAACTGCT

GGAACGCCTGTATCGTGAG

TATCAG
```

ADA_MOUSE Adenosine deaminase
SEQ ID NO: 4

```
MAQTPAFNKPKVELHVHLDGAIKPETILYFGKKRGIALPADTVEELRNIIGMDKPLSLPG

FLAKFDYYMPVIAGCREAIKRIAYEFVEMKAKEGVVYVEVRYSPHLLANSKVDPMPWN

QT

EGDVTPDDVVDLVNQGLQEGEQAFGIKVRSILCCMRHQPSWSLEVLELCKKYNQKTVV

AM

DLAGDETIEGSSLFPGHVEAYEGAVKNGIHRTVHAGEVGSPEVVREAVDILKTERVGHG

Y

HTIEDEALYNRLLKENMHFEVCPWSSYLTGAWDPKTTHAVVRFKNDKANYSLNTDDPL

IF

KSTLDTDYQMTKKDMGFTEEEFKRLNINAAKSSFLPEEEKKELLERLYREYQ
```

Our final plasmid construct with its IgE leader
SEQ ID NO: 5

```
MDWTWILFLVAAATRVHS

AQTPAFNKPKVELHVHLDGAIKPETILYFGKKRGIALPADTVEELRNIIGMDKPLSLPG

FLAKFDYYMPVIAGCREAIKRIAYEFVEMKAKEGVVYVEVRYSPHLLANSKVDPMPWNQT

EGDVTPDDVVDLVNQGLQEGEQAFGIKVRSILCCMRHQPSWSLEVLELCKKYNQKTVVAM

DLAGDETIEGSSLFPGHVEAYEGAVKNGIHRTVHAG:VGSPEVVREAVDILKTERVGHGY
```

HTIEDEALYNRLLKENMHFEVCPWSSYLTGAWDPKTTHAVVRFKNDKANYSLNTDDPLIF

KSTLDTDYQMTKKDMGFTEEEFKRLNINAAKSSFLPEEEKKELLERLYREYQ

Wildtype mouse ADA:
SEQ ID NO: 6
MAQTPAFNKPKVELHVHLDGAIKPETILYFGKKRGIALPADTVEELRNIIGMDKPLSLPG

FLAKFDYYMPVIAGCREAIKRIAYEFVEMKAKEGVVYVEVRYSPHLLANSKVDPMPWNQT

EGDVTPDDVVDLVNQGLQEGEQAFGIKVRSILCCMRHQPSWSLEVLELCKKYNQKTVVAM

DLAGDETIEGSSLFPGHVEAYEGAVKNGIHRTVHAG :VGSPEVVREAVDILKTERVGHGY

HTIEDEALYNRLLKENMHFEVCPWSSYLTGAWDPKTTHAVVRFKNDKANYSLNTDDPLIF

KSTLDTDYQMTKKDMGFTEEEFKRLNINAAKSSFLPEEEKKELLERLYREYQ

MutantADA:
SEQ ID NO: 7
MAQTPAFNKPKVELHVHLDGAIKPETILYFGKKRGIALPADTVEELRNIIGMDKPLSLPG

FLAKFDYYMPVIAGCREAIKRIAYEFVEMKAKEGVVYVEVRYSPHLLANSKVDPMPWNQT

EGDVTPDDVVDLVNQGLQEGEQAFGIKVRSILCCMRHQPSWSLEVLELCKKYNQKTVVAM

DLAGDETIEGSSLFPGHVEAYEGAVKNGIHRTVHAG :VGSPEVVREAVDILKTERVGHGY

HTIEDEALYNRLLKENMHFEVCPWSSYLTGAWDPKTTHAVVRFKNDKANYSLNTDDPLIF

KSTLDTDYQMTKKDMGFTEEEFKRLNINAAKSSFLPEEEKKELLERLYREYQ

IgE-hADA-1
SEQ ID NO: 8
MDWTWILFLVAAATRVHS

AQTPAFDKPKVELHVHLDGSIKPETILYYGRRRGIALPANTAEGLLNVIGMDKPLTLPD

FLAKFDYYMPAIAGCREAIKRIAYEFVEMKAKEGVVYVEVRYSPHLLANSKVEPIPWNQA

EGDLTPDEVVALVGQGLQEGERDFGVKARSILCCMRHQPNWSPKVVELCKKYQQQTVVAI

DLAGDETIPGSSLLPGHVQAYQEAVKSGIHRTVHAGEVGSAEVVKEAVDILKTERLGHGY

HTLEDQALYNRLRQENMHFEICPWSSYLTGAWKPDTEHAVIRLKNDQANYSLNTDDPLIF

KSTLDTDYQMTKRDMGFTEEEFKRLNINAAKSSFLPEDEKRELLDLLYKAYGMPPSASAG

QNL

Pvax vector sequence
SEQ ID NO: 9
GACTCTTCGCGATGTACGGGCCAGATATACGCGTTGACATTGATTATTGACTAGTTATTAATAGTAATCA

ATTACGGGGTCATTAGTTCATAGCCCATATATGGAGTTCCGCGTTACATAACTTACGGTAAATGGCCCGC

CTGGCTGACCGCCCAACGACCCCCGCCCATTGACGTCAATAATGACGTATGTTCCCATAGTAACGCCAAT

AGGGACTTTCCATTGACGTCAATGGGTGGACTATTTACGGTAAACTGCCCACTTGGCAGTACATCAAGTG

TATCATATGCCAAGTACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCTATTACCATGGTGAT

GCGGTTTTGGCAGTACATCAATGGGCGTGGATAGCGGTTTGACTCACGGGGATTTCCAAGTCTCCACCCC

ATTGACGTCAATGGGAGTTTGTTTTGGCACCAAAATCAACGGGACTTTCCAAAATGTCGTAACAACTCCG

CCCCATTGACGCAAATGGGCGGTAGGCGTGTACGGTGGGAGGTCTATATAAGCAGAGCTCTCTGGCTAAC

TAGAGAACCCACTGCTTACTGGCTTATCGAAATTAATACGACTCACTATAGGGAGACCCAAGCTGGCTAG

CGTTTAAACTTAAGCTTGGTACCGAGCTCGGATCCACTAGTCCAGTGTGGTGGAATTCTGCAGATATCCA

GCACAGTGGCGGCCGCTCGAGTCTAGAGGGCCCGTTTAAACCCGCTGATCAGCCTCGACTGTGCCTTCTA

GTTGCCAGCCATCTGTTGTTTGCCCCTCCCCCGTGCCTTCCTTGACCCTGGAAGGTGCCACTCCCACTGT

CCTTTCCTAATAAAATGAGGAAATTGCATCGCATTGTCTGAGTAGGTGTCATTCTATTCTGGGGGGTGGG

```
-continued
GTGGGGCAGGACAGCAAGGGGGAGGATTGGGAAGACAATAGCAGGCATGCTGGGGATGCGGTGGGCTCTA

TGGCTTCTACTGGGCGGTTTTATGGACAGCAAGCGAACCGGAATTGCCAGCTGGGGCGCCCTCTGGTAAG

GTTGGGAAGCCCTGCAAAGTAAACTGGATGGCTTTCTCGCCGCCAAGGATCTGATGGCGCAGGGGATCAA

GCTCTGATCAAGAGACAGGATGAGGATCGTTTCGCATGATTGAACAAGATGGATTGCACGCAGGTTCTCC

GGCCGCTTGGGTGGAGAGGCTATTCGGCTATGACTGGGCACAACAGACAATCGGCTGCTCTGATGCCGCC

GTGTTCCGGCTGTCAGCGCAGGGGCGCCCGGTTCTTTTTGTCAAGACCGACCTGTCCGGTGCCCTGAATG

AACTGCAAGACGAGGCAGCGCGGCTATCGTGGCTGGCCACGACGGGCGTTCCTTGCGCAGCTGTGCTCGA

CGTTGTCACTGAAGCGGGAAGGGACTGGCTGCTATTGGGCGAAGTGCCGGGGCAGGATCTCCTGTCATCT

CACCTTGCTCCTGCCGAGAAAGTATCCATCATGGCTGATGCAATGCGGCGGCTGCATACGCTTGATCCGG

CTACCTGCCCATTCGACCACCAAGCGAAACATCGCATCGAGCGAGCACGTACTCGGATGGAAGCCGGTCT

TGTCGATCAGGATGATCTGGACGAAGAGCATCAGGGGCTCGCGCCAGCCGAACTGTTCGCCAGGCTCAAG

GCGAGCATGCCCGACGGCGAGGATCTCGTCGTGACCCATGGCGATGCCTGCTTGCCGAATATCATGGTGG

AAAATGGCCGCTTTTCTGGATTCATCGACTGTGGCCGGCTGGGTGTGGCGGACCGCTATCAGGACATAGC

GTTGGCTACCCGTGATATTGCTGAAGAGCTTGGCGGCGAATGGGCTGACCGCTTCCTCGTGCTTTACGGT

ATCGCCGCTCCCGATTCGCAGCGCATCGCCTTCTATCGCCTTCTTGACGAGTTCTTCTGAATTATTAACG

CTTACAATTTCCTGATGCGGTATTTTCTCCTTACGCATCTGTGCGGTATTTCACACCGCATACAGGTGGC

ACTTTTCGGGGAAATGTGCGCGGAACCCCTATTTGTTTATTTTCTAAATACATTCAAATATGTATCCGC

TCATGAGACAATAACCCTGATAAATGCTTCAATAATAGCACGTGCTAAAACTTCATTTTTAATTTAAAAG

GATCTAGGTGAAGATCCTTTTTGATAATCTCATGACCAAAATCCCTTAACGTGAGTTTTCGTTCCACTGA

GCGTCAGACCCCGTAGAAAAGATCAAAGGATCTTCTTGAGATCCTTTTTTTCTGCGCGTAATCTGCTGCT

TGCAAACAAAAAAACCACCGCTACCAGCGGTGGTTTGTTTGCCGGATCAAGAGCTACCAACTCTTTTTCC

GAAGGTAACTGGCTTCAGCAGAGCGCAGATACCAAATACTGTCCTTCTAGTGTAGCCGTAGTTAGGCCAC

CACTTCAAGAACTCTGTAGCACCGCCTACATACCTCGCTCTGCTAATCCTGTTACCAGTGGCTGCTGCCA

GTGGCGATAAGTCGTGTCTTACCGGGTTGGACTCAAGACGATAGTTACCGGATAAGGCGCAGCGGTCGGG

CTGAACGGGGGGTTCGTGCACACAGCCCAGCTTGGAGCGAACGACCTACACCGAACTGAGATACCTACAG

CGTGAGCTATGAGAAAGCGCCACGCTTCCCGAAGGGAGAAAGGCGGACAGGTATCCGGTAAGCGGCAGGG

TCGGAACAGGAGAGCGCACGAGGGAGCTTCCAGGGGAAACGCCTGGTATCTTTATAGTCCTGTCGGGTT

TCGCCACCTCTGACTTGAGCGTCGATTTTTGTGATGCTCGTCAGGGGGCGGAGCCTATGGAAAAACGCC

AGCAACGCGGCCTTTTTACGGTTCCTGGGCTTTTGCTGGCCTTTTGCTCACATGTTCTT
```

Example 3: ADA-1 and COVID-19 Vaccine

SARS-CoV-2 emerged in late 2019 and caused a global pandemic termed coronavirus disease 2019 (COVID-19). Transmission rates are high and spread remains difficult to track. Therefore, control of this viral infection will be challenging without an effective vaccine to limit community spread. As the spike (S) glycoprotein of SARS-CoV-2 is the primary surface protein and mediates entry into host cells, it is a major target of neutralizing antibodies and is the antigenic focus of the DNA vaccine described herein. Our collaborators recently demonstrated that a S-targeted DNA vaccine construct is immunogenic in mice and guinea pigs, promotes neutralizing antibody formation, and inhibits binding to the SARS-CoV-2 cellular receptor[1]. Despite these promising results, the immunogenicity and durability of any SARS-COV-2 vaccine candidate in aged populations remains unknown.

Most COVID-19 deaths occur in patients over 65 years of age, a population that is known to have sub-optimal immune responses to vaccination. The reason for vaccine failure in older adults is multifactorial and includes suboptimal nutrition, compromised circulation, and most importantly impaired innate and adaptive immunity. These age-related alterations significantly impair the ability of older adults to develop protective immunity post-vaccination. Therefore, antigen and adjuvant formulations which enhance antigen-specific immunity in aged populations is a critical component of COVID-19 control measures. A mutant with a single point mutation at amino acid 614 in the spike protein (D614G) has become the dominant circulating strain in the United States and as such, responses to DNA antigens encoding the variant spike glycoprotein are utilized as the vaccine antigen.

Quality antibody responses depend upon T cell help. Follicular helper T cells ($T_{FH}$) are a unique cell population which promotes somatic hypermutation and affinity maturation of antigen-experienced B cells in lymph node germinal center (GCs). ADA-1 is critical to immune cell function and ADA-1 mutations induce sever-combined immunodeficiency (SCID) in humans. Pegylated bovine ADA is approved for use in SCID patients. In our previous experiment, we demonstrated that co-immunization with plasmid-encoded ADA-1 (pADA) and an HIV-1 DNA vaccine enhanced anti-HIV antibodies in mice and promoted neutralizing antibody formation in mice and macaques. Finally, there is evidence that ADA-1 activity decreases as human cells age, suggestive of a role for decreased ADA-1 function in aged immune responsiveness[4]. These preliminary findings indicate that pADA co-immunization represents a novel use of an FDA approved molecule as a molecular vaccine adjuvant that can enhance vaccine-induced responses which is especially important in aged populations which respond poorly to vaccination and are disproportionately affected by COVID-19 morbidity and mortality. Thus, co-immunization of pADA with SARS-COV-2 spike DNA antigens (pS) will enhance antigen-specific humoral and cell-mediated immunity in young and aged mice. This experiment:

1) Provides evidence demonstrating that pADA immune adjuvant improves the quality and persistence of humoral and T cell-mediated immunity to COVID-19 vaccine antigens in aged mice. Built on our reported findings that ADA-1 co-immunization results in antigen dose sparing, improved quality of anti-SARS-Co-V2 S1 antibody and broad T cellular responses to vaccine antigens, we test whether the immune adjuvant activity can rescue aging defects in immune priming, durability and memory. We characterize immune responses to pSD614G in young and aged mouse models, pADA co-immunization including antigen-specific antibody in the periphery and respiratory mucosa, lymph node GC $T_{FH}$, and T cell responses at both effector and memory timepoints.

2) Characterize the axis of ADA-1/CD26/A1/A2B activity in aging mice by examining the effect of ADA on the activities of innate pathways, increased breadth and somatic hypermutation of B cell receptor specificity, and association with functional GC-$T_{FH}$ and GC-B cells. We further characterize ADA-1 expression, enzymatic activity, and ADA-receptor expression levels in lymphocytes from healthy young and aged human donors and mouse cells. Lymphocytes from young and aged mice immunized with pS or co-immunized with pADA will be tested for immune correlates of pADA-mediated adjuvanticity in aged models. We further determine if co-immunization with pADA would alter the recruitment of innate immune subsets at the site of infection in old and young mice following vaccination with COVID-19 vaccine. We further use 10× genomics to quantify levels of somatic hypermutation (SHM) in the B cell receptors (BCRs) of pADA co-immunized young and aged mice as an indirect measure of the role ADA-1 has in T:B cells help.

3) Demonstrate that pADA co-immunization mediates a durable and broad protection from SARS-COV-2 challenge in aged mice by targeting and reversing defective APC, GC-$T_{FH}$ and GC-B cells in aging. AAV transduction of wild type mice has recently been demonstrated to be an easily accessible model for SARS-CoV-2 respiratory infection in mice. We will use this model to demonstrate that pADA co-immunization enhances protection from SARS-COV-2 lung infection in aged mice.

Significance

There is a great need for vaccine adjuvants that are effective in enhancing vaccine durability and boosting immunity in at risk populations, including elderly. In December 2019, a cluster of respiratory illness in the city of Wuhan, China defined the onset of a worldwide pandemic involving a novel coronavirus (SARS-CoV-2). Patients with SARS-CoV-2 infection may be asymptomatic, but often present with fever, malaise, myalgias, and cough. Initial epidemiologic estimates from the WHO suggest that approximately 15% of patients will develop severe disease and evidence of viral pneumonia, manifest by hypoxemia and multi-lobar ground glass opacities on chest CT scan, and that many of these patients with severe disease will require ICU care, and progress to develop ARDS, shock and secondary organ failures, and super-infections. Based on reports from China and preliminary estimates form the US, increased mortality from COVID-19 has been associated with older age and underlying co-morbidities such as COPD, ischemic heart disease, diabetes mellitus, and immunosuppression [1,2], but morbidity and mortality may also occur in younger patients. Importantly, transmission rates are high and the spread is difficult to track. Taken together with the fact that SARS-CoV-2 causes pandemic disease within a period of weeks, control of this viral infection will be challenging without a vaccine formulation to stop the spread and prevent deaths.

SARS-CoV-2 infection and increased risk in the elderly. By 2050, the size of the global elderly population, or those over 60, will exceed the entirety of younger individuals. Aging has been associated with the progressive decline in immune function, known as immunosenescence, that leads to decreased protection following vaccination and more severe consequences of infection. Indeed, the case fatality rate for those over 60 in the SARS-CoV-2 pandemic is 14.1% while for those that are younger, that number is significantly less. Current vaccine strategies do not always sufficiently protect older individuals. With this immune remodeling comes alterations in key pathways that leads to ‘inflammaging’ or the chronic activation of inflammation. Important mediators between innate and adaptive immunity, like dendritic cells, monocytes, and macrophages, have decreased pro-inflammatory cell signaling after stimulation or vaccination (Type I interferons, IL-6, TNF-alpha) that may lead to a decrease in immune function like phagocytosis and antigen presentation. Additionally, aging affects the T and B cell compartment with not only decreased total cell number but also function. Follicular Helper T cells ($T_{FH}$) have been shown to be impaired during aging. For example, recent studies have shown that $T_{FH}$ cells are impaired functionally and numerically in aging subjects following vaccination with flu vaccine. This could account for the low immune response to vaccination in elderly people [3]. Aging mice recruitment of T cells and $T_{FH}$ cells to B follicles is also shown as impaired following West Nile vaccine administration which could affect immune response in aging mice [4]. Thus, it seems that response to vaccine in the context of aging is influenced by the functional and numerical status of $T_{FH}$ cells. By boosting $T_{FH}$ function and frequency using a new molecular adjuvant that enhances $T_{FH}$ function and vaccine response, the compositions provided herein improve vaccine response, thereby, addressing SARS-CoV-2 infection in the elderly population.

$T_{FH}$ cells represent a unique subset of $CD4^+$ T cells with the ability to elicit the development of Abs with multiple effector functions. These cells interact with Germinal centers (GC) B cells and instruct the generation of long-lived memory B cells and plasma cells. These cells are also responsible for isotype switching which gives Ab their ability to interact with large number of innate immune cells for Ab effector killing functions. Thus, a successful COVID-19 vaccine that is capable of eliciting strong $T_{FH}$ functions likely improves protection against COVID-19 infection in the elderly. Hence, the magnitude and the quality of anti-COVID-19 Ab responses could be augmented by improving $T_{FH}$ function probably by altering $T_{FH}$ functional programs leading to altered and prolonged interactions between $T_{FH}$ cells and GC B cells.

ADA-1 exerts its functions through both enzymatic and non-enzymatic mechanisms [5]. The enzymatic function of ADA-1 is achieved by irreversible catabolism of adenosine or 2'-deoxyadenosine into inosine or 2'-deoxyinosine via deamination[5]. In humans, functional mutations of ADA-1 leads to early-onset severe combined immunodeficiency (SCID), which is characterized by the loss of functional T, B and NK lymphocytes, and an extreme susceptibility to infections which are often caused by "opportunistic" organisms [6.7]. The severe immunodeficiency could be either due to elevated toxic levels of 2'-deoxyadenosine [8] or due to immunosuppressive effect of adenosine [9,10]. ADA-1 possesses a novel function in regulating immunity by 1) altering the cytokine program of already differentiated GC $T_{FH}$ cells through enhancing cytokines production that are important for B cell function in vitro, 2) enhancing Ag-specific $T_{FH}$ cell differentiation in vivo, and 3) enhancing B cell help of pre-GC $T_{FH}$ and non-$T_{FH}$ cells. More importantly we showed that ADA-1 acts as bonafede adjuvant because when ADA-1 was given as adjuvant with an HIV vaccine in mice, we observed a qualitatively superior Ab response (See Example 1). More importantly, it has been recently shown that ADA-1 activity wanes with age and this could affect innate and adaptive immunity in the elderly [12,13]. Thus, using ADA-1 as adjuvant in vaccine for the elderly will boost immune response and provide protection from COVID-19 infection.

It is important to note that ADA-1 has been successfully administered into humans in molecular and recombinant forms in the treatment of human SCID with minimal side effects [14-16]. Furthermore, we did not observe any adverse events when ADA-1 was used in our mouse studies (See Example 1) and PEGylated bovine ADA-1 is an approved therapeutic for human patients. Thus we expect our molecular ADA-1 to have minimal side effects and be tolerated when used as adjuvant.

Adjuvants targeting $T_{FH}$ cells. Using Precision Vaccines to develop novel platforms is the most tractable way to alter how immune system responds to vaccine. One of the most intriguing targets in vaccine development is $T_{FH}$ cells since these cells are critical in shaping and instructing humoral immune response. Another important reason to target $T_{FH}$ cells is their role in development of neutralizing Abs with broad breadth. There have been some innovative approaches to harness the function of $T_{FH}$ cells in vaccine development. For example, it has been shown that glucopyranosyl lipid adjuvant-stable emulsion (GLA-SE) when used in human studies elicited $T_{FH}$ expansion in experimental malaria vaccine when compared to Alum [17]. Additionally, it has been shown that using water-in-oil-only adjuvants selectively promoted $T_{FH}$ cells polarization [18]. M59 high-affinity universal CD4+ T-cell epitope (PADRE) has been shown to promote $T_{FH}$ cell expansion when used as adjuvant [19,20]. While all of these adjuvants have increased quantitatively Ab response, ADA-1 is unique in its ability to elicit neutralizing Abs in vivo. This example examines ADA-1 induction of qualitative and persistence alterations in anti-COVID-19 Ab responses in the elderly and protect them against this infection.

Impact of a SARS-CoV-2 vaccine and novel adjuvants to improve efficacy in those at high risk of morbidity and mortality associated with this infection. Vaccines are the most effective strategy for preventing infectious disease since they are more cost-effective than treatment and reduce morbidity and mortality without long-lasting effects. Over the past two decades, three human coronaviruses (SARS-CoV, MERS-CoV, and SARS-CoV-2) emerged worldwide, causing considerable threat to global health [21]. The spike (S) protein of coronaviruses is an important target for vaccine development because it mediates the infection mechanism through receptor binding of host cells [22,23]. The S protein of human infectious coronaviruses SARS-CoV-2 and SARS-CoV use ACE2 as a receptor. The S1 subunit of S protein contains a receptor-binding domain (RBD) and the S2 subunit is necessary for membrane fusion between host cells and viruses [24,25]. As the coronavirus S glycoprotein is surface-exposed and mediates entry into host cells, it is the main target of neutralizing antibodies upon infection and will be the antigenic focus of the DNA vaccine proposed in this project.

Understanding immune correlates of SARS-CoV-2 infection and recovery in order to design better prophylactic vaccine and adjuvant formulations. Patients who became infected and survived infection can reveal clues about the needed host immune responses that lead to recovery and protection from SARS-CoV-2. In March 2020, Theverajan et al., examined the kinetics of immune responses in relation to clinical and virologic features of a patient with mild-to-moderate COVID-19 that required hospitalization [26]. Evidence was found that recruitment of immune cell populations (antibody secreting cells (ASCs), T follicular Helper cells ($T_{FH}$) and activated CD4+ and CD8+ T cells), together with IgM and IgG SARS-CoV-2-binding antibodies, in the patient's blood occurred before the resolution of symptoms. Understanding the kinetics and phenotype of host immune response as it relates to clinical phenotype underscores the requirement of such adaptive immune responses required by a protective vaccine in order to limit or mitigate disease progression. Development of vaccine adjuvants that target the $T_{FH}$ and antibody pathways are key to successful vaccine strategy for COVID-19.

INNOVATION. This is the first time ADA-1 has been used as adjuvant using animal models. There are several innovative aspects of this use. I) ADA-1 has a unique function in improving $T_{FH}$ function. This makes ADA-1 a unique adjuvant and thus will be used as a novel approach to improve the quality and persistence of anti-COVID-19 Ab responses. Importantly, ADA-1 also elicited significant improvement in vaccine-specific CD8+ T cell responses, probably through enhancing CD4 help (FIG. 16,17B); thus, activating both arms of the immune response. Additionally, ADA-1 was able to instruct long-lived memory T cell and memory B cell responses as shown in FIG. 16, 17 which makes ADA-1 a unique adjuvant that can both elicit qualitatively stronger and durable immune response.

II) The DNA vaccine platform represents an innovative approach by direct injection of plasmids encoding the antigens and allows for co-delivery of molecular adjuvants that could include immunomodulatory molecules to direct the immune response to T or B cell adaptive immunity [33,34] or to mucosal sites [33,35]. Using this proven vaccine platform and delivery system, an innovative SARS-CoV-2 S1 vaccine and adjuvant formulation will be tested in this proposal using the young adult and aged mouse preclinical screening model.

Approach

Global strategy: Our results revealed that ADA-1 as adjuvant enhanced the functional quality of anti-COVID-19 Abs in mice and improved the persistence of COVID-19 specific memory B cells and memory T cells.

Figure 15A:
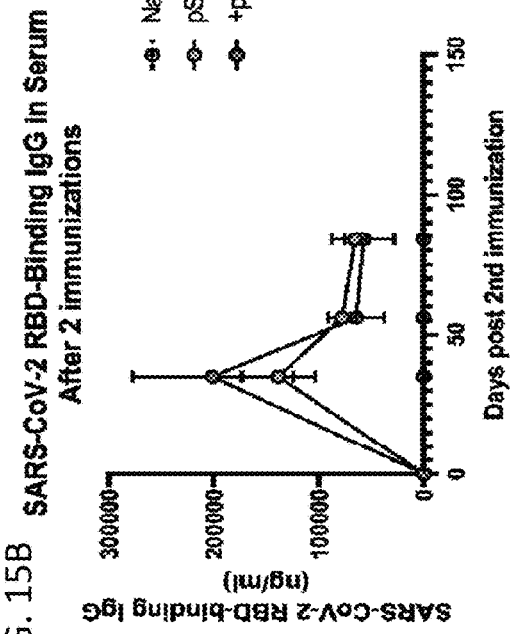
FIG. 15A-15D. pADA-induced antibody enhancement remains durable after a single immunization. Mice were immunized either once or twice with pS alone or co-immunized with pS and pADA (+pADA) and serum antibody responses were measured over time following 1 (FIG. 15A) or two (FIG. 15B) immunizations.
Figure 15C:
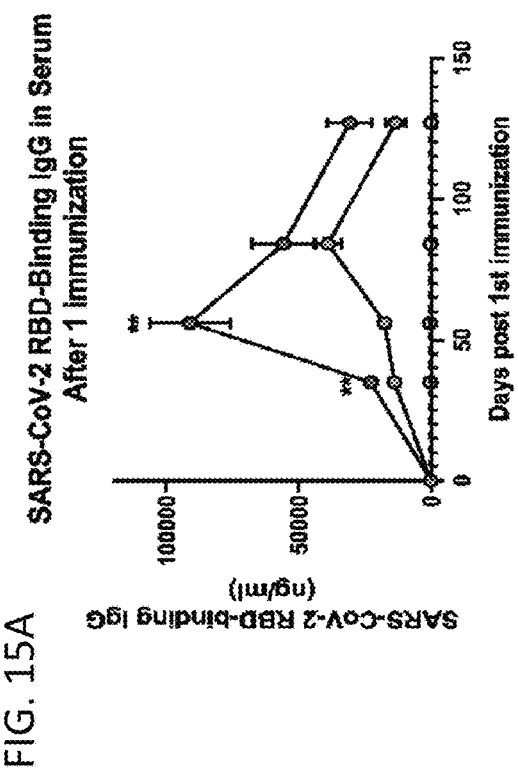
Figure 15B:
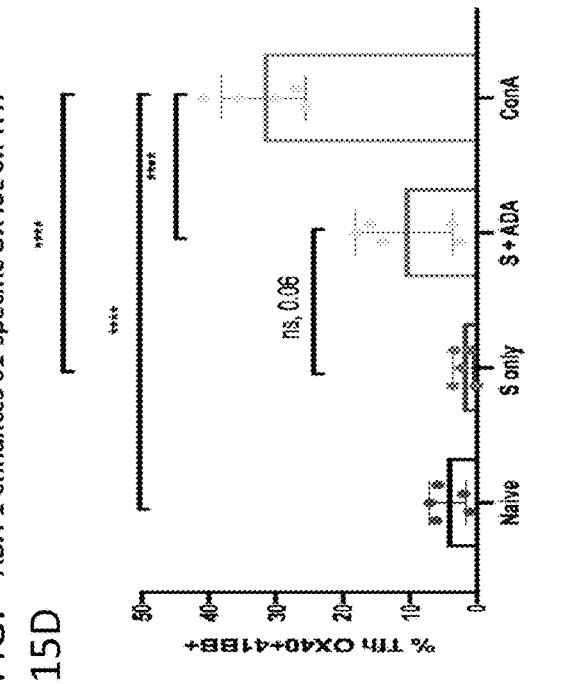
Figure 15D:
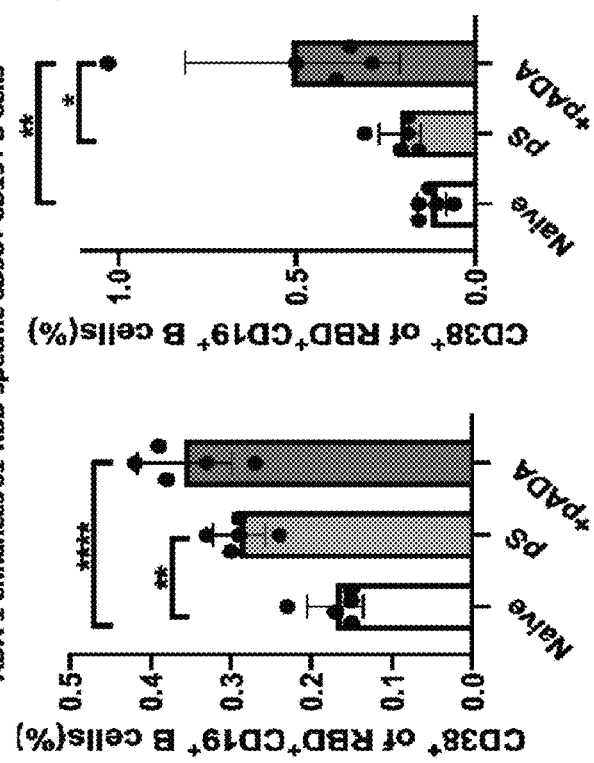

We have demonstrated the ability of ADA-1 to improve the quality of anti-COVID-19 responses in mouse models. Thus, the inclusion of the immune adjuvant, ADA-1 with DNA plasmids encoding SARS-CoV-2 spike, will elicit anti-viral S1 antibodies and activate S1-specific CD4/CD8 T cells and Ag-specific memory B cells, further enhancing a durable and functional host immunity to this infection in at risk populations, using the aging mouse model.

Experimental Rigor. (a) Power calculations for animal use. Experiments in this application use mice to measure immune-mediated efficacy of vaccines. To determine animal group sizes, power calculations were performed (see Vertebrate Animal Section for details) in consultation with internal biostatisticians. We use both female and male animals to rule out any gender specific effects. Mice are the preferred animal model due to their inbred nature, thus providing a clonal immune response across experimental groups. Studies are powered to detect statistical differences in treatment groups, and prism Graphpad statistical analysis methods will be used. Experience with the use of various analyses for determining the probability of differences between control and experimental mouse groups indicates the need for at least 10 mice per group, and this usually gives robust results with Power (b) >80% and significance (a) <0.05. (b) Reducing bias. Mice are randomized into experimental groups to which researchers performing the analysis will be blinded. (c) Improving precision and reducing variability.

Orthogonal functional ex vivo, in vitro and in vivo methods are used to test and validate hypotheses whenever possible. All experiments will include multiple biological and technical replicates, and results will be analyzed by parametric or non-parametric analyses as appropriate and corrections for multiple comparisons used when necessary C4: Timeline of Immunization, Specimen Collection and challenge: We will isolate immune cells post immunization from splenocytes and lymph nodes at day 14, 38 and 60 post immunizations.

Blood and mucosal BAL washes will be collected post-each vaccination, and at day 60 prior to COVID challenge. Single cell suspensions of leukocytes will be isolated from splenocytes and lymph nodes by manual disassociation through a cell strainer. Isolated cells will be used fresh and cryopreserved for future studies.

Vaccine: The antigen used herein was developed by cloning the SARS-CoV-2 Wuhan-Hu-1 spike glycoprotein gene (BEI resources NR-52310) into the pVAX backbone (Invitrogen). Site directed point mutation at amino acid 614 in the spike protein (D614G dominant circulating strain in the United States) was created, the antigen was modified the antigen to express an IgE secretory leader sequence for improved expression, codon optimized for mammalian expression, and manufacture of research grade DNA vaccine for immunizations. Preclinical research grade ADA-1 molecular adjuvant is already in hand in the Kutzler laboratory as previously described in Example 1. Vaccine delivery and experimental groups: we will first dose the pS1 antigen to determine minimal dose (test a range of 2.5, 5, or 10 μg per mouse per immunization, with 10 mice per group in young vs 12 mice per group in old mice to account for potential 20% death due to old age), use pVAX placebo control for baseline) that results in at least 25,000 ng/ml of anti-S1 antibody as measured by ELISA. Once the optimal antigen dose is found, we will next dose the pADA-1 adjuvant to determine the optimal dose (5, 10, 25 μg per mouse per immunization with 10 mice per group, in young vs old mice), that leads to statistical difference (p=<0.05) between pADA-1 and pS1 antigen only as measured by anti-S1 antibody and S1-specific T cell IFN-gamma ELISpot at effector time points. We utilize the optimal doses that lead to detectable anti-S1 humoral and cellular immunity and repeat the immunizations of pS1+/−pADA-1 and carryout the more detailed analysis of antigen-specific antibody (quantity and quality) in the periphery and respiratory mucosa, and use cellular flow cytometric assays to examine lymph node GC $T_{FH}$, and T cell responses at both effector and memory timepoints. In the SARS-CoV2 mouse challenge study, we look at the durability of the immune response at up to day 60 post immunization in aged and young mice and efficacy. The vaccine placebo (pVAX), S1 antigen at doses of 2.5, 5, or 10 μg and 5, 10 or 25 μg of pADA-1 is administered to the tibialis anterior (TA) muscle by needle injection followed by CELLECTRA® in vivo electroporation (EP). The CELLECTRA® EP delivery consists of two sets of pulses with 0.2 Amp constant current. Second pulse sets are delayed 3 s. Within each set there are two 52 ms pulses with a 198 ms delay between the pulses.

Data. pADA co-immunization induces robust humoral immunity after a single SARS-COV-2 DNA vaccination. Female 6-8-week-old BALB/c mice were immunized twice separated by four weeks with 10 μg of plasmid-encoded spike (pS) or co-immunized with pS and 10 μg of pADA (+pADA) (FIG. 14A). Serum antibody responses were measured after one and two immunization. We observed significant increases in SARS-COV-2 spike RBD IgG in the serum of pADA co-immunized mice, as compared to mice receiving pS alone after a single immunization (FIG. 14B-14D). After two immunizations mice immunized with pS alone had IgG levels equivalent to those receiving a single co-immunization pADA (FIG. 14E). We observed a significant increase in SARS-COV-2 pseudoviral neutralization titers after 1 co-immunization with pADA (FIG. 14F) which was not present for pS only immunized animals. As with serum IgG, after two immunizations both pS only and pADA co-immunized mouse sera was equally capable of neutralizing SARS-COV-2 pseudoviruses in vitro (FIG. 14G). This data indicates that pADA co-immunization is dose sparing, inducing equivalent levels of antigen-specific IgG after a single immunization as two immunizations with pS alone.

pADA co-immunization enhances SARS-CoV-2 spike DNA humoral memory. Recent studies suggest that anti-SARS-CoV-2 immunity may wane quickly[36], therefore we determined if pADA would improve durability of memory B cell and T cell responses. For this experiment, we immunized mice once or twice and rested them for 60 days (memory response) prior to sacrifice and performed receptor-binding domain (RBD)-specific antibody ELISAs to quantify antigen-specific antibodies in serum longitudinally. We also used fluorophore-conjugated probes to quantify antigen-specific memory B cells ($CD38^+$ $CD19^+$ B cells) at both effector (day 14) and memory (day 60) timepoints post-1 immunization. We observed statistically significant increases in RBD-binding IgG in the serum of pADA co-immunized animals as far out as 56 days post-1 immunization (FIG. 15A). In keeping with our previous finding that pS immunization requires a boost in order to generate antibody responses as robust as those generated by pADA co-immunization at a single dose, we observed no significant differences in RBD-binding IgG between the sera of pS boosted mice and their pADA co-immunized counterparts after two immunizations (FIG. 15B). In the lymph nodes we observed similar frequencies of CD38+ RBD+ B cells at day 14 post-1$^{st}$ immunization; however, pADA co-immunized animals had a significant increase in these cells 60 days after a single immunization (FIG. 15C). In addition, as shown in FIG. 15D, Ex vivo stimulation of lymph node cells with S1 peptides results in an increase in the expression of OX40L, which define antigen-specific $T_{FH}$ cells, from ADA-1 co-immunized mice. These data indicate that while pADA co-immunization enhances early humoral immune responses, it also promotes the establishment of a long-lived memory B cell and antigen-specific $T_{FH}$ subsets that remain detectable two months after immunization and supports durable humoral immunity in the periphery for at least three months after a single immunization.

Figure 17A:
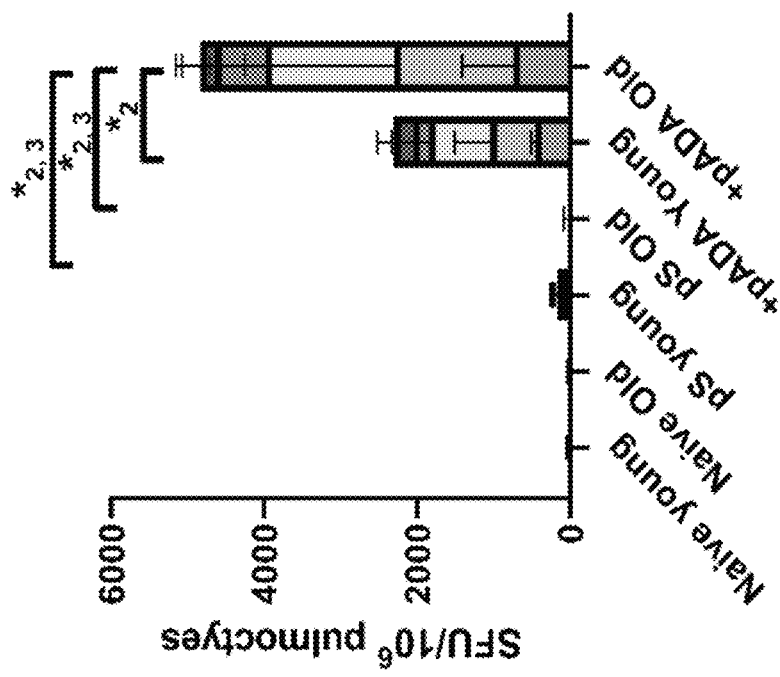
FIG. 17A-17B. pADA co-immunization enhances anti-S1 in sera and T cell responses in the lung of immunized aged mice. Mice were immunized twice separated by four weeks with pS alone or co-immunized with pS and pADA (+pADA), sacrificed at day 12 post-$2^{nd}$ immunization and RBD-specific serum IgG was measured in and serum (left) and SARS-CoV-2 specific IFN-gamma secretion was measured by ELISPOT in the (right panel). Symbols represent the average of replicates for an individual animal. Bars represent the mean and SEM. * p<0.05, **p<0.01 by student's t-test or two-way ANOVA. Data are representative of 1 experiment with n=3-5/group.
Figure 17B:
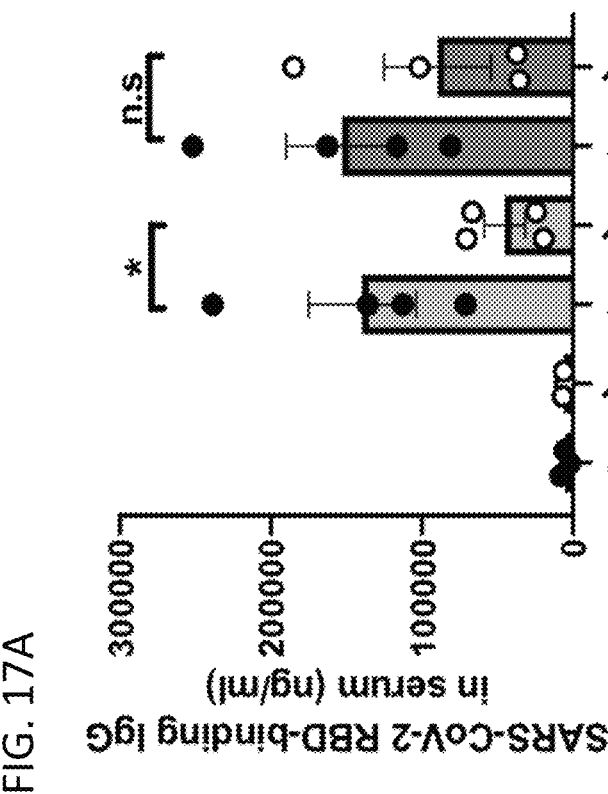
Figure 18:
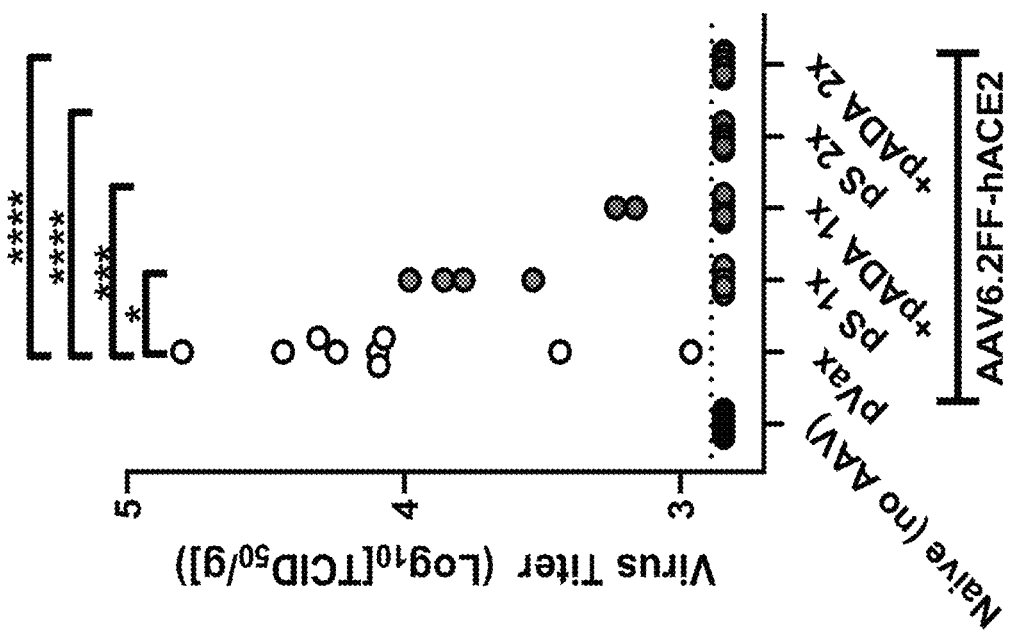
FIG. 18. pADA co-immunization enhances SARS-COV-2 protection in vivo. Mice were immunized once (1×) or twice (2×) separated by two weeks with pS alone, pS and pADA (+pADA), or empty plasmid vector (pVAX) and transduced with human ACE2 via AAV infection (AAV6.2FF-hACE2) or left naïve (no AAV) prior to intranasal infection with SARS-CoV-2 strain VIDO-01. Animals were sacrificed four days post challenge and virus was quantified in lungs via plaque assay. Each symbol represents an individual animal. *p<0.05, ****p<0.0001 compared to pVax via Kruskall-Wallis multiple comparison test (ANOVA).

T cell mediated immunity has been shown to play a critical role in protection against COVID-19 infection, we thus determined if pADA-1 will also enhance both effector and memory cell mediated T cell response. We isolated splenocytes from animals at both the effector and memory timepoints following 1$^{st}$ immunization and quantified cell-mediated immunity using intracellular flow cytometry. The frequency of IL-2+CD8+ and TNFα+CD8+ T cells in response to SARS-COV-2 spike peptide stimulation was similar at day 14 post-1 immunization between animals receiving pS alone and those co-immunized with pS and pADA (FIG. 16A-16D). However, at day 60-post immunization animals which were co-immunized with pS lost their ability to secrete either IL-2 or TNF-α. However, memory CD8+ T cell response was significantly maintained in the presence of pADA (FIG. 16A, 16B). Interestingly unlike CD8 T cells, we observed significantly more TNF+CD4+ T cell in the presence of pADA even after the first immunization (FIG. 16D). Similar to memory CD8+ T cell response, pADA also improves memory CD4+ T cells after 60 days of immunization. These data strongly indicate that pADA can enhance antigen specific immunity at both effector and memory timepoints. This is critical in developing novel COVID-19 vaccines.

pADA co-immunization enhances immune responses to SARS-CoV-2 DNA immunogens in aged mice. We performed similar immunogenicity experiments with 6-8-week-old (young mice) and 72-week old (aged mice) C57BL/6 mice and compared anti-spike responses in the respiratory mucosa and periphery of aged mice and their young counterparts after two immunization. As expected, aged mice immunized with pS alone had statistically significantly decreased antigen-specific humoral responses compared to pS-immunized young mice. However, among pADA co-immunized mice, we observed no differences in RBD-specific IgG between young and aged mice (FIG. 17A). We also quantified IFNγ secretion in response to SARS-CoV-2 spike peptide stimulation by ELISpot in the lungs of aged mice compared to their young counterparts. Old animals immunized without pADA showed almost no ability to secrete IFN-g. Young animals immunized in the absence of pADA showed marginal generation of IFN-g+CD8+ T cells. Interestingly, pADA significantly increased frequency of IFN-g+CD8+ T in aged and young animals (FIG. 4B). These results indicate that ADA-1 immunization restores critically impaired humoral immunity and can enhance cell-mediated immunity in the respiratory mucosa.

pADA co-immunization enhances SARS-COV-2 protection in an AAV-transduced wild-type mouse model of SARS-COV-2 infection. In order to evaluate the efficacy of our spike DNA constructs, we determined if pADA can protect mice against COVID-19 challenge. 6-8 week old male and female BALB/c mice were immunized once or twice separated by four weeks with pS alone, co-immunized with pS and pADA (+pADA), or immunized with empty plasmid vector (pVax) and rested for 80 days prior to infection with SARS-CoV-2 (VIDO-01 P2) after intranasal transduction an AAV vector expressing human ACE2 (AAV6.2FF-hACE2). Infectious viral particles were measured in lung homogenate four days following infection. We observed a significant decrease in replication competent viruses in the lungs of mice receiving pS alone, with 60% of mice displaying no virus after a single dose of pS. However, 80% of mice receiving pADA displayed no detectable virus in their lungs (FIG. 18). Interestingly, the 2 mice that had residual virus in the presence of pADA showed 1 long reduction compared to those without pADA. After two immunizations, 100% of mice receiving either both pS alone and pS with pADA co-immunization had no detectable replication-competent virus in their lungs (FIG. 18). These data further indicate that a single dose of pADA adjuvanted DNA constructs can have dose sparing effects for pS DNA immunogens and indicate that pADA-mediated enhancement of vaccine-induced responses can enhance protection in vivo. Thus, we expect that pADA co-immunization will improve immunity and protect aged mice against SARS-CoV-2 challenge.

Our data demonstrates that pADA immune adjuvant improves the quality and persistence of humoral and T cell-mediated immunity to S1 vaccine in aged mice. Rationale: Aged patients have significantly increased COVID-19 morbidity and mortality. Numerous vaccine candidates are currently in clinical and preclinical trials however none have been tested for immunogenicity in the elderly. More importantly, current COVID-19 vaccines have shown undesirable side effects after 2 immunizations and also at high doses of antigen like the Moderna vaccine. Therefore, a vaccine with only one immunization and reduced dose of antigen represent an extremely desirable vaccine candidate for COVID-19 infection. These will become critical when designing vaccine to target the elderly population. We previously shown that co-immunization with plasmid-encoded ADA-1 (pADA) in the context of an HIV-1 envelope DNA immunogens resulted in robust enhancement of humoral and cell mediated immunity (See Example 1). ADA-1 is critical for lymphocyte function and has been reported to be decreased in aged human cells[37]. Accordingly, co-immunization with pADA enhances anti-spike immunity in young and aged mice.

Mice immunized with pADA display high levels of anti-COVID-19 Ab response both in young and aged mice. Immunization with pADA generates a memory B cell and memory T cell response that is durable for at least 60 days. Considering recent data about waning antibody response in people infected with SARS-CoV-2 after 4 months, a vaccine that is able to elicit a persistent memory response will be valuable in the fight against COVID-19. Co-immunization with pADA also improves the effector and memory T cell response in both young and aged mice and cell-mediated immunity is likely critical to protection in the context of SARS-CoV-2 infection. Further, pADA alters the cytokine profile of $T_{FH}$ cells leading to an improvement in B cell help including IL-21 and IL-4 production from these cells which is critical to the generation of antigen-specific plasma cells and long-lived memory B cells. [38-41].

We will determine how ADA influence both arms of the immune system by investigating the effect of ADA on the activities of DCs, higher titers of anti-S1 immunoglobulin, increased breadth and somatic hypermutation of B cell receptor specificity. Rationale: Previous reports suggest that ADA-1 enzymatic activity is decreased as human cells age[37]. ADA-1 activity is critical to lymphocyte function and mutations in ADA-1 cause severe-combined immunodeficiency in humans [43]. Our data indicate that pADA co-immunization is effective in aged mice, such that pADA co-immunized mice and their co-immunized young counterparts have similar humoral responses against SARS-COV-2 RBD while aged mice immunized with pS alone have significantly decreased humoral responses compared to pS-immunized young mice. This indicates that the ADA-1 pathway is critical to vaccine efficacy in aged mice. With this in mind, we will (1) characterize ADA-1 and ADA-1 receptor expression and distribution on lymphocytes isolated from human PBMCs from patients of various ages [44,45]; (2) ADA-1 and ADA-1 receptor expression distribution on mouse lymph node lymphocytes from young and aged mice; (3) Identify the innate immune subsets and cytokines recruited locally, and 4) Quantify levels of somatic hypermutation (SHM) of B cell receptors (BCRs) in aged and young mice immunized with placebo, pS alone or co-immunized with pADA by sorting antigen-specific B cells, by 10× genomics. By the completion of this aim, we will be able to identify age-associated deficiencies in the ADA pathway and how ADA rescues the response in aging mice.

We will determine if co-immunization with pADA would alter the recruitment of innate immune subsets at the site of infection in old and young mice following vaccination. Our data indicates that pADA will recruit and improve differentiation of antigen presenting cells similar to what we have observed in human in vitro assays [11]. Skin tissues at the site of immunization with vaccine in the presence and absence of pADA will be excised for the 1) Immunohistochemistry and 2) qPCR analysis. Biopsies will be taken using standard skin biopsy protocol. Each biopsy sample will be divided into two using a sterile scalpel. One half of each sample will be fixed, embedded in paraffin and stained for histology with Hematoxylin and Eosin and for determination of specific immune cell populations using specific immunohistochemical staining. The other half of each sample will be flash frozen at −80° C. for subsequent qPCR to identify upregulation of specific cytokines and chemokines. Specifically, we will examine the recruitment of antigen-presenting cells including the Langerhans cells (LCs), the CD14+ dendritic cells. The dermis contains dermal dendritic cells, endothelial cells and mast cells. Our data indicates that these cells play critical role in the priming of the immune response. We will also use CD207 to monitor Langerhans cells. Single CD14+, CD11c+, and CD207, CD141, CD1c/CD1a, or CD14+ cells as well as CD207+ cells staining procedures will be performed.

We will also demonstrate whether pADA immunization will alter local cytokines and chemokines profiles at the site of infection. pADA is able to induce the production of distinct cytokines and chemokines at the sites of exposure that are capable to recruit innate immune cells and prime adaptive immune response. This has been observed in our human studies See Example 1. Biopsy sample taken from site of will be flash frozen at −80° C. for subsequent qPCR to identify upregulation of specific cytokines and chemokines such as IL-1α, IL-1β, TNFα, CCL2, CCL6, CCL11, CCL17, CCL19, CCL20, and CCR7. This will be achieved by measuring the transcriptional profiles of frozen tissues using quantitative BioMark technology. We will monitor a set of genes (100 genes) that represent different cytokine and chemokine programs (Th1, Th2, Th17, $T_{FH}$, Treg as well as a variety of chemotaxis factors). We will also measure the expression of specific immune subsets including HLA-DR, CD80, CD86, CD14, CCR7, CD1a, CD11c, CD207, CD205, CD123, DC-SIGN. CD141. We have optimized primers for the list of 100 genes in multiplex assays and for as little as 500 cells. RNA will be extracted using standard protocols established in our laboratory. BioMark assay will be performed.

We will determine if pADA immunization increased the breadth of the B cell receptor (BCR) by quantifying the amount of somatic hypermutation (SHM) present in BCRs of animals immunized with pS alone compared to those co-immunized with pS and pADA. Antigen-specific B cells can be identified by our gating strategy and thus sorted for single cell sequencing via 10× genomics. We have successfully sorted and monitored COVID-19 B cells using fluorogenic probes targeting RBD (FIG. 15C). In order to investigate the breadth of the B-cell repertoire by ADA stimulation we will employ high-throughput sequencing directed at the antigen receptors. Briefly, mRNA is extracted from the samples, primers designed to be homologous to the constant regions of the antigen receptor are used to selectively amplify mRNA containing the sequence of the expressed receptor. During amplification adapters and unique-molecular indices are added to facilitate sequencing and down-stream analysis. This technique is broadly called, Rep-Seq (Repertoire-Seq) and is reviewed in greater detail elsewhere [46]. After sequencing there are numerous computational steps which transform the raw sequence reads into a wealth of information including specific B-cell recognition sequences and their prevalence, their germline origin, and the phylogenetic relationship of the hypermutation that lead to the specific receptor sequence [47]. Samples collected from previous experiments will be provided to a place to the Wistar Genomics Core for their standard Rep-Seq sequencing steps which will deliver the raw sequencing data and a basic quality control analysis. This end-to-end analysis will directly provide the sequence of the B-cell epitopes that are being presented in each sample. These epitopes will be scanned against the vast database of over 10,000 nCov2 sequences in the field of nCov2 variability. These nCov2 matching epitopes will be quantified across all of the sequenced samples. Measures like the diversity, richness, and Shannon entropy will be calculated in order to capture the breadth of the B-cell repertoire and the change across the stimulation conditions. Testing for increased hypermutation will be done by examining number of edits between the observed clonotypes and the closest source genotypes. An ANOVA will be used to test for significant differences across the groups. We hypothesize that due to the increased somatic mutation induced by ADA there will be an increase in the richness of the clonal population in the ADA treated groups as well as an increase in the number of edits used to generate the observed epitopes.

Expected Results: Results obtained from experiments described in herein will determine that PBMCs from older adults have decreased ADA-1 receptor expression (CD26, $A_1R$, and $A_{2b}R$) and distribution combined with lower enzymatic activity in comparison with young PBMCs. The aged mice vaccinated with pS and pADA have upregulated CD26, $A_1R$, and $A_{2b}R$) leading to a larger secretion of anti-S1 IgG and a more protective response.

The number of positive cells per mm are counted manually using computer-assisted image analysis and the number of recruited dendritic cells following immunization with and without pADA are compared. For assessment of statistical significance, we apply a paired sample t-test. the immunization with pADA induces significant recruitment of dendritic cells to the site of exposure when compared to no pADA. Increased infiltration of CD14+ and CD11c+ infection sites occurs since our results in humans have revealed improved maturation of dendritic cells and elevated secretion of multiple cytokines with the ability to attract multiple innate immune subsets [49]. BioMark analysis is be performed by calculating the Delta Ct for each gene in the exposed and unexposed frozen tissues relevant to housekeeping genes. For assessment of statistical significance, we apply a paired sample t-test. The presence of pADA induces distinct and elevated increase in cytokines and chemokines. Upregulation of chemokines that are responsible for recruitment of dendritic cells occurs. The upregulation of costimulatory receptors such as CD80, CD86, CD40, ICOS and cytokines like IL-2 and IL-6 that are important factor for priming of T cells also occurs.

We will demonstrate that pADA co-immunization enhances protection from SARS-COV-2 challenge in young and aged mice. Rationale: COVID-19 exhibits increased morbidity and mortality in aged patient populations. While vaccines which limit the spread of disease will be critical to stopping community spread, vaccine responses in aged patients are sub-optimal. Unfortunately, the ability of any of the current SARS-CoV-2 vaccine candidates to induce protective responses in ageing molecules remains unknown. ADA-1 enzymatic activity has been reported to decrease as cells age and co-immunization of mice with plasmid encoded ADA-1 (pADA) in the context of DNA antigens significantly increases humoral and cell-mediated immunity. Accordingly, pADA-co-immunization with spike plasmid DNA antigens (pS) will protect aged mice from SARS-CoV-2 infection.

Mouse Challenge Model. Post-vaccination, immunized C57bl6 mice will be transduced with $1\times10^{11}$ AAV6-hACE-2 viral genomes in 50 μl of sterile PBS [50]. Sixteen days post transduction, mice will receive an intranasal instillation of SARS-CoV-2 isolate VIDO-01 (passage 2) (1×105 PFU) in a total volume of 50 μl. Health checks are performed daily on the mice. This study will be conducted at the Biosafety Level 3 (BSL3) facility at the public health agency of Canada (PHAC). For infectious virus assays, thawed tissue samples are weighed and placed in 1 ml of MEM supplemented with 1% heat-inactivated FBS, 1× L-glutamine then homogenized in a Bead Ruptor Elite Bead Mill Homogenizer (Omni International) at 4 m/s for 30 seconds then clarified by centrifugation at 1500×g for 6 minutes. Tissue homogenates are serially diluted 10-fold in MEM supplemented with 1% heat-inactivated FBS, 1× L-glutamine, and 2× penicillin-streptomycin. One hundred microliter volumes of sample dilutions are then added to 96-well plates of 95% confluent Vero cells containing 50 ml of the same medium in replicates of three and incubated for 5 days at 37° C. with 5% CO2. Plates are scored for the presence of cytopathic effect on day 5 after infection.

We began experiments with full-length spike plasmid DNA based on the original sequence published early in the Wuhan outbreak. We have since transitioned to using DNA antigens encoding the D614G spike variant and observed similar immunogenicity in young mice. Furthermore, sera from mice immunized with original Wuhan spike DNA antigens is capable of neutralizing D614G spike pseudovirus in vitro. Thus, we anticipate no differences in overall DNA vaccine immunogenicity in these experiments. Our data indicate that pADA enhances anti-SARS-CoV-2 DNA vaccine immunogenicity in aged mouse models such that no statistically significant differences were observed between pADA co-immunized aged mice and their young counterparts (FIG. 14). These results indicate that protection in aged mice will be similar to protection levels observed in young mice.

Statistical analysis: All statistical analysis was performed using GraphPad Prism software version 6. Flow cytometry data were analyzed using Flowjo version 8 (Treestar). Data are presented as the mean±standard error of the mean or standard deviation, where denoted. Outlier analysis was performed in PRISM using the ROUT method with Q=1% and identified outliers were removed prior to statistical analysis for differences between groups. We performed Shapiro-Wilk's normality tests on all data sets and where appropriate, the statistical difference between immunization groups was assessed using an ordinary one-way analysis of variance (ANOVA) (Tukey's multiple comparison test) or Student's t-test for normal data and Kruskall-Wallis multiple comparison test, or Mann-Whitney test for non-normal data. *p<0.05, P<0.01, *P<0.001, ****p<0.0001.

All patents, patent publications, and other publications listed in this specification, as well as the sequence listing are incorporated herein by reference. Specifically, the publication Gary et al, Adenosine deaminase-1 enhances germinal center formation and functional antibody responses to HIV-1 Envelope DNA and protein vaccines, Vaccine 38 (April 2020) 3821-3831, is incorporated by reference in its entirety. While the invention has been described with reference to a particularly preferred embodiment, it will be appreciated that modifications can be made without departing from the spirit of the invention. Such modifications are intended to fall within the scope of the appended claims.

REFERENCES CITED IN EXAMPLE 3

1. Zhou F, Yu T, Du R, Fan G, Liu Y, Liu Z, Xiang J, Wang Y, Song B, Gu X, et al.: Clinical course and risk factors for mortality of adult inpatients with COVID-19 in Wuhan, China: a retrospective cohort study. *Lancet* 2020, 395:1054-1062.
2. Guan W J, Ni Z Y, Hu Y, Liang W H, Ou C Q, He J X, Liu L, Shan H, Lei C L, Hui D S C, et al.: Clinical Characteristics of Coronavirus Disease 2019 in China. *N Engl J Med* 2020, 382:1708-1720.
3. Herati R S, Reuter M A, Dolfi D V, Mansfield K D, Aung H, Badwan O Z, Kurupati R K, Kannan S, Ertl H, Schmader K E, et al.: Circulating CXCR5+PD-1+ response predicts influenza vaccine antibody responses in young adults but not elderly adults. *J Immunol* 2014, 193:3528-3537.
4. Richner J M, Gmyrek G B, Govero J, Tu Y, van der Windt G J, Metcalf T U, Haddad E K, Textor J, Miller M J, Diamond M S: Age-Dependent Cell Trafficking Defects in Draining Lymph Nodes Impair Adaptive Immunity and Control of West Nile Virus Infection. *PLoS Pathog* 2015, 11:e1005027.
5. Sauer A V, Brigida I, Carriglio N, Hernandez R J, Scaramuzza S, Clavenna D, Sanvito F, Poliani P L, Gagliani N, Carlucci F, et al.: Alterations in the adenosine metabolism and CD39/CD73 adenosinergic machinery cause loss of Treg cell function and autoimmunity in ADA-deficient SCID. *Blood* 2012, 119:1428-1439.
6. Gossage D L, Norby-Slycord C J, Hershfield M S, Markert M L: A homozygous 5 base-pair deletion in exon 10 of the adenosine deaminase (ADA) gene in a child with severe combined immunodeficiency and very low levels of ADA mRNA and protein. *Hum Mol Genet* 1993, 2:1493-1494.

7. Hershfield M: Adenosine Deaminase Deficiency. In GeneReviews®. Edited by Adam M P, Ardinger H H, Pagon R A, Wallace S E, Bean L J H, Stephens K, Amemiya A; 1993.
8. Sauer A V, Brigida I, Carriglio N, Aiuti A: Autoimmune dysregulation and purine metabolism in adenosine deaminase deficiency. *Front Immunol* 2012, 3:265.
9. Apasov S G, Blackburn M R, Kellems R E, Smith P T, Sitkovsky M V: Adenosine deaminase deficiency increases thymic apoptosis and causes defective T cell receptor signaling. *J Clin Invest* 2001, 108:131-141.
10. Aiuti A, Cattaneo F, Galimberti S, Benninghoff U, Cassani B, Callegaro L, Scaramuzza S, Andolfi G, Mirolo M, Brigida I, et al.: Gene therapy for immunodeficiency due to adenosine deaminase deficiency. *N Engl J Med* 2009, 360:447-458.
11. Gary E, O'Connor M, Chakhtoura M, Tardif V, Kumova O K, Malherbe D C, Sutton W F, Haigwood N L, Kutzler M A, Haddad E K: Adenosine deaminase-1 enhances germinal center formation and functional antibody responses to HIV-1 Envelope DNA and protein vaccines. *Vaccine* 2020, 38:3821-3831.
12. Bhalla M, Simmons S R, Abamonte A, Herring S E, Roggensack S E, Bou Ghanem E N: Extracellular adenosine signaling reverses the age-driven decline in the ability of neutrophils to kill *Streptococcus pneumoniae. Aging Cell* 2020:e13218.
13. Bowers S M, Gibson K M, Cabral D A, Brown K L: Adenosine deaminase 2 activity negatively correlates with age during childhood. *Pediatr Rheumatol Online J* 2020, 18:54.
14. Candotti F, Shaw K L, Muul L, Carbonaro D, Sokolic R, Choi C, Schurman S H, Garabedian E, Kesserwan C, Jagadeesh G J, et al.: Gene therapy for adenosine deaminase-deficient severe combined immune deficiency: clinical comparison of retroviral vectors and treatment plans. *Blood* 2012, 120:3635-3646.
15. Carbonaro D A, Jin X, Petersen D, Wang X, Dorey F, Kil K S, Aldrich M, Blackburn M R, Kellems R E, Kohn D B: In vivo transduction by intravenous injection of a lentiviral vector expressing human ADA into neonatal ADA gene knockout mice: a novel form of enzyme replacement therapy for ADA deficiency. *Mol Ther* 2006, 13:1110-1120.
16. Shaw K L, Garabedian E, Mishra S, Barman P, Davila A, Carbonaro D, Shupien S, Silvin C, Geiger S, Nowicki B, et al.: Clinical efficacy of gene-modified stem cells in adenosine deaminase-deficient immunodeficiency. *J Clin Invest* 2017, 127:1689-1699.
17. Hill D L, Pierson W, Bolland D J, Mkindi C, Carr E J, Wang J, Houard S, Wingett S W, Audran R, Wallin E F, et al.: The adjuvant GLA-SE promotes human Tfh cell expansion and emergence of public TCRbeta clonotypes. *J Exp Med* 2019, 216:1857-1873.
18. Riteau N, Sher A: Chitosan: An Adjuvant with an Unanticipated STING. *Immunity* 2016, 44:522-524.
19. Mastelic Gavillet B, Eberhardt C S, Auderset F, Castellino F, Seubert A, Tregoning J S, Lambert P H, de Gregorio E, Del Giudice G, Siegrist C A: MF59 Mediates Its B Cell Adjuvanticity by Promoting T Follicular Helper Cells and Thus Germinal Center Responses in Adult and Early Life. *J Immunol* 2015, 194:4836-4845.
20. Pompano R R, Chen J, Verbus E A, Han H, Fridman A, McNeely T, Collier J H, Chong A S: Titrating T-cell epitopes within self-assembled vaccines optimizes CD4+ helper T cell and antibody outputs. *Adv Healthc Mater* 2014, 3:1898-1908.
21. Guarner J: Three Emerging Coronaviruses in Two Decades. *Am J Clin Pathol* 2020, 153:420-421.
22. Du L, He Y, Zhou Y, Liu S, Zheng B J, Jiang S: The spike protein of SARS-CoV—a target for vaccine and therapeutic development. *Nat Rev Microbiol* 2009, 7:226-236.
23. Coutard B, Valle C, de Lamballerie X, Canard B, Seidah N G, Decroly E: The spike glycoprotein of the new coronavirus 2019-nCoV contains a furin-like cleavage site absent in CoV of the same clade. *Antiviral Res* 2020, 176:104742.
24. He Y, Zhou Y, Liu S, Kou Z, Li W, Farzan M, Jiang S: Receptor-binding domain of SARS-CoV spike protein induces highly potent neutralizing antibodies: implication for developing subunit vaccine. *Biochem Biophys Res Commun* 2004, 324:773-781.
25. Graham R L, Donaldson E F, Baric R S: A decade after SARS: strategies for controlling emerging coronaviruses. *Nat Rev Microbiol* 2013, 11:836-848.
26. Thevarajan I, Buising K L, Cowie B C: Clinical presentation and management of COVID-19. *Med J Aust* 2020, 213:134-139.
27. Climent N, Martinez-Navio J M, Gil C, Garcia F, Rovira C, Hurtado C, Miralles L, Gatell J M, Gallart T, Mallol J, et al.: Adenosine deaminase enhances T-cell response elicited by dendritic cells loaded with inactivated HIV. *Immunol Cell Biol* 2009, 87:634-639.
28. Martinez-Navio J M, Climent N, Pacheco R, Garcia F, Plana M, Nomdedeu M, Oliva H, Rovira C, Miralles L, Gatell J M, et al.: Immunological dysfunction in HIV-1-infected individuals caused by impairment of adenosine deaminase-induced costimulation of T-cell activation. *Immunology* 2009, 128:393-404.
29. Baliban S M, Michael A, Shammassian B, Mudakha S, Khan A S, Cocklin S, Zentner I, Latimer B P, Bouillaut L, Hunter M, et al.: An optimized, synthetic DNA vaccine encoding the toxin A and toxin B receptor binding domains of *Clostridium difficile* induces protective antibody responses in vivo. *Infect Immun* 2014, 82:4080-4091.
30. Laddy D J, Yan J, Kutzler M, Kobasa D, Kobinger G P, Khan A S, Greenhouse J, Sardesai N Y, Draghia-Akli R, Weiner D B: Heterosubtypic protection against pathogenic human and avian influenza viruses via in vivo electroporation of synthetic consensus DNA antigens. *PLoS One* 2008, 3:e2517.
31. Kutzler M A, Robinson T M, Chattergoon M A, Choo D K, Choo A Y, Choe P Y, Ramanathan M P, Parkinson R, Kudchodkar S, Tamura Y, et al.: Coimmunization with an optimized IL-15 plasmid results in enhanced function and longevity of CD8 T cells that are partially independent of CD4 T cell help. *J Immunol* 2005, 175:112-123.
32. Latimer B, Toporovski R, Yan J, Pankhong P, Morrow M P, Khan A S, Sardesai N Y, Welles S L, Jacobson J M, Weiner D B, et al.: Strong HCV NS3/4a, NS4b, NS5a, NS5b-specific cellular immune responses induced in Rhesus macaques by a novel HCV genotype 1a/1b consensus DNA vaccine. *Hum Vaccin Immunother* 2014, 10:2357-2365.
33. Kutzler M A, Wise M C, Hutnick N A, Moldoveanu Z, Hunter M, Reuter M, Yuan S, Yan J, Ginsberg A, Sylvester A, et al.: Chemokine-adjuvanted electroporated DNA vaccine induces substantial protection from simian immunodeficiency virus vaginal challenge. *Mucosal Immunol* 2016, 9:13-23.
34. Kathuria N, Kraynyak K A, Carnathan D, Betts M, Weiner D B, Kutzler M A: Generation of antigen-specific immunity following systemic immunization with DNA vaccine encoding CCL25 chemokine immunoadjuvant. *Hum Vaccin Immunother* 2012, 8:1607-1619.
35. Gary E N, Kathuria N, Makurumidze G, Curatola A, Ramamurthi A, Bernui M E, Myles D, Yan J, Pankhong P, Muthumani K, et al.: CCR10 expression is required for the adjuvant activity of the mucosal chemokine CCL28 when delivered in the context of an HIV-1 Env DNA vaccine. *Vaccine* 2020, 38:2626-2635.
36. Ibarrondo F J, Fulcher J A, Goodman-Meza D, Elliott J, Hofmann C, Hausner M A, Ferbas K G, Tobin N H, Aldrovandi G M, Yang 00: Rapid decay of anti-SARS-CoV-2 antibodies in persons with mild Covid-19. *New England Journal of Medicine* 2020.
37. Ghneim H, Al-Saleh S, Al-Shammary F, Kordee Z J C B, biochemistry F C, disease imbaao: Changes in adenosine deaminase activity in ageing cultured human cells and the role of zinc. 2003, 21:275-282.
38. Dullaers M, Li D, Xue Y, Ni L, Gayet I, Morita R, Ueno H, Palucka K A, Banchereau J, Oh S: A T cell-dependent mechanism for the induction of human mucosal homing immunoglobulin A-secreting plasmablasts. *Immunity* 2009, 30:120-129.
39. King I L, Mohrs M: IL-4-producing CD4+ T cells in reactive lymph nodes during helminth infection are T follicular helper cells. *J Exp Med* 2009, 206:1001-1007.
40. Reinhardt R L, Liang H E, Locksley R M: Cytokine-secreting follicular T cells shape the antibody repertoire. *Nat Immunol* 2009, 10:385-393.
41. Yusuf I, Kageyama R, Monticelli L, Johnston R J, Ditoro D, Hansen K, Barnett B, Crotty S: Germinal center T follicular helper cell IL-4 production is dependent on signaling lymphocytic activation molecule receptor (CD150). *J Immunol* 2010, 185:190-202.
42. Tardif V, Muir R, Cubas R, Chakhtoura M, Wilkinson P, Metcalf T, Herro R, Haddad E K: Adenosine deaminase-1 delineates human follicular helper T cell function and is altered with HIV. *Nat Commun* 2019, 10:823.
43. Valerio D, Duyvesteyn M G, van Ormondt H, Meera Khan P, van der Eb A J: Adenosine deaminase (ADA) deficiency in cells derived from humans with severe combined immunodeficiency is due to an aberration of the ADA protein. *Nucleic Acids Res* 1984, 12:1015-1024.
44. Metcalf T U, Cubas R A, Ghneim K, Cartwright M J, Grevenynghe J V, Richner J M, Olagnier D P, Wilkinson P A, Cameron M J, Park B S, et al.: Global analyses revealed age-related alterations in innate immune responses after stimulation of pathogen recognition receptors. *Aging Cell* 2015, 14:421-432.
45. Metcalf T U, Wilkinson P A, Cameron M J, Ghneim K, Chiang C, Wertheimer A M, Hiscott J B, Nikolich-Zugich J, Haddad E K: Human Monocyte Subsets Are Transcriptionally and Functionally Altered in Aging in Response to Pattern Recognition Receptor Agonists. *J Immunol* 2017, 199:1405-1417.
46. Boyd S D, Joshi S A: High-Throughput DNA Sequencing Analysis of Antibody Repertoires. *Microbiol Spectr* 2014, 2.
47. Gur Yaari S H K: Practical guidelines for B-cell receptor repertoire sequencing analysis. *Genome Medicine* 2015, 7:121.
48. Bolotin D A, Poslavsky S, Mitrophanov I, Shugay M, Mamedov I Z, Putintseva E V, Chudakov D M: MiXCR: software for comprehensive adaptive immunity profiling. *Nat Methods* 2015, 12:380-381.
49. Kashiwagi S, Yuan J, Forbes B, Hibert M L, Lee E L, Whicher L, Goudie C, Yang Y, Chen T, Edelblute B, et al.: Near-infrared laser adjuvant for influenza vaccine. *PLoS One* 2013, 8:e82899.
50. Laura P. van Lieshout J M D, Tara N. Rindler, Stephanie A. Booth, James P. Bridges, Sarah K. Wootton: Novel Triple-Mutant AAV6 Capsid Induces Rapid and Potent Transgene Expression in the Muscle and Respiratory Tract of Mice. *Methods and Clinical Development* 2018, 9:323-329.

EMBODIMENTS

1. A polynucleotide encoding Adenosine deaminase-1 (ADA-1) comprising the sequence of SEQ ID NO: 1 (human), or a sequence sharing at least 90% identity therewith.

2. A polynucleotide encoding ADA-1 comprising the sequence of SEQ ID NO: 3 (mouse), or a sequence sharing at least 90% identity therewith.

3. A polynucleotide encoding a fusion protein, said fusion protein comprising an IgE signal peptide and an ADA-1.

4. The polynucleotide of embodiment 3, wherein said fusion protein has the sequence of SEQ ID NO: 5 or a sequence sharing at least 95% identity therewith.

5. A vector comprising the polynucleotide of any of embodiments 1 to 4.

6. The vector comprising the polynucleotide of embodiment 5, wherein the vector is a plasmid.

7. The vector comprising the polynucleotide of embodiment 5, wherein the vector is a viral vector.

8. A fusion protein comprising an IgE signal peptide and an ADA-1.

9. The fusion protein of embodiment 8, wherein the ADA-1 is a human or mouse ADA-1.

10. The fusion protein of embodiment 5, comprising the sequence of SEQ ID NO: 5, or a sequence sharing at least 95% identity therewith.

11. A vaccine composition comprising a vector comprising a polynucleotide encoding ADA-1 as an adjuvant.

12. The composition of embodiment 11, wherein the vector is a plasmid.

13. The composition of embodiment 11, wherein the vector is a viral vector.

14. The composition of any of embodiments 11 to 13, wherein the polynucleotide encodes an ADA-1 fusion protein comprising an IgE signal peptide and an ADA-1.

15. The composition of any of embodiments 11 to 14, wherein the ADA-1 is a human ADA-1.

16. The composition of any of embodiments 11 to 14, wherein the ADA-1 is a murine ADA-1.

17. The composition of any of embodiments 11 to 15, wherein the polynucleotide is SEQ ID NO: 1, or a sequence sharing at least 90% identity therewith.

18. The composition of any of embodiments 11 to 15, wherein the polynucleotide is SEQ ID NO: 3, or a sequence sharing at least 90% identity therewith.

19. The composition of any of embodiments 11 to 18, further comprising a pharmaceutically acceptable carrier.

20. A method of increasing vaccine response in a subject, comprising providing ADA-1 in combination with a vaccine composition.

21. The method of embodiment 20, wherein the subject is an adult over 60 years of age.

22. The method of embodiment 20 or 21, wherein the vaccine composition is a COVID-19 vaccine.

23. The method of embodiment 20 or 21, wherein the vaccine composition is an HIV-1 vaccine.

24. The method of any of embodiments 20-23, comprising administering the polynucleotide of any of embodiments 1 to 4, the vector of any of embodiments 1 to 7, the fusion protein of any of embodiments 9 to 10, or the composition of any of embodiments 11 to 19.

The invention claimed is:

1. An engineered polynucleotide encoding Adenosine deaminase-1 (ADA-1) comprising the sequence of SEQ ID NO: 1, a sequence sharing at least 90% identity therewith, SEQ ID NO: 3, or a sequence sharing at least 90% identity therewith.

2. A polynucleotide encoding a fusion protein, said fusion protein comprising an IgE signal peptide and an ADA-1, wherein said fusion protein has a sequence comprising SEQ ID NO: 5 or a sequence sharing at least 95% identity therewith.

3. A vector comprising a polynucleotide encoding Adenosine deaminase-1 (ADA-1) comprising the sequence of SEQ ID NO: 1, a sequence sharing at least 90% identity therewith, SEQ ID NO: 3, or a sequence sharing at least 90% identity therewith.

4. The vector of claim 3, wherein the vector is a plasmid or a viral vector.

5. A fusion protein comprising an IgE signal peptide and an ADA-1 synthesized from the polynucleotide of claim 2.

6. The fusion protein of claim 5, wherein the ADA-1 is a human or mouse ADA-1.

7. The fusion protein of claim 5, comprising the sequence of SEQ ID NO: 5, or a sequence sharing at least 95% identity therewith.

8. A vaccine composition comprising the vector of claim 3 wherein the polynucleotide encodes ADA-1 as an adjuvant.

9. The composition of claim 8, wherein the vector is a plasmid or viral vector.

10. The composition of claim 8, wherein the polynucleotide encodes an ADA-1 fusion protein comprising an IgE signal peptide and an ADA-1.

11. The composition of claim 8, wherein the ADA-1 is a human ADA-1 or a murine ADA-1.

12. The composition of claim 8, wherein the polynucleotide is SEQ ID NO: 1, or a sequence sharing at least 90% identity therewith.

13. The composition of claim 8, wherein the polynucleotide is SEQ ID NO: 3, or a sequence sharing at least 90% identity therewith.

14. The composition of claim 8, further comprising a pharmaceutically acceptable carrier.

15. A method of increasing vaccine response in a subject, comprising providing the polynucleotide encoding ADA-1 of claim 1 in combination with a vaccine composition.

16. The method of claim 15, wherein the subject is an adult over 60 years of age.

17. The method of claim 15, wherein the vaccine composition is a COVID-19 vaccine or an HIV-1 vaccine.

18. A method of increasing vaccine response in a subject, comprising providing ADA-1 in combination with a vaccine composition, comprising administering the fusion protein of claim 5.

19. A method of increasing vaccine response in a subject, comprising providing ADA-1 in combination with a vaccine composition, comprising administering the vaccine composition of claim 8.

* * * * *